US012157770B2

(12) United States Patent
Dengl et al.

(10) Patent No.: US 12,157,770 B2
(45) Date of Patent: Dec. 3, 2024

(54) ANTI-HLA-G ANTIBODIES AND METHODS OF USE THEREOF

(71) Applicant: Hoffmann-La Roche Inc., Little Falls, NJ (US)

(72) Inventors: Stefan Dengl, Penzberg (DE); Sebastian Fenn, Penzberg (DE); Jens Fischer, Penzberg (DE); Andreas Hinz, Penzberg (DE); Claudia Kirstenpfad, Penzberg (DE); Stefan Klostermann, Penzberg (DE); Joerg Moelleken, Penzberg (DE); Georg Tiefenthaler, Penzberg (DE); Sabine Hoves, Penzberg (DE); Alexander Bujotzek, Penzberg (DE); Meher Majety, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 244 days.

(21) Appl. No.: 17/072,548

(22) Filed: Oct. 16, 2020

(65) Prior Publication Data

US 2021/0147553 A1 May 20, 2021

Related U.S. Application Data

(63) Continuation of application No. PCT/EP2019/060007, filed on Apr. 17, 2019.

(30) Foreign Application Priority Data

Apr. 18, 2018 (EP) ..................... 18168011

(51) Int. Cl.
*C07K 16/28* (2006.01)
*G01N 33/68* (2006.01)
(52) U.S. Cl.
CPC ..... *C07K 16/2833* (2013.01); *G01N 33/6854* (2013.01); *C07K 2317/33* (2013.01); *C07K 2317/76* (2013.01); *C07K 2317/92* (2013.01)
(58) Field of Classification Search
CPC ............ C07K 16/2833; C07K 2317/33; C07K 2317/76; C07K 2317/92; G01N 33/6854
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 5,208,020 A | 4/1993 | Chari et al. | |
| 5,416,064 A | 5/1995 | Chari et al. | |
| 5,500,362 A | 3/1996 | Robinson et al. | |
| 5,591,828 A | 1/1997 | Bosslet et al. | |
| 5,624,821 A | 4/1997 | Winter et al. | |
| 5,635,483 A | 6/1997 | Pettit et al. | |
| 5,648,237 A | 7/1997 | Carter | |
| 5,648,260 A | 7/1997 | Winter et al. | |
| 5,712,374 A | 1/1998 | Kunstmann et al. | |
| 5,714,586 A | 2/1998 | Kunstmann et al. | |
| 5,731,168 A | 3/1998 | Carter et al. | |
| 5,739,116 A | 4/1998 | Hamann et al. | |
| 5,750,373 A | 5/1998 | Garrard et al. | |
| 5,767,285 A | 6/1998 | Hamann et al. | |
| 5,770,429 A | 6/1998 | Lonberg et al. | |
| 5,770,701 A | 6/1998 | McGahren et al. | |
| 5,770,710 A | 6/1998 | McGahren et al. | |
| 5,773,001 A | 6/1998 | Hamann et al. | |
| 5,780,588 A | 7/1998 | Pettit et al. | |
| 5,789,199 A | 8/1998 | Joly et al. | |
| 5,821,337 A | 10/1998 | Carter et al. | |
| 5,840,523 A | 11/1998 | Simmons et al. | |
| 5,869,046 A | 2/1999 | Presta et al. | |
| 5,877,296 A | 3/1999 | Hamann et al. | |
| 5,959,177 A | 9/1999 | Hein et al. | |
| 6,040,498 A | 3/2000 | Stomp et al. | |
| 6,075,181 A | 6/2000 | Kucherlapati et al. | |
| 6,150,584 A | 11/2000 | Kucherlapati et al. | |
| 6,171,586 B1 | 1/2001 | Lam et al. | |
| 6,248,516 B1 | 6/2001 | Winter et al. | |
| 6,267,958 B1 | 7/2001 | Andya et al. | |
| 6,417,429 B1 | 7/2002 | Hein et al. | |
| 6,420,548 B1 | 7/2002 | Vezina et al. | |
| 6,630,579 B2 | 10/2003 | Chari et al. | |
| 6,737,056 B1 | 5/2004 | Presta | |
| 6,982,321 B2 | 1/2006 | Winter | |
| 7,041,870 B2 | 5/2006 | Tomizuka et al. | |
| 7,087,409 B2 | 8/2006 | Barbas, III et al. | |
| 7,125,978 B1 | 10/2006 | Vezina et al. | |
| 7,189,826 B2 | 3/2007 | Rodman | |
| 7,332,581 B2 | 2/2008 | Presta | |
| 7,371,826 B2 | 5/2008 | Presta | |
| 7,498,298 B2 | 3/2009 | Doronina et al. | |
| 7,521,541 B2 | 4/2009 | Eigenbrot et al. | |

(Continued)

FOREIGN PATENT DOCUMENTS

| | | |
|---|---|---|
| CN | 1308675 A | 8/2001 |
| CN | 1718588 A | 1/2006 |

(Continued)

OTHER PUBLICATIONS

Allan, D., et al., "Tetrameric complexes of HLA-E, HLA-F, and HLA-G" J Immunol Methods 268(1):43-50 (Oct. 1, 2002).

(Continued)

*Primary Examiner* — Robert S Landsman
(74) *Attorney, Agent, or Firm* — Clark & Elbing LLP; Karen L. Elbing

(57) ABSTRACT

The present invention relates to anti-HLA-G antibodies and methods of using the same.

11 Claims, 20 Drawing Sheets

Specification includes a Sequence Listing.

(56) References Cited

U.S. PATENT DOCUMENTS

| | | |
|---|---|---|
| 7,527,791 B2 | 5/2009 | Adams et al. |
| 7,695,936 B2 | 4/2010 | Carter et al. |
| 2003/0232051 A1 | 12/2003 | Long et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0163770 A1 | 7/2005 | Reiter |
| 2005/0260186 A1 | 11/2005 | Bookbinder et al. |
| 2005/0266000 A1 | 12/2005 | Bond et al. |
| 2006/0025576 A1 | 2/2006 | Miller et al. |
| 2006/0104968 A1 | 5/2006 | Bookbinder et al. |
| 2007/0020703 A1 | 1/2007 | Menier et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0259403 A1 | 11/2007 | Miyagawa et al. |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2011/0142864 A1 | 6/2011 | Dengjel |
| 2014/0051834 A1 | 2/2014 | Hoffman et al. |
| 2020/0102389 A1 | 4/2020 | Fischer et al. |
| 2021/0147554 A1 | 5/2021 | Dengl et al. |
| 2022/0213199 A1 | 7/2022 | Bujotzek et al. |

FOREIGN PATENT DOCUMENTS

| | | |
|---|---|---|
| CN | 101967191 A | 2/2011 |
| CN | 104203982 A | 12/2014 |
| CN | 106795221 A | 5/2017 |
| EP | 0404097 B1 | 12/1990 |
| EP | 0425235 B1 | 9/1996 |
| EP | 2264067 A1 | 12/2010 |
| EP | 1870459 B1 | 6/2016 |
| JP | 2020-511112 A | 4/2020 |
| RU | 2635537 C2 | 11/2017 |
| WO | 93/01161 A1 | 1/1993 |
| WO | 93/08829 A1 | 5/1993 |
| WO | WO-93/16185 A2 | 8/1993 |
| WO | WO-93/16185 A3 | 9/1993 |
| WO | 94/11026 A2 | 5/1994 |
| WO | 94/11026 A3 | 5/1994 |
| WO | 94/29351 A2 | 12/1994 |
| WO | WO-94/29351 A3 | 2/1995 |
| WO | WO-96/27011 A1 | 9/1996 |
| WO | WO-98/50431 A2 | 11/1998 |
| WO | WO-98/50431 A3 | 1/1999 |
| WO | WO-99/42128 A1 | 8/1999 |
| WO | WO-00/03016 A1 | 1/2000 |
| WO | WO-01/77342 A1 | 10/2001 |
| WO | WO-02/22784 A2 | 3/2002 |
| WO | 2004/056312 A2 | 7/2004 |
| WO | WO-2004/106381 A1 | 12/2004 |
| WO | WO-2005/061547 A2 | 7/2005 |
| WO | WO-2005/100402 A1 | 10/2005 |
| WO | WO-2006/029879 A2 | 3/2006 |
| WO | 2006/044908 A2 | 4/2006 |
| WO | WO-2006/029879 A3 | 9/2006 |
| WO | WO-2007/042261 A2 | 4/2007 |
| WO | WO-2007/110205 A2 | 10/2007 |
| WO | WO-2007/147901 A1 | 12/2007 |
| WO | WO-2008/024715 A2 | 2/2008 |
| WO | WO-2008/119567 A2 | 10/2008 |
| WO | 2009/080251 A1 | 7/2009 |
| WO | 2009/080252 A1 | 7/2009 |
| WO | 2009/080253 A1 | 7/2009 |
| WO | 2009/080254 A1 | 7/2009 |
| WO | 2009/089004 A1 | 7/2009 |
| WO | 2010/112193 A1 | 10/2010 |
| WO | 2010/115589 A1 | 10/2010 |
| WO | WO-2010/129304 A2 | 11/2010 |
| WO | 2010/136172 A1 | 12/2010 |
| WO | 2010/145792 A1 | 12/2010 |
| WO | 2010/145793 A1 | 12/2010 |
| WO | WO-2010/150233 A2 | 12/2010 |
| WO | WO-2010/150235 A1 | 12/2010 |
| WO | WO-2010/129304 A3 | 2/2011 |
| WO | WO-2011/034605 A2 | 3/2011 |
| WO | WO-2011/090754 A1 | 7/2011 |
| WO | WO-2011/090762 A1 | 7/2011 |
| WO | 2011/117330 A1 | 9/2011 |
| WO | WO-2010/115589 A8 | 10/2011 |
| WO | WO-2010/145792 A8 | 10/2011 |
| WO | WO-2011/143545 A1 | 11/2011 |
| WO | WO-2012020006 A2 | 2/2012 |
| WO | 2012/025525 A1 | 3/2012 |
| WO | 2012/025530 A1 | 3/2012 |
| WO | WO-2012/041968 A1 | 4/2012 |
| WO | WO-2012/058768 A1 | 5/2012 |
| WO | WO-2012/058768 A8 | 6/2012 |
| WO | 2013/026831 A1 | 2/2013 |
| WO | 2013/026835 A1 | 2/2013 |
| WO | WO-2013/026833 A1 | 2/2013 |
| WO | WO-2013/026839 A1 | 2/2013 |
| WO | WO-2013/059885 A2 | 5/2013 |
| WO | WO-2013/096291 A2 | 6/2013 |
| WO | WO-2013/106586 A2 | 7/2013 |
| WO | WO-2013/120929 A1 | 8/2013 |
| WO | WO-2013/096291 A3 | 9/2013 |
| WO | WO-2013/157953 A1 | 10/2013 |
| WO | WO-2013/157954 A1 | 10/2013 |
| WO | 2013/164325 A1 | 11/2013 |
| WO | 2013/174873 A1 | 11/2013 |
| WO | WO-2014/072534 A1 | 5/2014 |
| WO | WO-2015066379 A2 | 5/2015 |
| WO | WO-2015/095539 A1 | 6/2015 |
| WO | WO-2015/150447 A1 | 10/2015 |
| WO | WO-2016/016299 A1 | 2/2016 |
| WO | WO-2016/020309 A1 | 2/2016 |
| WO | 2016/062734 A1 | 4/2016 |
| WO | WO-2016/094566 A2 | 6/2016 |
| WO | WO-2016/160622 A2 | 10/2016 |
| WO | WO-2016/172485 A2 | 10/2016 |
| WO | WO-2017060144 A1 | 4/2017 |
| WO | 2017/207775 A1 | 12/2017 |
| WO | WO-2019/202040 A1 | 10/2019 |
| WO | WO-2019/202041 A1 | 10/2019 |
| WO | WO-2020/043899 A1 | 3/2020 |
| WO | WO-2020/127618 A1 | 6/2020 |

OTHER PUBLICATIONS

Amiot, L., et al., "Biology of HLA-G in cancer: a candidate molecule for therapeutic intervention?" Cell Mol Life Sci 68(3):417-431 (Feb. 1, 2011).

Amiot, L., et al., "Immunomodulatory Properties of HLA-G in Infectious Diseases" J Immunol Res 2014:1-14 (Jan. 1, 2014).

Amodio, G., et al., "New insights into HLA-G mediated tolerance" Tissue Antigens 84(3):255-263 (Aug. 13, 2014).

Apps, R., et al., "HLA-G is present on the surface of normal extravillous trophoblast as homodimers with high avidity for the LILR receptors of decidual leukocytes" Abstract (Abstract No. 00020) 4th International Conference on HLA-G, Paris France, pp. 68:359 (Jul. 10-12, 2006).

Borges, L. et al. Immunoreceptor Tyrosine-based Inhibition Motifs "Interactions of LIRs, a Family of Immunoreceptors Expressed in Myeloid and Lymphoid Cells, with Viral and Cellular MHC Class I Antigens" Daeron, M. and Vivier, E., eds., Heidelberg GmbH:Springer-Verlag Berlin, vol. 244:123-136 (1999).

Boyson, J., et al., "Disulfide bond-mediated dimerization of HLA-G on the cell surface" PNAS 99(25):16180-16185 (Dec. 10, 2002).

Brennan, M. et al., "Preparation of bispecific antibodies by chemical recombination of monoclonal immunoglobulin G1 fragments" Science 229(Suppl 4708):81-83 (Jul. 5, 1985).

Cantoni, C., et al., "p49, a putative HLA class I-specific inhibitory NK receptor belonging to the immunoglobulin superfamily" Eur J Immunol 28(6):1980-1990 (Jun. 1, 1998).

Chang, C.C., et al., "Tolerization of dendritic cells by TS cells: the crucial role of inhibitory receptors ILT3 and ILT4" Nat Immunol 3(3):237-243 (Mar. 1, 2002).

(56) References Cited

OTHER PUBLICATIONS

Chari, R., et al., "Immunoconjugates containing novel maytansinoids: Promising anticancer drugs" Cancer Res 52(1):127-131 (Jan. 1, 1992).
Charlton, K.A., "Expression and isolation of recombinant antibody fragments in *E. coli*" Methods Mol Biol 248:245-254 (2003).
Chen, Y. et al., "Selection and analysis of an optimized anti-VEGF antibody: crystal structure of an affinity-matured Fab in complex with antigen" J Mol Biol 293(4):865-881 (Nov. 5, 1999).
Chowdhury, P., "Engineering hot spots for affinity enhancement of antibodies" Methods Mol Biol 207:179-196 (2003).
Clements, C.S., et al., "Crystal structure of HLA-G: a nonclassical MHC class I molecule expressed at the fetal-maternal interface" PNAS 102(9):3360-3365 (Mar. 1, 2005).
Colonna, M., et al., "A novel family of Ig-like receptors for HLA class I molecules that modulate function of lymphoid and myeloid cells" J Leukocyte Biol 66(3):375-381 (Mar. 25, 1999).
Dubowchik, G., et al., "Doxorubicin Immunoconjugates Containing Bivalent, Lysosmally-Cleavable Dipeptide Linkages" Bioorg Med Chem Lett 12(11):1529-1532 (Jun. 3, 2002).
Duncan, A., et al., "The Binding Site for C1q on IgG" Nature 332(6166):738-740 (Apr. 21, 1988).
Fournel, S., et al., "Comparative reactivity of different HLA-G monoclonal antibodies to soluble HLA-G molecules" Tissue Antigens 55(6):510-518 (Jun. 1, 2000).
Gerngross, T., "Advances in the Production of Human Therapeutic Proteins in Yeasts and Filamentous Fungi" Nat Biotechnol 22(11):1409-1414 (Nov. 22, 2004).
Gonen-Gross T. et al., "Complexes of HLA-G Protein on the Cell Surface Are Important for Leukocyte Ig-Like Receptor-1 Function" J Immunol 171(3):1343-1351 (Aug. 1, 2003).
Graham, F., et al., "Characteristics of a Human Cell Line Transformed by DNA from Human Adenovirus Type 5" J Gen Virol 36(1):59-74 (Feb. 1, 1977).
Gruber, M. et al., "Efficient tumor cell lysis mediated by a bispecific single chain antibody expressed in *Escherichia coli*" J Immunol 152(11):5368-5374 (Jun. 1, 1994).
Guyer, R., et al., "Immunoglobulin binding by mouse intestinal epithelial cell receptors" J Immunol 117(2):587-593 (Aug. 1, 1976).
Hinman, L., et al., "Preparation and characterization of monoclonal antibody conjugates of the calicheamicins: a novel and potent family of antitumor antibiotics" Cancer Res 53(14):3336-3342 (Jul. 15, 1993).
Holliger, P., et al., "Diabodies: Small Bivalent and Bispecific Antibody Fragments" PNAS 90(14):6444-6448 (Jul. 15, 1993).
Hoogenboom, H., et al., "Overview of antibody phage-display technology and its applications" Methods Mol Biol 178:1-37 (2002).
Hudson, P., et al., "Engineered antibodies" Nat Med 9(1):129-134 (Jan. 1, 2003).
Hunt, J.S., et al., "HLA-G and immune tolerance in pregnancy" FASEB J 19(7):681-693 (May 1, 2005).
International Preliminary Report on Patentability—PCT/EP2019/060007; (dated Oct. 20, 2020—Chapter I), pp. 1-11 (Oct. 29, 2020)
International Search Report—PCT/EP2019/060007, pp. 1-19 (dated Jul. 17, 2019).
Jeffrey, S., et al., "Dipeptide-based highly potent doxorubicin antibody conjugates" Bioorg Med Chem Lett 16(2):358-362 (Jan. 15, 2006).
Ju, X., et al., "Immunoglobulin-like transcripts ILT2, ILT3, and ILT7 are expressed by human dendritic cells and down-regulated following activation" Gene 331:159-164 (Feb. 9, 2004).
Kam, N., et al., "Carbon nanotubes as multifunctional biological transporters and near-infrared agents for selective cancer cell destruction" PNAS 102(33):11600-11605 (Aug. 16, 2005).
Kim, J., et al., "Localization of the site of the murine IgG1 molecule that is involved in binding to the murine intestinal Fc receptor" Eur J Immunol 24(10):2429-2434 (Oct. 1, 1994).
King, H.D., et al., "Monoclonal antibody conjugates of doxorubicin prepared with branched peptide linkers: Inhibition of aggregation by methoxytriethyleneglycol chains" J Med Chem 45(19):4336-4343 (Sep. 12, 2002).
Kostelny, S., et al., "Formation of a bispecific antibody by the use of leucine zippers" J Immunol 148(5):1547-1553 (Mar. 1, 1992)
Kratz, F., et al., "Prodrugs of anthracyclines in cancer chemotherapy" Curr Med Chem 13(5):477-523 (Mar. 1, 2006).
Kuroki, K et al., "Immune modulation of HLA-G dimer in maternal-fetal interface" Eur J Immunol 37(7):1727-1729 (Jul. 1, 2007).
Li, H., et al., "Optimization of humanized IgGs in glycoengineered Pichia pastoris" Nat Biotechnol 24(2):210-215 (Feb. 1, 2006).
Lin, A., et al., "Human Leukocyte Antigen-G (HLA-G) Expression in Cancers: Roles in Immune Evasion, Metastasis and Target for Therapy" Mol Med 21(1):782-791 (Jan. 1, 2015).
Lode, H.N., et al., "Targeted therapy with a novel enediyene antibiotic calicheamicin V11 effectviely suppresses growth and dissemination of liver metastases in a syngeneic model of murine neuroblastoma" Cancer Res 58(14):2925-2928 (Jul. 15, 1998).
Maric, M., et al., "Defective Antigen Processing in GILT-Free Mice" Science 294(9):1361-1365 (Aug. 20, 2001).
Mather, J., "Establishment and characterization of two distinct mouse testicular epithelial cell lines" Biol Reprod 23(1):243-252 (Aug. 1, 1980).
Mather, J., et al., "Culture of Testicular Cells in Hormone-Supplemented Serum-Free Medium" Ann NY Acad Sci 383:44-68 (Jan. 1, 1982).
Menier, C., et al., "Characterization of Monoclonal Antibodies Recognizing HLA-G or HLA-E: New Tools to Analyze the Expression of Nonclassical HLA Class I Molecules" Hum Immunol 64(3):315-326 (Mar. 1, 2003).
Milstein, C., et al., "Hybrid hybridomas and their use in immunohistochemistry" Nature 305(5934):537-539 (Oct. 6, 1983).
Morrison, S., et al., "Chimeric human antibody molecules: Mouse antigen-binding domains with human constant region domains" PNAS 81(21):6851-6855 (Nov. 1, 1984).
Nagy, A., et al., "Stability of cytotoxic luteinizing hormone-releasing hormone conjugate (AN-152) containing doxorubicin 14-O-hemiglutarate in mouse and human serumm in vitro: implications for the design of preclinical studies" PNAS USA 97(2):829-834 (Jan. 18, 2000).
Nakajima, H., et al., "Transcriptional Regulation of ILT Family Receptors" J Immunol 171(12):6611-6620 (Dec. 15, 2003).
Polakova, K., et al., "Binding Analysis of HLA-G specific antibodies to hematopoietic cells isolated from leukemia patients" Neoplasma 50(5):331-338 (Mar. 12, 2003).
Ponte, M. et al., "Inhibitory receptors sensing HLA-G1 molecules in pregnancy: Decidua-associated natural killer cells express LIR-1 and CD94yNKG2A and acquire p49, an HLA-G1-specific receptor" PNAS 96(10):5674-5679 (May 11, 1999).
Rajagopalan, S., et al., "A Human Histocompatibility Leukocyte Antigen (HLA)-G-specific Receptor Expressed on All Natural Killer Cells" J Exp Med 189(7):1093-1099 (Apr. 5, 1999).
Ristich, V. et al., "Tolerization of dendritic cells by HLA-G" Eur J Immunol 35(4):1133-1142 (Apr. 1, 2005).
Rudolph, M., et al., "Crystal Structures of Two Rat MHC Class Ia (RT1-A) Molecules that are Associated Differentially with Peptide Transporter Alleles TAP-A and TAP-B" J Mol Biol 324(5):975-990 (Dec. 13, 2002).
Sanders, S.K., et al., "Cell-cell adhesion mediated by CD8 and human histocompatibility leukocyte antigen G, a nonclassical major histocompatibility complex class 1 molecule on cytotrophoblasts" J Exp Med 174(3):737-740 (Sep. 1, 1991).
Selvakumar, A., et al., "NK cell receptor gene of the KIR family with two IG domains but highest homology to KIR receptors with three IG domains" Tissue Antigens (Abstract Only), 48(4 Pt. 1):285-294 (Oct. 1, 1996).
Shields, R., et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).

(56) References Cited

OTHER PUBLICATIONS

Shiroishi, M., et al., "Efficient Leukocyte Ig-like Receptor Signaling and Crystal Structure of Disulfide-linked HLA-G Dimer" J Biol Chem 281(15):10439-10447 (Apr. 14, 2006).
Shiroishi, M., et al., "Human inhibitory receptors Ig-like transcript 2 (ILT2) and ILT4 compete with CD8 for MHC class I binding and bind preferentially to HLA-G" PNAS 100(15):8856-8861 (Jul. 22, 2003).
Suciu-Foca, N., et al., "Molecular characterization of allospecific T suppressor and tolerogenic dendritic cells: review" Int Immunol Pharma 5(1):7-11 (Jan. 1, 2005).
Torgov, M., et al., "Generation of an intensely potent anthracycline by monoclonal antibody-(beta)-galactosidase conjugate" Bioconjugate Chem 16(3):717-721 (May 31, 2005).
Traunecker, A., et al., "Bispecific single chain molecules (Janusins) target cytotoxic lymphocytes on HIV infected cells" EMBO J 10(12):3655-3659 (Dec. 10, 1991).
Tutt, A., et al., "Trispecific F(ab')3 derivatives that use cooperative signaling via the TCR/CD3 complex and the CD2 to activate and redirect resting cytotoxic T cells" J Immunol 147(1):60-69 (Jul. 1, 1991).
Urlaub, G., et al., "Isolation of Chinese hamster cell mutants deficient in dihydrofolate reductase activity" PNAS US 77(7):4216-4220 (Jul. 1, 1980).
Valiante, N.M., et al., "Functionally and structurally distinct NK cell receptor repertoires in the peripheral blood of two human donors" Immunity 7(6):739-751 (Dec. 1, 1997).
Vitetta, E. et al., "Redesigning nature's poisons to create anti-tumor reagents" Science 238(4830):1098-1104 (Nov. 20, 1987).
Wan, R., et al., "Human Leukocyte Antigen-G Inhibits the Anti-Tumor Effect of Naural Killer Cells via Immunoglobulin-Like Transcript 2 in Gastric Cancer" Cell Physiol Biochem 44(5):1828-1841 (Jan. 1, 2017)
Wiendl, H. et al., "The non-classical MHC molecule HLA-G protects human muscle cells from immune-mediated lysis: implications for myoblast transplantation and gene therapy" Brain 126(Pt. 1):176-185 (Jan. 1, 2003).
Wu, D., et al., "Rescuing lymphocytes from HLA-G immunosuppressive effects mediated by the tumor microenvironment" Oncotarget 6(35):37385-37397 (Nov. 10, 2015).
Yazaki, P. J., et al. Methods in Molecular Biology "Expression of recombinant antibodies in mammalian cell lines" Lo, B.K.C. (ed.), Totowa, NJ: Humana Press, vol. 248:255-268 (2004).
Almagro et al., "Humanization of antibodies," Front Biosci. 13:1619-33 (2008).
Atwell et al., "Stable Heterodimers from Remodeling the Domain Interface of a Homodimer using a Phage Display Library," J Mol Biol. 270(1):26-35 (1997).
Baca et al., "Antibody Humanization Using Monovalent Phage Display," J Biol Chem. 272(16):10678-84 (1997) (8 pages).
Bacac et al., "CEA TCB: a novel head-to-tail 2:1 T cell bispecific antibody for treatment of CEA-positive solid tumors," Oncoimmunology. 5(8):e1203498 (2016) (3 pages).
Bensussan et al., "Detection of membrane-bound HLA-G translated products with a specific monoclonal antibody," Proc Natl Acad Sci U S A. 92(22):10292-6 (1995).
Boerner et al., "Production of antigen-specific human monoclonal antibodies from in vitro-primed human splenocytes," J Immunol. 147(1):86-95 (1991).
Brodeur et al., "Mouse-Human Myeloma Partners for the Production of Heterohybridomas," Monoclonal Antibody Production Techniques and Applications. New York:51-63 (1987).
Brüggemann et al., "Comparison of the Effector Functions of Human Immunoglobulins Using a Matched set of Chimeric Antibodies," J Exp Med. 166(5):1351-61 (1987).
Carter et al., "Humanization of an anti-p185$^{HER2}$ antibody for human cancer therapy," Proc Natl Acad Sci U S A. 89(10):4285-9 (1992).
Carter, "Bispecific human IgG by design," J Immunol Methods. 248(1-2):7-15 (2001).

Clackson et al., "Making antibody fragments using phage display libraries," Nature. 352(6336):624-8 (1991).
Clynes et al., "Fc receptors are required in passive and active immunity to melanoma," Proc Natl Acad Sci U S A. 95(2):652-6 (1998).
Cragg et al., "Antibody specificity controls in vivo effector mechanisms of anti-CD20 reagents," Blood. 103(7):2738-43 (2004).
Cragg et al., "Complement-mediated lysis by anti-CD20 mAb correlates with segregation into lipid rafts," Blood. 101(3):1045-52 (2003).
Cunningham et al., "High-Resolution Epitope Mapping of hGH-Receptor Interactions by Alanine-Scanning Mutagenesis," Science. 244(4908):1081-5 (1989).
Dall'Acqua et al., "Antibody humanization by framework shuffling," Methods. 36(1):43-60 (2005).
Ding et al., "OPL077: Experimental Study of Human Umbilical Cord Blood Cells Transplantation for Treatment of Cerebral Ischemia in rats," Journal of the Neurological Sciences. 238:S65 (2005) (Abstract only) (1 page).
Fellouse et al., "Synthetic anitbodies from a four-amino-acid code: a dominant role for tyrosine in antigen recognition," Proc Natl Acad Sci U S A. 101(34):12467-72 (2004).
Fägerstam et al., "Detection of Antigen-Antibody Interactions by Surface Plasmon Resonance: Application to Epitope Mapping," J Mol Recognit. 3(5-6):208-14 (1990).
Gazzano-Santoro et al., "A non-radioactive complement-dependent cytotoxicity assay for anti-CD20 monoclonal antibody," J Immunol Methods. 202(2):163-171 (1997).
Gonen-Gross et al., "The CD85J/Leukocyte Inhibitory Receptor-1 Distinguishes between Conformed and beta2-Microglobulin-Free HLA-G Molecules," J Immunol. 175(8):4866-74 (2005) (10 pages).
Griffiths et al., "Human anti-self antibodies with high specificity from phage display libraries," EMBO J. 12(2):725-34 (1993).
Hara et al., "Altered Expression of Human Leukocyte Antigen G (HLA-G) on Extravillous Trophoblasts in Preeclampsia: Immunohistological Demonstration With Anti-HLA-G Specific Antibody '87G' and Anti-cytokeratin Antibody 'CAM5.2'," Am J Reprod Immunol. 36(8):349-358 (1996).
Hellström et al., "Antitumor effects of L6, an IgG2a antibody that reacts with most human carcinomas," Proc Natl Acad Sci U S A. 83(18):7059-63 (1986).
Hellström et al., "Strong antitumor activities of IgG3 antibodies to a human melanoma-associated ganglioside," Proc Natl Acad Sci U S A. 82(5):1499-1502 (1985).
Holliger et al., "Specific killing of lymphoma cells by cytotoxic T-cells mediated by a bispecific diabody," Protein Eng. 9(3):299-305 (1996).
Hoogenboom et al., "By-passing Immunisation. Human Antibodies from Synthetic Repertoires of Gemline $V_H$ Gene Segments Rearranged in Vitro" J Mol Biol. 227(2):381-88 (1992).
Johnson et al., "Effector Cell Recruitment wiht Novel Fv-based Dual-affinity Re-targeting Protein Leads to Potent Tumor Cytolysis and in Vivo B-cell Depletion," J Mol Biol. 399(3):436-449 (2010).
Kashmiri et al., "SDR grafting—a new approach to antibody humanization," Methods. 36(1):25-34 (2005).
Kipriyanov et al., "Bispecific Tandem Diabody for Tumor Therapy with Improved Antigen Binding and Pharmacokinetics," J Mol Biol. 293(1):41-56 (1999).
Klein et al., "The use of CrossMAb technology for the generation of bi- and multispecific antibodies," MAbs. 8(6):1010-20 (2016).
Klimka et al., "Human anti-CD30 recombinant antibodies by guided phage antibody selection using cell panning," Br J Cancer. 83(2):252-260 (2000).
Kozbor et al., "A Human Hybrid Myeloma for Production of Human Monoclonal Antibodies," J Immunol. 133(6):3001-5 (1984).
Lee et al., "Bivalent antibody phage display mimics natural immunoglobulin," J Immunol Methods. 284(1-2):119-32 (2004).
Lee et al., "High-affinity Human Antibodies from Phage-displayed Synthetic Fab Libraries with a Single Framework Scaffold," J Mol Biol. 340(5):1073-93 (2004).
Li et al., "Human antibodies for immunotherapy development generation via a human B cell hybridoma technology," Proc Natl Acad Sci U S A. 103(10):3557-62 (2006).

(56) References Cited

OTHER PUBLICATIONS

Lo et al., "Effector-attenuating Substitutions That Maintain Antibody Stability and Reduce Toxicity in Mice," J Biol Chem. 292(9):3900-3908 (2017) (10 pages).
Lonberg, "Fully human antibodies from transgenic mouse and phage display platforms," Curr Opin Immunol. 20(4):450-459 (2008).
Lonberg, "Human antibodies from transgenic animals," Nat Biotechnol. 23(9):1117-25 (2005).
Lum et al., "Targeting T Cells with Bispecific Antibodies for Cancer Therapy," available in PMC Oct. 8, 2013, published in final edited form as: Biodrugs. 25(6):365-379 (2011) (24 pages).
Marks et al., "By-passing Immunization Human Antibodies from V-gene Libraries Displayed on Phage," J Mol Biol. 222(3):581-97 (1991).
Marks et al., "Selection of human antibodies from phage display libraries." *Methods in Molecular Biology, vol. 248: Antibody Engineering: Methods and Protocols*, B.K.C. Lo, 161-176 (2004) (29 pages).
McCafferty et al., "Phage antibodies: filamentous phage displaying antibody variable domains," Nature. 348(6301):552-4 (1990).
Meissner et al., "Transient Gene Expression: Recombinant Protein Production with Suspension-Adapted HEK293-EBNA Cells," Biotechnol Bioeng. 75(2):197-203 (2001).
Menier et al., "MICA Triggering Signal for NK Cell Tumor Lysis is Counteracted by HLA-G1-Mediated Inhibitory Signal," Int J Cancer. 100(1):63-70 (2002).
Nagorsen et al., "Immunomodulatory therapy of cancer with T cell-engaging BiTE antibody blinatumomab," Exp Cell Res. 317(9):1255-60 (2011).
Ni, "Research progress and future perspectives in antibodomics and antibodomic drugs," HCAPLUS Accession No. 2006:1101736. Xiandai Mianyixue. 26(4):265-268 (2006) (Abstract Only) (3 pages).
Osbourn et al., "From rodent reagents to human therapeutics using antibody guided selection," Methods. 36(1):61-8 (2005).
Padlan, "A possible procedure for reducing the immunogenicity of antibody variable domains while preserving their ligand-binding properties," Mol Immunol. 28(4-5):489-98 (1991).
Petkova et al., "Enhanced half-life of genetically engineered human IgG1 antibodies in a humanized FcRn mouse model: potential application in humorally mediated autoimmune disease," Int Immunol. 18(12):1759-69 (2006).
Plückthun, Chapter 11: Antibodies from *Escherichia coli. The Pharmacology of Monoclonal Antibodies*. Martin Rosenberg and Gordon P. Moore, 269-315 (1994) (26 pages).
Presta et al., "Humanization of an Antibody Directed Against IgE," J Immunol. 151(5):2623-32 (1993).
Queen et al., "A humanized antibody that binds to the interleukin 2 receptor," Proc Natl Acad Sci U S A. 86(24):10029-33 (1989).
Ridgway et al., "'Knobs-into-holes' engineering of antibody CH3 domains for heavy chain heterodimerization," Protein Eng. 9(7):617-21 (1996).
Riechmann et al., "Reshaping human antibodies for therapy," Nature. 322(6162):323-7 (1988).
Riteau et al., "HLA-G1 co-expression boosts the HLA class I-mediated NK lysis inhibition," Int Immunol. 13(2):193-201 (2001).
Roosnek et al., "T cell activation by a bispecific anti-CD3/anti-major histocompatibility complex class I antibody," Eur J Immunol. 20(6):1393-6 (1990).
Rosok et al., "A Combinatorial Library Strategy for the Rapid Humanization of Anticarcinoma BR96 Fab," J Biol Chem. 271(37):22611-8 (1996).
Ruan et al., "Recent progress of HLA-G in cancer," Chinese Bulletin of Life Sciences. 24(3):242-49 (2012) (English language abstract).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti-EpCAM × anti-CD3) as a targeted cancer immunotherapy," Cancer Treat Rev. 36(6):458-67 (2010).
Sheu et al., "HLA-G and Immune Evasion in Cancer Cells," J Formos Med Assoc. 109(4):248-57 (2010).
Shore et al., "Chain B, YTS 105.18 Antigen Binding Region Heavy Chain," GenBank, accession No. 2ARJ_B (2020) (3 pages).
Sidhu et al., "Phage-displayed Antibody Libraries of Synthetic Heavy Chain Complementarity Determining Regions," J Mol Biol. 338(2):299-310 (2004).
Sims et al., "A Humanized CD18 Antibody Can Block Function without Cell Destruction," J Immunol. 151(4):2296-308 (1993).
Spiess et al., "Alternative molecular formats and therapeutic applications for bispecific antibodies," Mol Immunol. 67(2 Pt A):95-106 (2015).
Spurny et al., "T cell infiltration into Ewing sarcomas is associated with local expression of immune-inhibitory HLA-G," Oncotarget. 9(5):6536-49 (Dec. 22, 2017).
Stoel et al., "Immunoglobulin heavy chain variable region, partial [Rattus norvegicus]," GenBank, accession No. CAL25600 (2016) (2 pages).
Valliere-Douglass et al., "Glutamine-linked and Non-consensus Asparagine-linked Oligosaccharides Present in Human Recombinant Antibodies Define Novel Protein Glycosylation Motifs," J Biol Chem. 285(21):16012-22 (2010).
Van de Bovenkamp et al., "Adaptive antibody diversification through N-linked glycosylation of the immunoglobulin variable region," Proc Natl Acad Sci U S A. 115(8):1901-1906 (Feb. 20, 2018).
Van Dijk et al., "Human antibodies as next generation therapeutics," Curr Opin Chem Biol. 5(4):368-74 (2001).
Vollmers et al., "Death by Stress: Natural IgM-Induced Apoptosis," Methods Find Exp Clin Pharmacol. 27(3):185-91 (2005).
Vollmers et al., "The 'early birds': natural IgM antibodies and immune surveillance," Histol Histopathol. 20(3):927-37 (2005).
Winter et al., "Making Antibodies by Phage Display Technology," Annu Rev Immunol. 12:433-55 (1994).
Extended European Search Report for European Patent Application No. 20214951.4, dated Jul. 20, 2021 (13 pages).
International Preliminary Report on Patentability for International Application No. PCT/EP2019/060008, dated Oct. 20, 2020 (7 pages).
International Preliminary Report on Patentability for International Patent Application No. PCT/EP2017/079429, dated May 31, 2019 (9 pages).
International Search Report and Written Opinion for International Application No. PCT/EP2019/060008, dated May 27, 2019 (12 pages).
International Search Report and Written Opinion for International Application No. PCT/EP2021/085810, dated Apr. 7, 2022 (20 pages).
International Search Report and Written Opinion for International Application No. PCT/EP2017/079429, dated Mar. 20, 2018 (13 pages).
Invitation to Respond to Written Opinion for Singaporean Application No. 11202009695Q, dated Apr. 27, 2022 (12 pages).
Kuznetzova, E. A., "Brackets in text of legal document as a linguistic and cognitive phenomenon," Vestnik MGOU. Series: Russian Philology. 3:37-42 (2015) (12 pages).
Roitt et al., "Different antigen antibody binding is ensured by hypervariable sequences of antigen-recognizing centers," Moscow, Mir: Immunology. 110-1 (2000) (5 pages).
Singer et al., "Genes and Genomes," Moskow "MIR". 1:63-64 (1998) (7 pages).
Office Action for Russian Patent Application No. 2020 137 068, dated Oct. 5, 2022 (16 pages).
Lu et al., "Preparation of anti-HLA-G monoclonal antibody G11E5," Chin J Cell Mol Immunol. 22(2) (2006) (3 pages).
Zeng et al., "Effect of overexpression of human leukocyte antigen-G in hepatocellular carcinoma Hep3B cells on killing activity of NK cells in vitro," Chinese Journal of Pathophysiology 28(4):613-618 (2012) (6 pages).
Decision to Grant for Russian Patent Application No. 2020 137 068, dated Apr. 5, 2023 (16 pages).
"Annex 4-15E7 Specificity and Blocking Activity," experimental annex cited in opposition to patent EP2917229B1 on Oct. 6, 2020, by Regimbeau (5 pages).

(56) References Cited

OTHER PUBLICATIONS

"Immunologists' Toolbox: Immunization." Excerpt from Janeway's Immunobiology, eds. Murphy et al., 7th ed., p. 735 (2008) (3 pages).
Abcam Product Datasheet for "Anti-HLA G antibody [MEM-G/1] ab7759" cited in opposition to patent EP2917229B1 on Oct. 7, 2020 (3 pages).
Agauguéet al., "Role of HLA-G in tumor escape through expansion of myeloid-derived suppressor cells and cytokinic balance in favor of Th2 versus Th1/Th17," Blood. 117(26):7021-31 (Jun. 30, 2011).
Angal et al., "A single amino acid substitution abolishes the heterogeneity of chimeric mouse/human (IgG4) antibody," Mol Immunol. 30(1):105-8(1993).
Apps et al., "A critical look at HLA-G," Trends Immunol. 29(7):313-21 (2008).
Arns et al., "Structural Modeling and Molecular Dynamics of the Immune Checkpoint Molecule HLA-G," Front. Immunol. 11:575076. doi: 10.3389/fimmu.2020.575076 (Nov. 2020).
Barnstable et al., "Production of monoclonal antibodies to group A erythrocytes, HLA and other human cell surface antigens-new tools for genetic analysis," Cell 14(1) Abstract (1978).
Barnstable et al., "Production of Monoclonal Antibodies to Group A Erythrocytes, HLA and Other Human Cell Surface Antigens-New Tools for Genetic Analysis," Cell. 14(1):9-20 (1978).
Beers et al., "Type II (tositumomab) anti-CD20 monoclonal antibody out performs type I (rituximab-like) reagents in B-cell depletion regardless of complement activation," Blood 112(10):4170-4177 (2008).
Blaschitz et al., "The soluble pool of HLA-G produced by human trophoblasts does not include detectable levels of the intron 4-containing HLA-G5 and HLA-G6 isoforms," Molecular Human Reproduction 11(10):699-710 (2005).
Carosella et al., "Beyond the increasing complexity of the immunomodulatory HLA-G molecule," Blood. 111(10):4862-70 (May 15, 2008).
Carosella et al., "HLA-G: from biology to clinical benefits," Trends in Immunology. 29(3):125-32 (2008).
Chaplin, David D., "Overview of the immune response," J Allergy Clin Immunol. 125(2 Suppl 2):S3-23 (2010).
Chua et al., "Chapter 40: Production of Monoclonal Antibody by DNA Immunization with Electroporation," S. Li (ed.), Electroporation Protocols: Preclinical and Clinical Gene Medicine. From Methods in Molecular Biology. 423:509-20 (2008).
Contini et al., "Soluble HLA-A,-B,-C and -G molecules induce apoptosis in T and Nk CD8+ cells and inhibit cytotoxic T cell activity through CD8 ligation," Eur J Immunol. 33:125-34 (2003).
Deng et al., "Enhancing antibody patent protection using epitope mapping information," MABS 10(2):204-209 (2018).
Desai et al., "Structural Relatedness of Distinct Determinants Recognized by Monoclonal Antibody TP25.99 on beta$_2$-Microglobulin-Associated and beta2-Microglobulin-Free HLA Class I Heavy Chains," J Immunol. 165:3275-83 (2000).
Diaz-Lagares et al., "Nitric oxide produces HLA-G nitration and induces metalloprotease-dependent shedding creating a tolerogenic milieu," Immunology. 126(3):436-45 (2008).
Donadi et al., "Implications of the polymorphism of HLA-G on its function, regulation, evolution and disease association," Cell Mol Life Sci. 68:369-95 (2011).
Fioretti et al., "DNA Vaccines: Developing New Strategies against Cancer," J Biomed Biotechnol. 2010:174378 (2010) (16 pages).
Furukawa et al., "Evaluation of the Reactivity and Receptor Competition of HLA-G Isoforms toward Available Antibodies: Implications of Structural Characteristics of HLA-G Isoforms," Int J Mol Sci. 20:5947 (Nov. 26, 2019).
Gauster et al., "Monoclonal antibody HC10 does not bind HLA-G," Rheumatology. 46:892-3 (2007).
Geraghty et al., "A human major histocompatibility complex class I gene that encodes a protein with a shortened cytoplasmic segment, " Proc Natl Acad Sci USA. 84(1):9145-9 (Dec. 1987).
Ishitani et al., "Protein Expression and Peptide Binding Suggest Unique and Interacting Functional Roles for HLA-E, F, and G in Maternal-Placental Immune Recognition," J Immunol. 171(3):1376-84 (2003).
Kobayashi et al., "Establishment of a Choriocarcinoma Model from Immortalized Normal Extravillous Trophoblast Cells Transduced with HRASV12," Am J Pathol. 179(3):1471-82 (2011).
Kovats et al., "A Class I Antigen, HLA-G, Expressed in Human Trophoblasts," Science 248:220- 223 (1990).
Kutzler et al., "DNA vaccines: ready for prime time?" Nat Rev Genet. 9(10):776-88 (2008).
Laddy et al., "From Plasmids to Protection: A Review of DNA Vaccines Against Infectious Diseases," International Reviews of Immunology. 25:99-123 (2006) (26 pages).
Le Discorde et al., " HLA-G*0105N Null Allele Encodes Functional HLA-G Isoforms," Biol Reprod. 73(2):280-8 (2005).
Le Gal et al., "HLA-G-mediated inhibition of antigen-specific cytotoxic T lymphocytes," International Immunology. 11(8):1351-6 (1999).
Le Rond et al., "Alloreactive CD4$^+$ and CD8$^+$ T cells express the immunotolerant HLA-G molecule in mixed lymphocyte reactions: in vivo implications in transplanted patients," Eur J Immunol. 34(3):649-60 (2004).
Lee et al., "The Membrane-Bound and Soluble Forms of HLA-G Bind Identical Sets of Endogenous Peptides but Differ with Respect to TAP Association," Immunity. 3:591-600 (1995).
Liang et al., "HLA-G inhibits the functoins of murine dendritic cells via the PIR-B immune inhibitory receptor," Eur J Immunol. 32:2418-26 (2002).
Lin et al., "HLA-G expression in human ovarian carcinoma counteracts NK cell function," Annals of Oncology. 18(11):1804-9 (2007).
Loke et al., "Evaluation of trophoblast HLA-G antigen with a specific monoclonal antibody," Tissue Antigens. 50:135-46 (1997).
Loumagne et al., "In vivo evidence that secretion of HLA-G by immunogenic tumor cells allows their evasion from immunosurveillance," Int J Cancer. 135:2107-17 (2014).
Loustau et al., "HLA-G Neo-Expression on Tumors," Frontiers in Immunology. 11(1685) (Aug. 14, 2020) (15 pages).
Mansfield et al., "Regional immunity in melanoma: immunosuppressive changes precede nodal metastasis," Modern Pathol. 24:487-94 (2011).
Markel et al., "Preclinical Evaluation of Adoptive Cell Therapy for Patients with Metastatic Renal Cell Carcinoma," Anticancer Res. 29:145-54 (2009).
Matsushita et al., "Differential but Competitive Binding of Nogo Protein and Class I Major Histocompatibility Complex (MHCI) to the PIR-B Ectodomain Provides an Inhibition of Cells," J Biol Chem. 286(29):25739-47 (2011).
Mcmaster et al., "HLA-G Isoforms Produced by Placental Cytotrophoblasts and Found in Amniotic Fluid Are Due to Unusual Glycosylation," J Immunol. 160(12):5922-8 (1998).
Molek et al., "Epitope Mapping of Mono- and Polyclonal Antibodies by Screening Phage-displayed Random Peptide Libraries," Acta Chim Slov. 63:914-9 (2016).
Morales et al., "Placental Cell Expression of HLA-G2 Isoforms Is Limited to the Invasive Trophoblast Phenotype," J Immunol. 171(11): 6215-24 (2003).
Naji et al., "Soluble HLA-G and HLA-G1 Expressing Antigen-Presenting Cells Inhibit T-Cell Alloproliferation through ILT-2/ILT-4/FasL-Mediated Pathways," Hum Immunol. 68(4):233-9 (2007).
Nencioni et al., "Anticancer vaccination strategies," Ann Oncol. 15(Supplement 4):iv153-iv160 (2004).
Nimmerjahn et al., "Fcgamma receptors as regulators of immune responses," Nature Reviews Immunology 8:34-47 (2008).
Nordic-MUbio Product Datasheet for "Mouse anti Human HLA Class I Heavy Chain (Restricted expression)." Catalogue No. MUB2037P (3 pages).
Parish et al., "Immunogenicity of Low-Dose Intradermal Recombinant DNA Hepatitis B Vaccine," Southern Med J. 84(4):426-30 (1991).

(56) References Cited

OTHER PUBLICATIONS

Paul et al., "HLA-G expression in melanoma: A way for tumor cells to escape from immunosurveillance," Proc Natl Acad Sci USA. 95(8):4510-5 (1998).

Paul et al., "HLA-G, -E, -F Preworkshop: Tools and Protocols for Analysis of Non-Classical Class I Genes Transcription and Protein Expression," Human Immunology. 61(11): 1177-95 (2000).

Pelanda et al., "Central B-Cell Tolerance: Where Selection Begins," Cold Spring Harb Perspect Biol. 4(4):a007146 (2012) (16 pages).

Pirrone et al., "Applications of Hydrogen/Deuterium Exchange MS from 2012 to 2014," Anal. Chem. 87:99-118 (2015).

Riteau et al., "HLA-G2, -G3, and -G4 Isoforms Expressed as Nonmature Cell Surface Glycoproteins Inhibit NK and Antigen-Specific CTL Cytosis," J Immunol. 166:5018-26 (2001) (10 pages).

Rouas-Freiss et al., "Expression of tolerogenic HLA-G molecules in cancer prevents antitumor responses," Seminars in Cancer Biol. 17:413-21 (2007).

Saade et al., "Technologies for enhanced efficacy of DNA vaccines," Expert Rev Vaccines. 11(2):189-209 (2012).

Seitz et al., "The monoclonal antibody HCA2 recognises a broadly shared epitope on a selected classical as well as several non-classical HLA class I molecules," Mol Immunol. 35:819-27 (1998).

Shiroishi et al., "Structural basis for recognition of the nonclassical MHC molecule HLA-G by the leukocyte Ig-like receptor B2 (LILRB2/LIR2/ILT4/CD85d)," PNAS. 103(44): 16412-7 (2006).

Tanabe et al., "Structural and Functional Analysis of Monomorphic Determinants Recognized by Monoclonal Antibodies Reacting with the HLA Class I alpha$_3$ Domain," Journal of Immunology. 148(13):3202-9 (1992).

Temming et al., "Cross-reactivity of mouse IgG subclasses to human Fc gamma receptors: Antibody deglycosylation only eliminates IgG2b binding, " Molecular Immunology 127:79-86 (Sep. 2020).

Tran et al., "The epitope recognized by pan-HLA class I-reactive monoclonal antibody W6/32 and its relationship to unusual stability of the HLA-B27/Beta2-microglobulin complex," Immunogenetics. 53:440-6 (2001).

Tüting et al., "The Immunology of DNA Vaccines," excerpt from "DNA Vaccines: Methods and Protocols." 29:37-8 (2000) (3 pages).

van Lierop et al., "Detection of HLA-G by a specific sandwich ELISA using monoclonal antibodies G233 and 56B," Mol Hum Reprod. 8(8):776-84 (2002).

Vergati et al., "Strategies for Cancer Vaccine Development," J Biomed Biotechnol. 2010:596432 (2010) (13 pages).

Vlieg et al., "Structure and flexibility of the extracellular region of the PirB receptor," J. Biol. Chem. 294(12):4634-4643 (Jan. 2019).

Xing et al., "T-Cell Tolerance: Central and Peripheral," Cold Spring Harb Perspect Biol. 4(6):a006957 (2012) (16 pages).

Yari et al., "Production and Characterization of Monoclonal Antibodies with Specificity for Human HLA-G Isoforms," Hybridoma and Hybridomics. 22(5):301-6 (2003).

Ye et al., "Human leukocyte antigen G expression: as a significant prognostic indicator for patients with colorectal cancer," Modern Pathology. 20(3):375-83 (2007).

Zöller et al., "Prophylactic Tumor Vaccination: Comparison of Effector Mechanisms Initiated by Protein Versus DNA Vaccination," J Immunol. 166:3440-50 (2001).

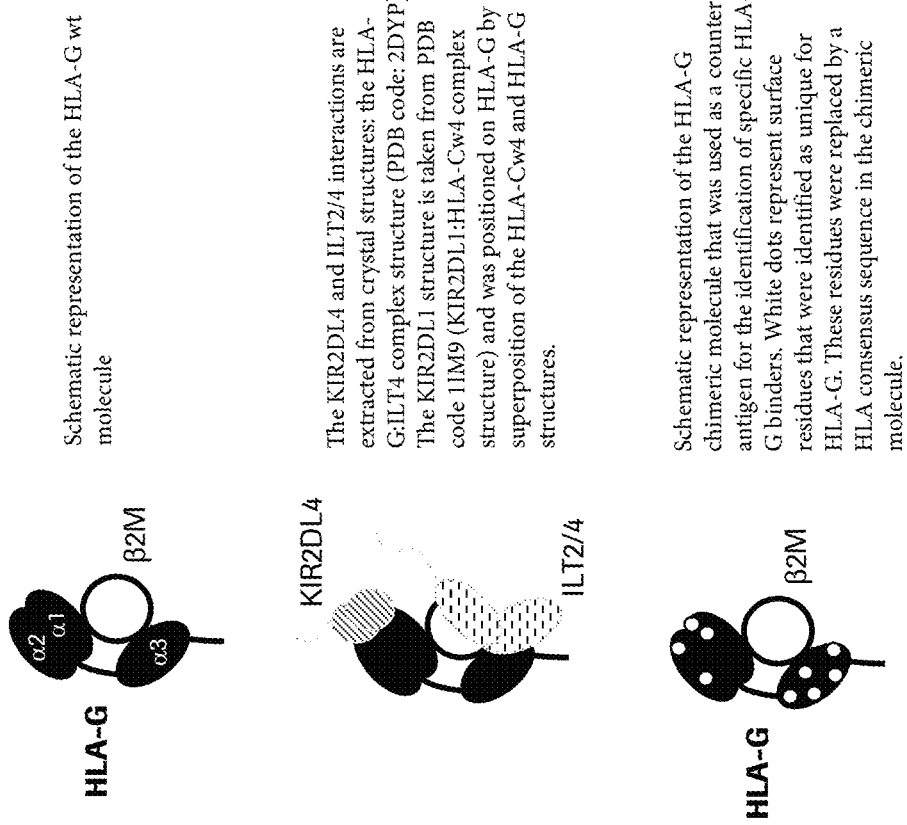

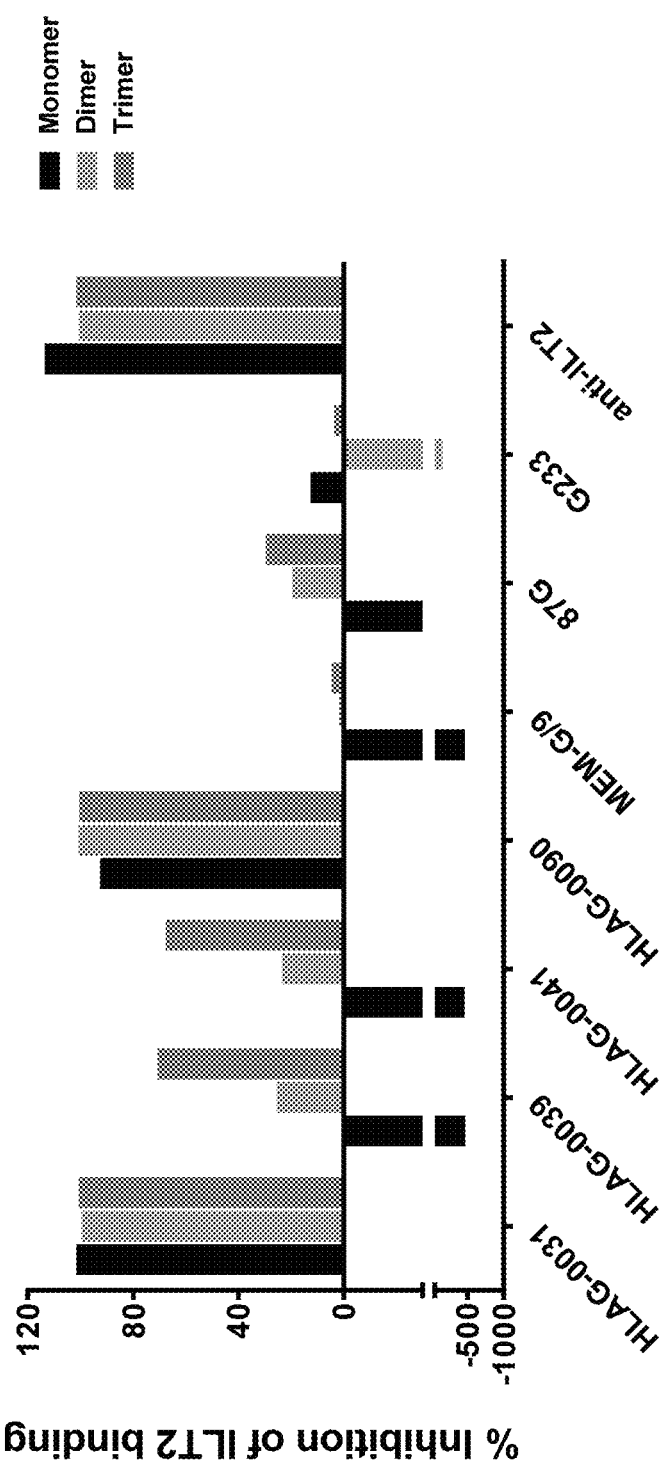

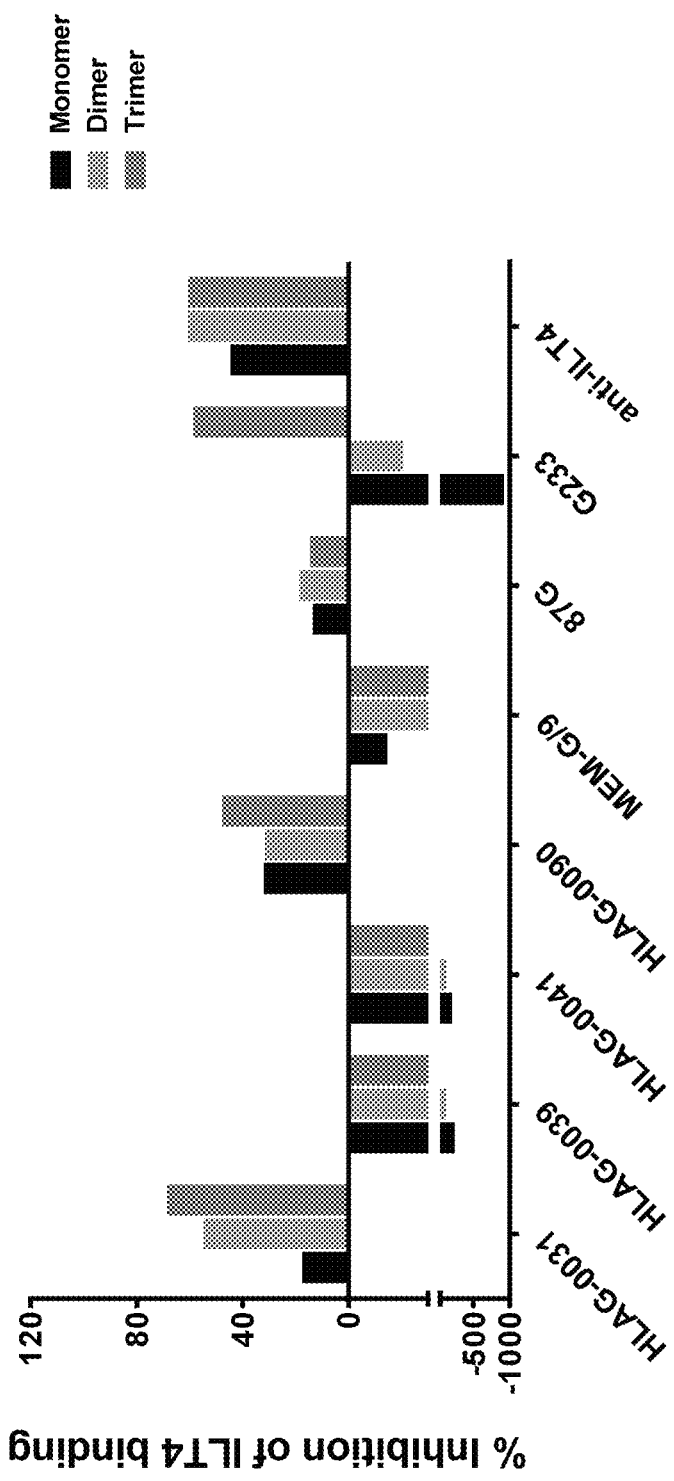

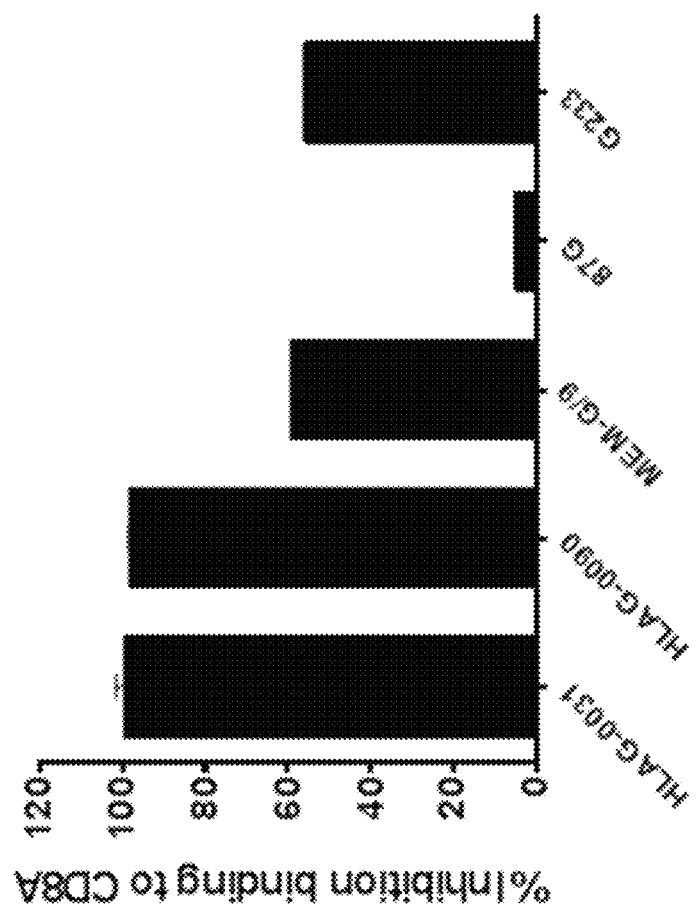

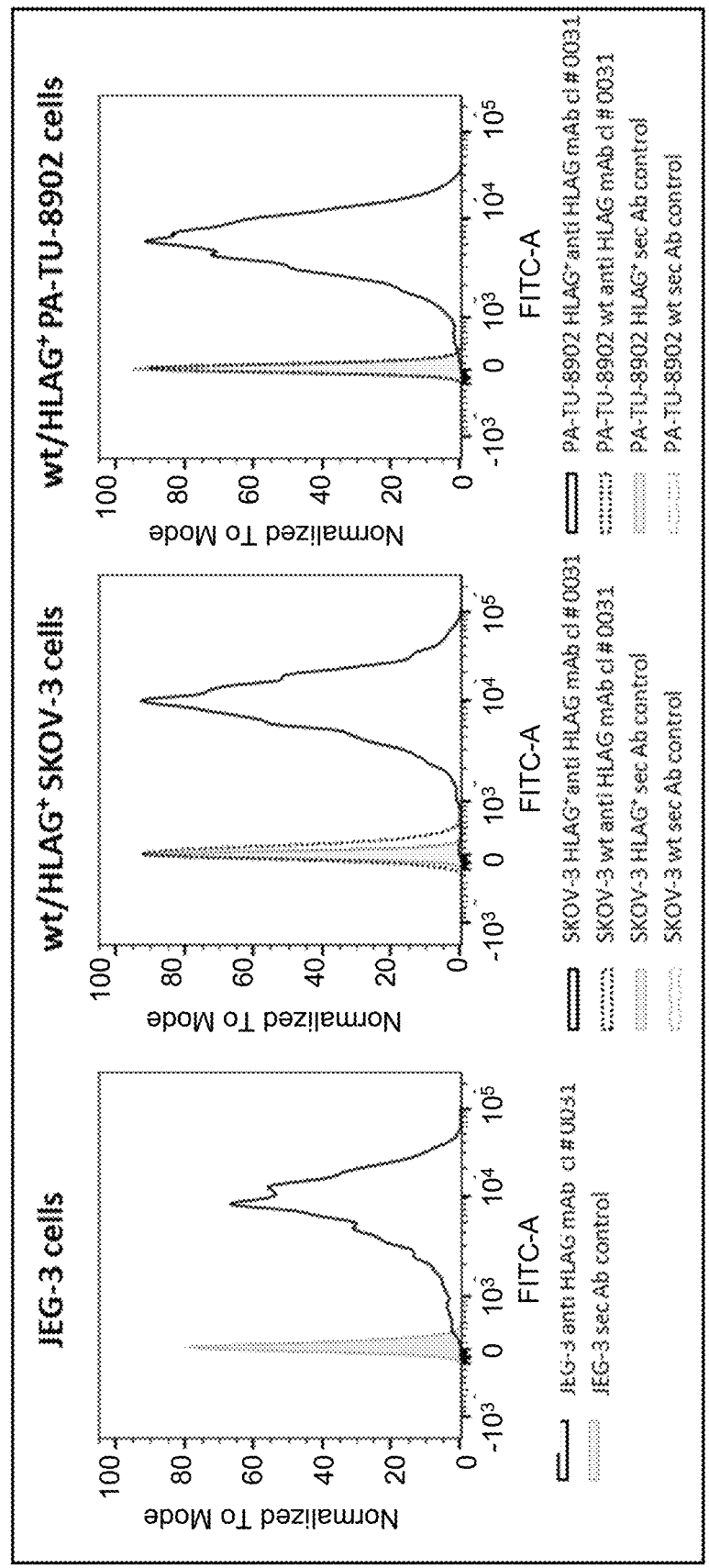

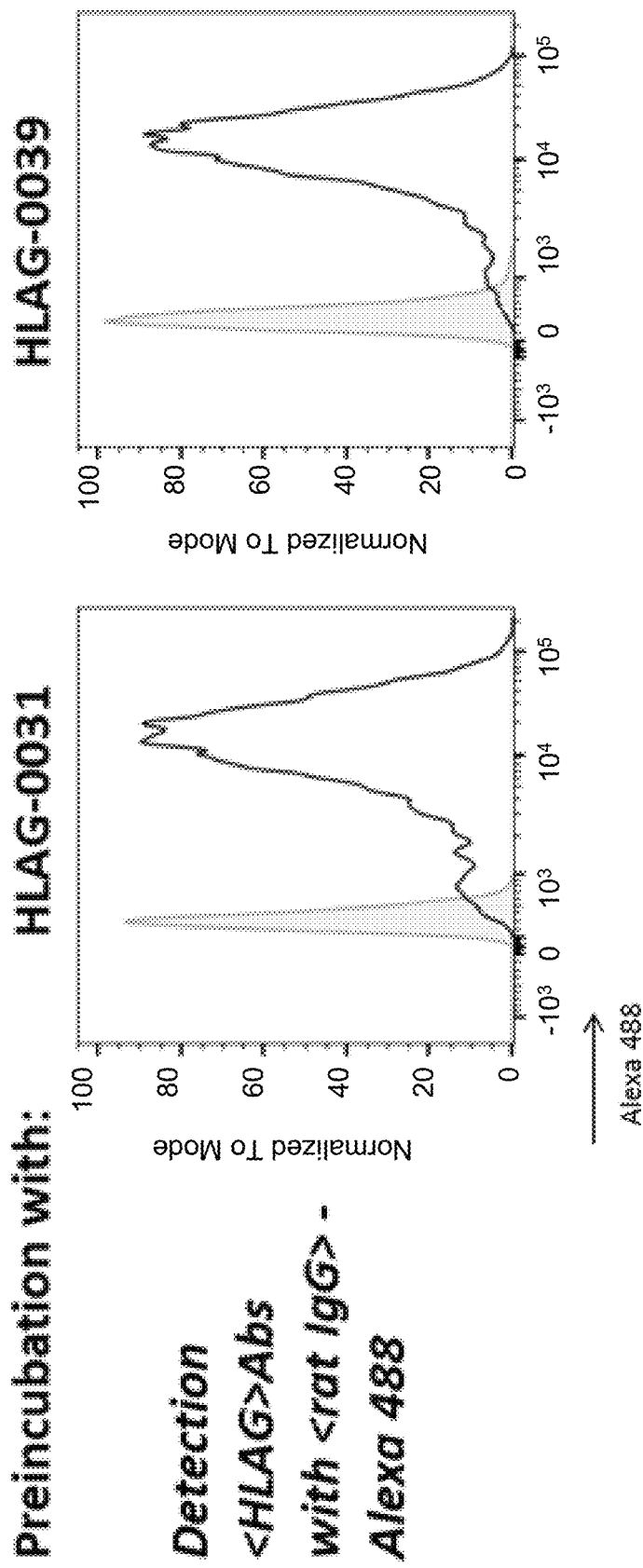

Fig. 5A(Con't)
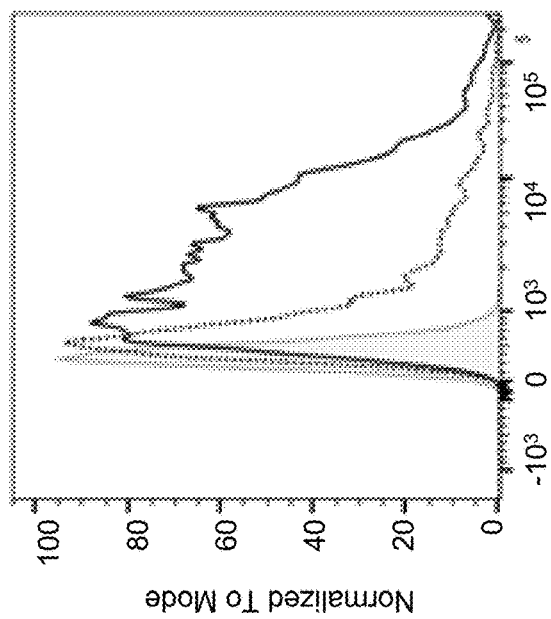
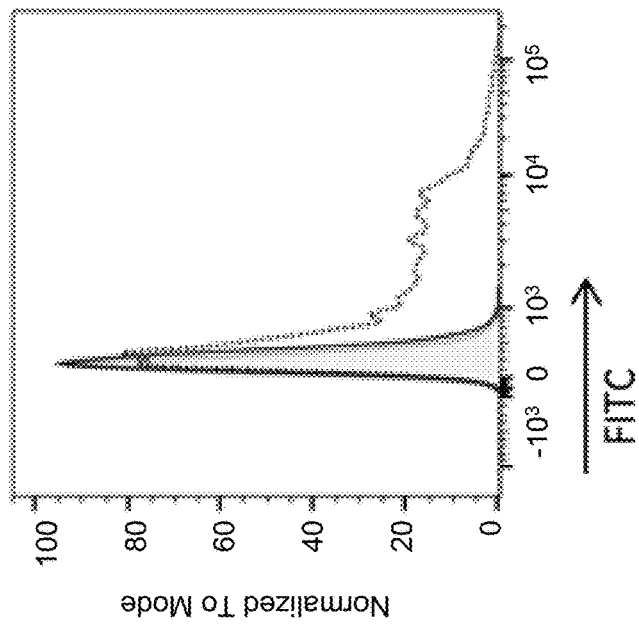
*Detection rec. IL-T2-Fc with anti huIgG Fc-spezif.-FITC*

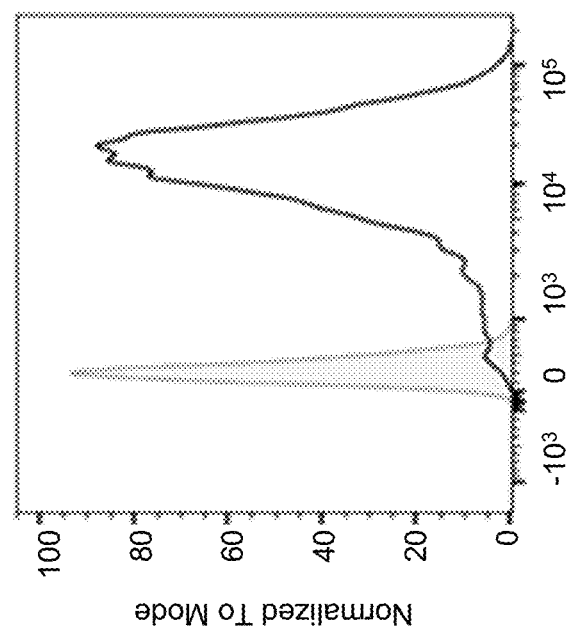
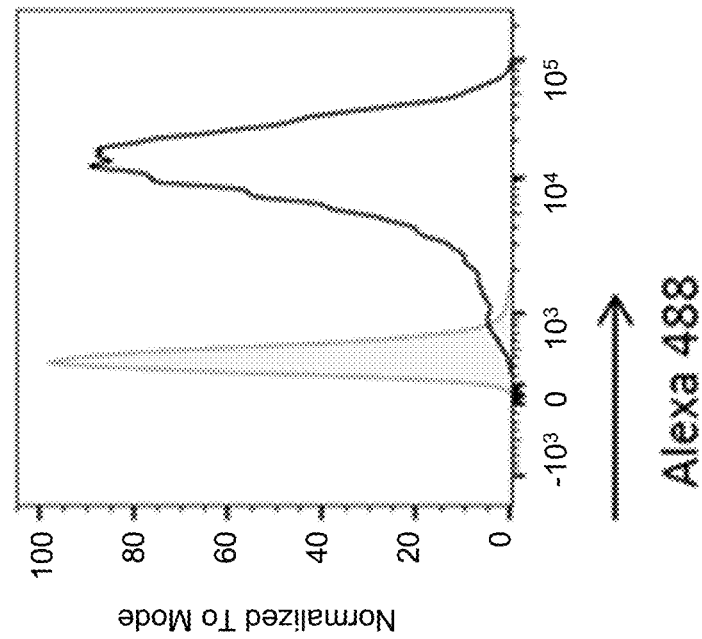
Fig. 5A(Con't)

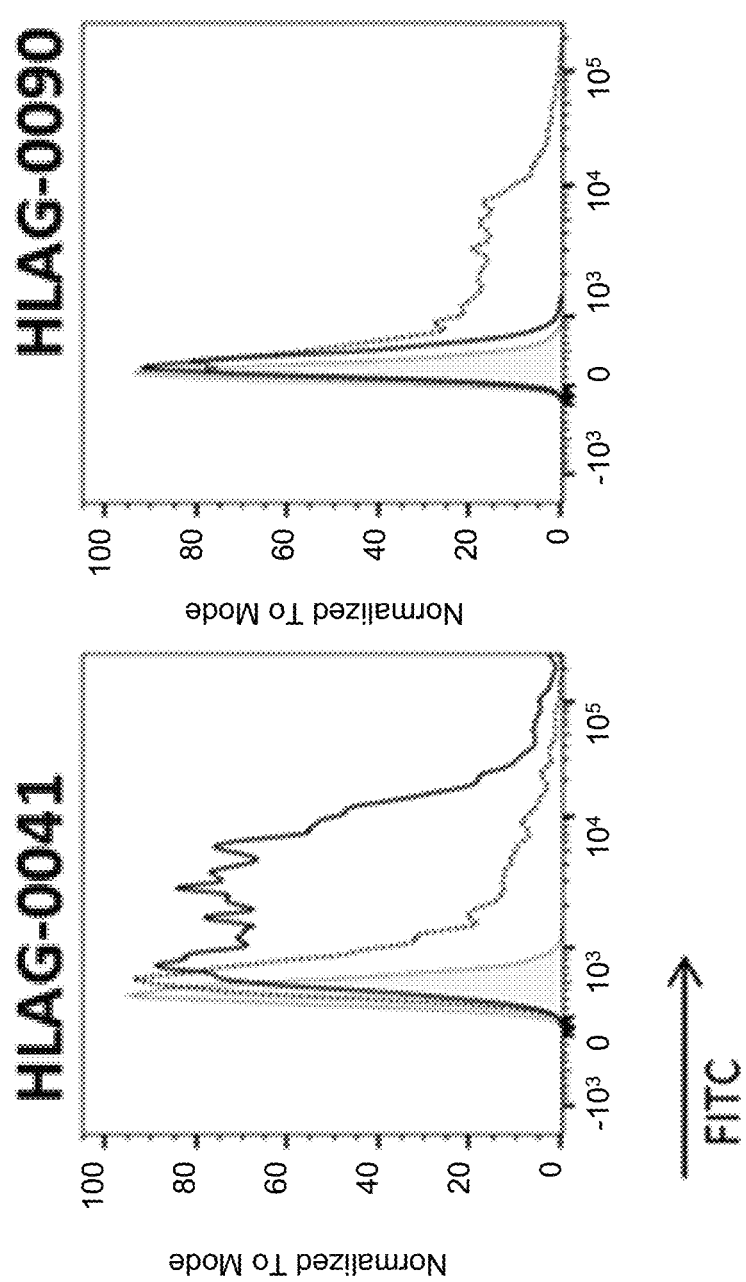

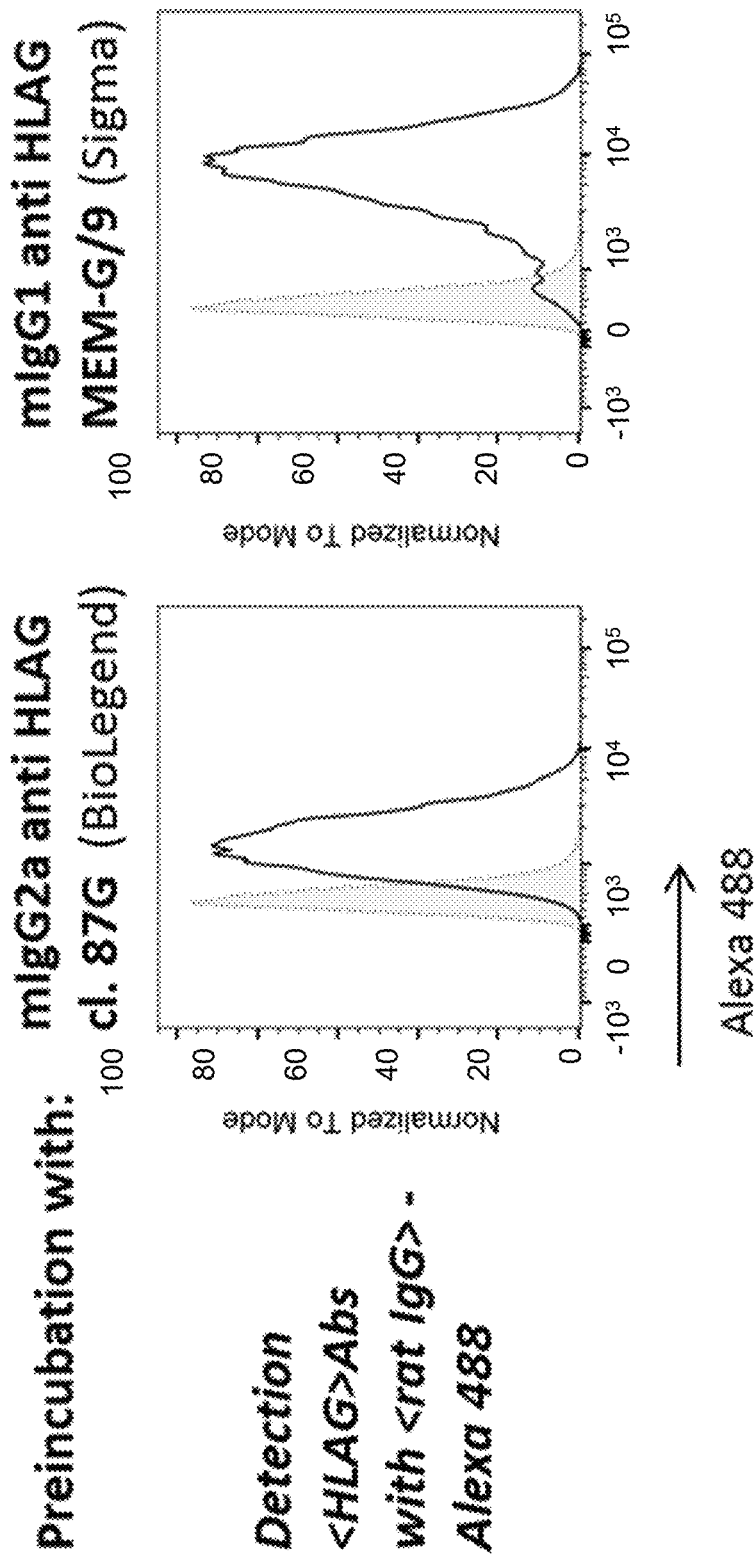

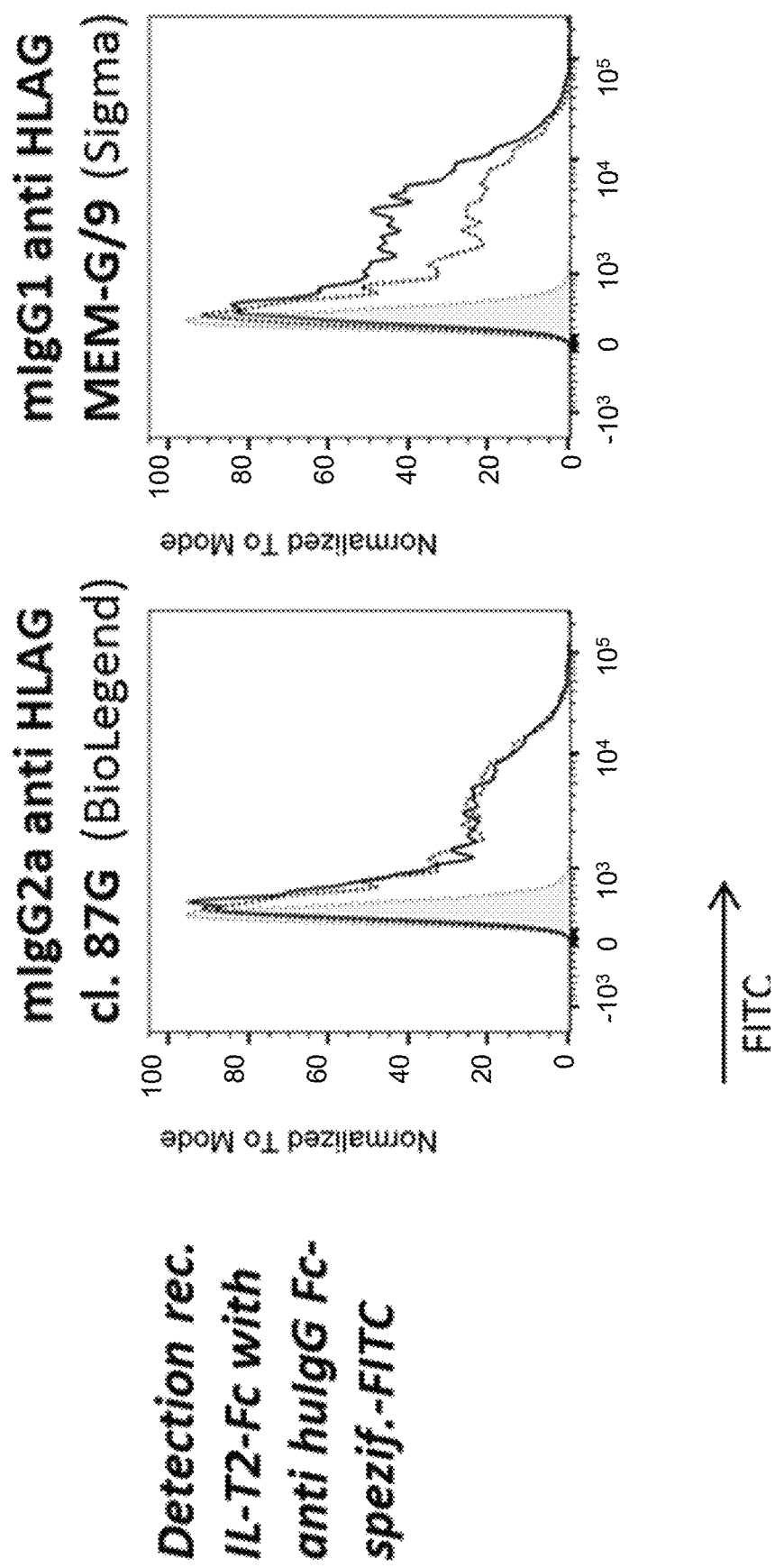

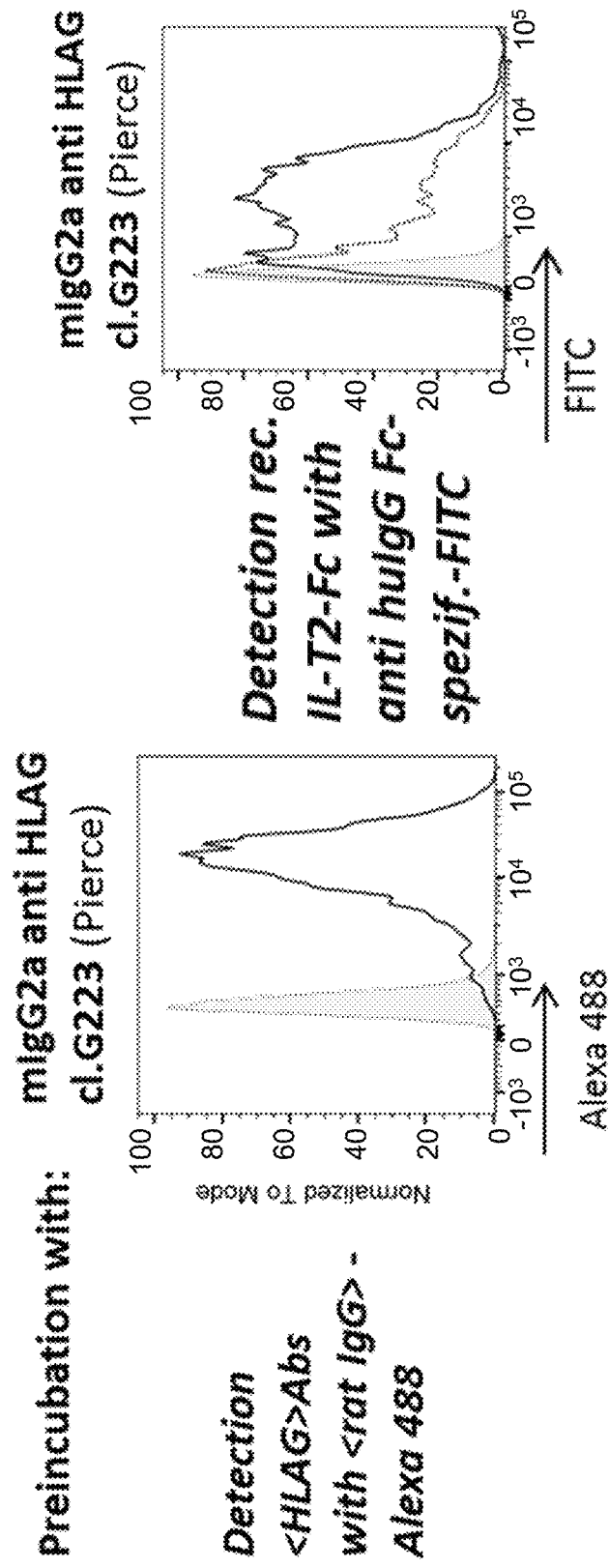
Fig. 5B (Con't)

ANTI-HLA-G ANTIBODIES AND METHODS OF USE THEREOF

CROSS-REFERENCE TO RELATED APPLICATIONS

This application is a continuation of International Application No. PCT/EP2019/060007, filed Apr. 17, 2019, which claims priority to European Patent Application No. EP18168011.7, filed Apr. 18, 2018, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Sep. 29, 2020, is named P34773-US_sequence_listing_ST25.txt and is 66.6 kilobytes in size.

FIELD OF THE INVENTION

The present invention relates to anti-HLA-G antibodies, their preparation, formulations and methods of using the same.

BACKGROUND OF THE INVENTION

The human major histocompatibility complex, class I, 6, also known as human leukocyte antigen G (HLA-G), is a protein that in humans is encoded by the HLA-G gene. HLA-G belongs to the HLA nonclassical class I heavy chain paralogues. This class I molecule is a heterodimer consisting of a heavy chain and a light chain (beta-2 microglobulin). The heavy chain is anchored in the membrane but can also be shedded/secreted.

The heavy chain consists of three domains: alpha 1, alpha 2 and alpha 3. The alpha 1 and alpha 2 domains form a peptide binding groove flanked by two alpha helices. Small peptides (approximately 9-mers) can bind to this groove akin to other MHC I proteins.

The second chain is beta 2 microglobulin which binds to the heavy chain similar to other MHC I proteins.

For HLA-G there exist 7 isoforms, 3 secreted and 4 membrane bound forms (as schematically shown in FIG. 1).

HLA-G can form functionally active complex oligomeric structures (Kuroki, K et al. Eur J Immunol. 37 (2007) 1727-1729). Disulfide-linked dimers are formed between Cys 42 of two HLA-G molecules. (Shiroishi M et al., J Biol Chem 281 (2006) 10439-10447. Trimers and Tetrameric complexes have also been described e.g., in Kuroki, K et al. Eur J Immunol. 37 (2007) 1727-1729, Allan D. S., et al. J Immunol Methods. 268 (2002) 43-50 and T Gonen-Gross et al., J Immunol 171 (2003)1343-1351).

HLA-G is predominantly expressed on cytotrophoblasts in the placenta. Several tumors (including pancreatic, breast, skin, colorectal, gastric & ovarian) express HLA-G (Lin, A. et al., Mol Med. 21 (2015) 782-791; Amiot, L., et al., Cell Mol Life Sci. 68 (2011) 417-431). The expression has also been reported to be associated with pathological conditions like inflammatory diseases, GvHD and cancer. Expression of HLA-G has been reported to be associated with poor prognosis in cancer. Tumor cells escape host immune surveillance by inducing immune tolerance/suppression via HLA-G expression.

| Overview polymorphisms HLA family | | |
|---|---|---|
| HLA-A: | 2579 seqs | classical class I MHC |
| HLA-B: | 3283 seqs | |
| HLA-C: | 2133 seqs | |
| HLA-E: | 15 seqs | non-classical class I MHC |
| HLA-F: | 22 seqs | |
| HLA-G: | 50 seqs | |

HLA-G shares high homology (>98%) with other MHC I molecules, therefore truly HLA-G specific antibodies with no crossreactivity to other MHC I molecules are difficult to generate.

Certain antibodies which interact in different ways with HLA-G were described previously: Tissue Antigens, 55 (2000) 510-518 relates to monoclonal antibodies e.g. 87G, and MEM-G/9; Neoplasma 50 (2003) 331-338 relates to certain monoclonal antibodies recognizing both, intact HLA-G oligomeric complex (e.g. 87G and MEM-G9) as well as HLA-G free heavy chain (e.g. 4H84, MEM-G/1 and MEM-G/2); Hum Immunol. 64 (2003) 315-326 relates to several antibodies tested on HLA-G expressing JEG3 tumor cells (e.g., MEM-G/09 and -G/13 which react exclusively with native HLA-G1 molecules. MEM-G/01 recognizes (similar to the 4H84 mAb) the denatured HLA-G heavy chain of all isoforms, whereas MEM-G/04 recognizes selectively denatured HLA-G1, -G2, and -G5 isoforms; Wiendl et al Brain 2003 176-85 relates to different monoclonal HLA-G antibodies as e.g., 87G, 4H84, MEM-G/9.

The above publications report antibodies, which bind to human HLA-G or the human HLA-G/ß2M MHC complex. However, due to the high polymorphism and high homology of the HLA family most of the antibodies lack either truly specific HLA-G binding properties and often also bind or crossreact with other HLA family members (either as MHC complex with ß2M or in its ß2M-free form) or they simply do not inhibit binding of HLA-G ß2M MHC complex to its receptors ILT2 and/or ILT4 (and are regarded as non-antagonistic antibodies).

Hence there is the need to generate and/or select further improved, truly HLA-G specific antibodies with receptor inhibition properties.

SUMMARY OF THE INVENTION

In one aspect, the invention provides an antibody that binds to human HLA-G (and that inhibits ILT2 binding to HLAG on JEG-3 cells (ATCC HTB36) and restores HLA-G specific suppressed TNF alpha release by monocytes co-cultured with JEG-3 cells.

One embodiment of the invention is an isolated antibody that binds to human HLA-G (in one embodiment the antibody binds to HLA-G ß2M MHC I complex comprising SEQ ID NO: 43), wherein the antibody comprises A) (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; or B) (a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14; or C) (a) a VH domain comprising (i) HVR-H1 comprising the amino acid sequence of SEQ ID NO:17, (ii) HVR-H2 comprising the amino acid sequence of SEQ ID NO:18, and (iii) HVR-H3 comprising an amino acid sequence selected from SEQ ID NO:19; and (b) a VL domain comprising (i) HVR-L1 comprising the amino acid sequence of SEQ ID NO:20; (ii) HVR-L2 comprising the amino acid sequence of SEQ ID NO:21 and (iii) HVR-L3 comprising the amino acid sequence of SEQ ID NO:22; or D) (a) a VH domain comprising (i) HVR-H1 comprising the amino acid sequence of SEQ ID NO:25, (ii) HVR-H2 comprising the amino acid sequence of SEQ ID NO:26, and (iii) HVR-H3 comprising an amino acid sequence selected from SEQ ID NO:27; and (b) a VL domain comprising (i) HVR-L1 comprising the amino acid sequence of SEQ ID NO:28; (ii) HVR-L2 comprising the amino acid sequence of SEQ ID NO:29 and (iii) HVR-L3 comprising the amino acid sequence of SEQ ID NO:30.

One embodiment of the invention is an isolated antibody that binds to human HLA-G (in one embodiment the antibody binds to HLA-G ß2M MHC I complex comprising SEQ ID NO: 43), wherein the antibody A)
  i) comprises a VH sequence of SEQ ID NO:7 and a VL sequence of SEQ ID NO:8;
  ii) or humanized variant of the VH and VL of the antibody under i); or
B)
  i) comprises a VH sequence of SEQ ID NO:15 and a VL sequence of SEQ ID NO:16;
  ii) or humanized variant of the VH and VL of the antibody under i); or
C)
  i) comprises a VH sequence of SEQ ID NO:23 and a VL sequence of SEQ ID NO:24;
  ii) or humanized variant of the VH and VL of the antibody under i); or
D)
  i) comprises a VH sequence of SEQ ID NO:31 and a VL sequence of SEQ ID NO:32;
  ii) or humanized variant of the VH and VL of the antibody under i).

In one embodiment the anti-HLA-G antibody described herein
  a) does not crossreact with a modified human HLA-G ß2M MHC I complex comprising SEQ ID NO:44; and/or
  b) does not crossreact with human HLA-A2 ß2M MHC I complex comprising SEQ ID NO:39 and SEQ ID NO:37; and/or
  c) does not crossreact with a mouse H2Kd ß2M MHC I complex comprising SEQ ID NO:45; and/or
  d) does not crossreact with rat RT1A ß2M MHC I complex comprising SEQ ID NO:47; and/or
  e) inhibits ILT2 binding to monomeric HLA-G ß2M MHC I complex (comprising SEQ ID NO: 43); and/or
  f) inhibits ILT2 binding to trimeric HLA-G ß2M MHC I complex (comprising SEQ ID NO: 43), by more than 50% (in one embodiment by more than 60%) (when compared to the binding without antibody) (see Example 4b); and/or
  g) inhibits ILT2 binding to monomeric and/or dimeric and/or trimeric HLA-G ß2M MHC I complex (comprising SEQ ID NO: 43), by more than 50% (in on embodiment by more than 80%) (when compared to the binding without antibody) (see Example 4b); and/or
  h) inhibits ILT2 binding to (HLA-G on) JEG3 cells (ATCC No. HTB36) (by more than 50% (in one embodiment by more than 80%)) (when compared to the binding without antibody) (see Example 6); and/or
  i) binds to (HLA-G on) JEG3 cells (ATCC No. HTB36) (see Example 5), and inhibits ILT2 binding to (HLA-G on) JEG3 cells (ATCC No. HTB36) (by more than 50% (in one embodiment by more than 80%)) (when compared to the binding without antibody) (see Example 6); and/or
  j) inhibits CD8a binding to HLAG by more than 80% (when compared to the binding without antibody) (see e.g., Example 4c).

In one embodiment the anti-HLA-G antibody is of IgG1 isotype.

In one embodiment the anti-HLA-G antibody is of IgG1 isotype with mutations L234A, L235A and P329G (numbering according to the EU index of Kabat).

In one preferred embodiment the anti-HLA-G antibody inhibits ILT2 binding to monomeric HLA-G ß2M MHC I complex.

In one embodiment the anti-HLA-G antibody according to the invention is a monoclonal antibody.

In one embodiment the anti-HLA-G antibody according to the invention is a human, humanized, or chimeric antibody.

In one embodiment the anti-HLA-G antibody according to the invention which is an antibody fragment that binds to HLA-G.

In one embodiment the anti-HLA-G antibody according to the invention which is Fab fragment.

The invention provides an isolated nucleic acid encoding the antibody according to any one of the preceding claims.

The invention provides a host cell comprising such nucleic acid.

The invention provides a method of producing an antibody comprising culturing the host cell so that the antibody is produced.

The invention provides such a method of producing an antibody, further comprising recovering the antibody from the host cell.

The invention provides a pharmaceutical formulation comprising the antibody described herein and a pharmaceutically acceptable carrier.

The invention provides the antibody described herein for use as a medicament.

The invention provides the antibody described herein for use in treating cancer.

The invention provides the use of the antibody described herein in the manufacture of a medicament. In one embodiment the medicament is for treatment of cancer.

The invention provides a method of treating an individual having cancer comprising administering to the individual an effective amount of the antibody described herein.

The present invention uses tailor-made chimeric antigens and/or stringent screening assays to identify HLA-G specific antibodies among numerous candidates (avoiding cross-reactivity to other MHC class I complex molecules and at the same time selecting HLA-G receptor (such as ILT2)

blocking antibodies) which show HLA-G-specific induction (restoration) of TNF alpha in co-cultures of HLA-G expressing JEG-3 cells and monocytes. With these screening methods described herein new anti-HLA-G antibodies could be selected. These antibodies show highly valuable properties like strong inhibition of ILT2 binding to HLA-G expressed on JEG3 cells or inhibition of ILT2 binding to monomeric and/or dimeric and/or trimeric HLA-G ß2M MHC I complex.

The invention provides antibodies that specifically binds to human HLA-G, inhibit ILT2 binding to HLAG, and restore an HLA-G specific suppressed immune response, restoration of Lipopolysaccharide (LPS)-induced TNFalpha production/secretion by monocytes in co-culture with HLA-G-expressing cells (as e.g., JEG-3 cells). The restoration of a truly HLA-G specific immune suppression of monocytes by HLA-G expressing cells like JEG-3 cells can be evaluated in comparison to JEG-3 cells with an HLA-G knockout.

Thus the antibodies of the invention restore an HLA-G specific release of TNF alpha in Lipopolysaccharide (LPS) stimulated co-cultures of HLA-G expressing JEG-3 cells and monocytes compared to untreated co-cultured JEG-3 cells (untreated cells are taken 0% negative reference; monocyte only cultures are taken as 100% positive reference, in which TNF alpha section is not suppressed by any HLA-G/IL-T2 specific effects (see Example 7)).

In addition, the antibodies are highly specific and do not show cross reactivity with HLA-A MHC I complexes or MHC I complexes from mouse or rat origin.

DESCRIPTION OF THE FIGURES

FIGS. 2A-2B: FIG. 2A: Schematic representation of HLA-G with molecule in association with ß2M FIG. 2B: Structure of HLA-G molecule in association with certain receptors: HLA-G structure in complex with given receptors such as ILT4 and KIR2DL1. ILT4 structure (PDB code: 2DYP). The KIR2DL1 structure is taken from PDB code 1IM9 (KIR2DL1: HLA-Cw4 complex structure) and was positioned on HLA-G by superposition of the HLA-Cw4 and HLA-G structures. Receptors are shown in a ribbon representation, HLA-G is shown in a molecular surface representation. HLA-G residues that are unique or conserved in other HLA paralogs are colored in white and gray, respectively. Unique surface residues were replaced by an HLA consensus sequence in the chimeric counter antigen.

FIGS. 3A-3C: HLA-G antibodies which inhibit (or stimulate) HLA-G interaction/binding with ILT2 and ILT4 as well as CD8:

FIG. 3A: ILT2 inhibition
FIG. 3B: ILT4 inhibition
FIG. 3C: CD8 inhibition

FIGS. 4A-4D: Flow cytometric analysis of cell surface expression of HLA-G using HLA-G antibodies on JEG3 (cells naturally expressing HLA-G), SKOV-3 cells (wild-type (wt) versus HLAG transfected cells (HLAG+)), and PA-TU-8902 cells (wild-type (wt) versus HLAG transfected cells (HLAG+)):

FIG. 4A: HLA-G-0031 (#0031); FIG. 4B: HLA-G-0039 (#0039);
FIG. 4C: HLA-G-0041 (#0041); FIG. 4D: HLA-G-0090 (#0090)

FIGS. 5A-5B: FIG. 5A: Anti-HLA-G antibodies (0031, 0039, 0041 and 0090) block/modulate interaction of human ILT2 Fc chimera with HLA-G expressed on JEG3 cells:

The staining of cell surface HLA-G with the novel anti-HLA-G antibodies was assessed by using an anti-rat IgG secondary antibody conjugated to ALEXA® 488 (upper row). Shown in the FACS histograms are cells stained with secondary antibody alone (grey dotted lines) and cells stained with anti-HLA-G antibodies (black solid lines). In the lower row human ILT2-Fc bound to HLA-G on JEG3 cells is depicted (black dotted line) in comparison to cells stained with secondary antibody alone (grey dotted line). The impact of pre-incubating JEG3 cells with HLA-G antibodies on ILT2 Fc chimera binding can been seen (black solid line): HLA-G-0031 and HLA-G-0090 showed nearly complete inhibition of binding of ILT2-Fc chimera to JEG3 cells. Interestingly, the two antibodies 0039 and 0041 even increase ILT2:fc binding to the cells.

FIG. 5B: Impact of commercial/reference anti-HLA-G antibodies on ILT2 Fc chimera binding to HLA-G on JEG3 cells.

The staining of cell surface HLA-G with commercial/reference anti-HLA-G antibodies was assessed by using a species-specific secondary antibody conjugated to ALEXA® 488 (upper row). Shown in the FACS histograms are cells stained with secondary antibody alone (grey dotted lines) and cells stained with anti-HLA-G antibodies (black solid lines). In the lower row human ILT2 Fc chimera bound to HLA-G on JEG3 cells is depicted (black dotted line) in comparison to cells stained with secondary antibody alone (grey dotted line). The impact of pre-incubating JEG3 cells with reference antibodies on ILT2 Fc chimera binding can been seen (black solid line). None of the tested reference antibodies could block the interaction of ILT2 Fc chimera with cell surface HLA-G on JEG3 cells.

Figure 6A:
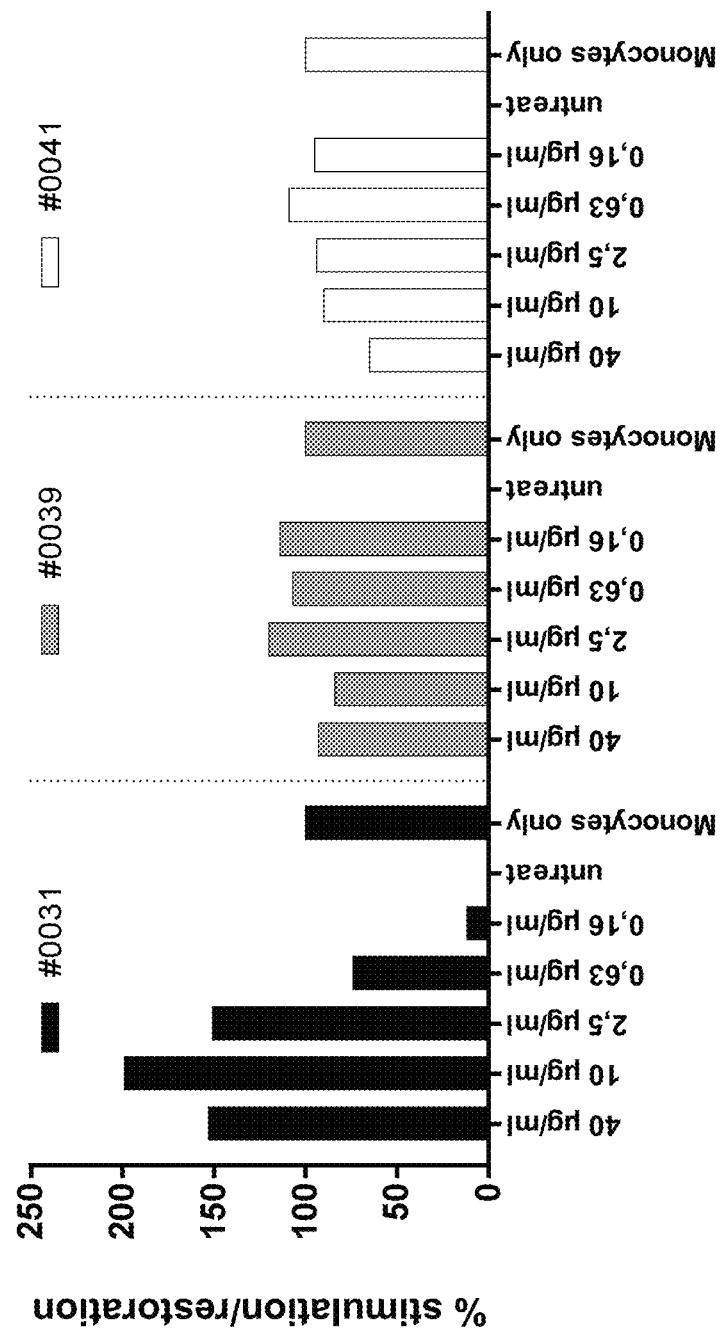
Figure 6B:
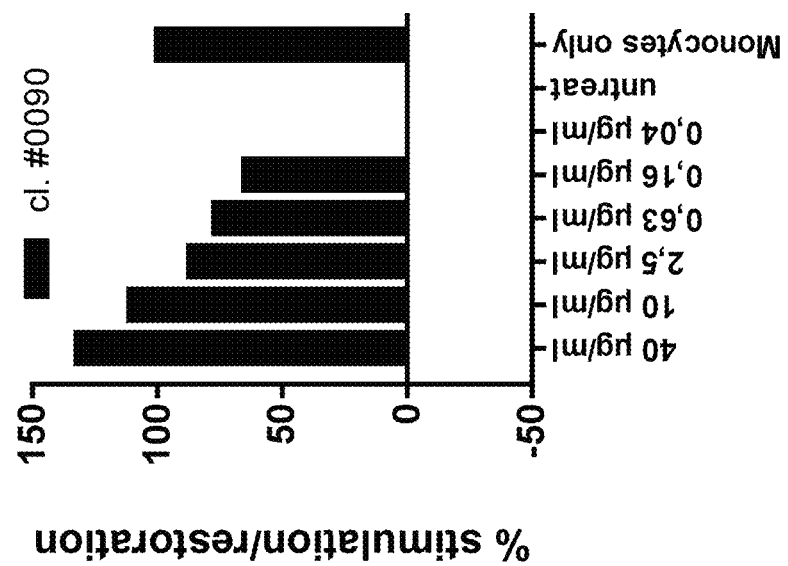
Figure 6C:
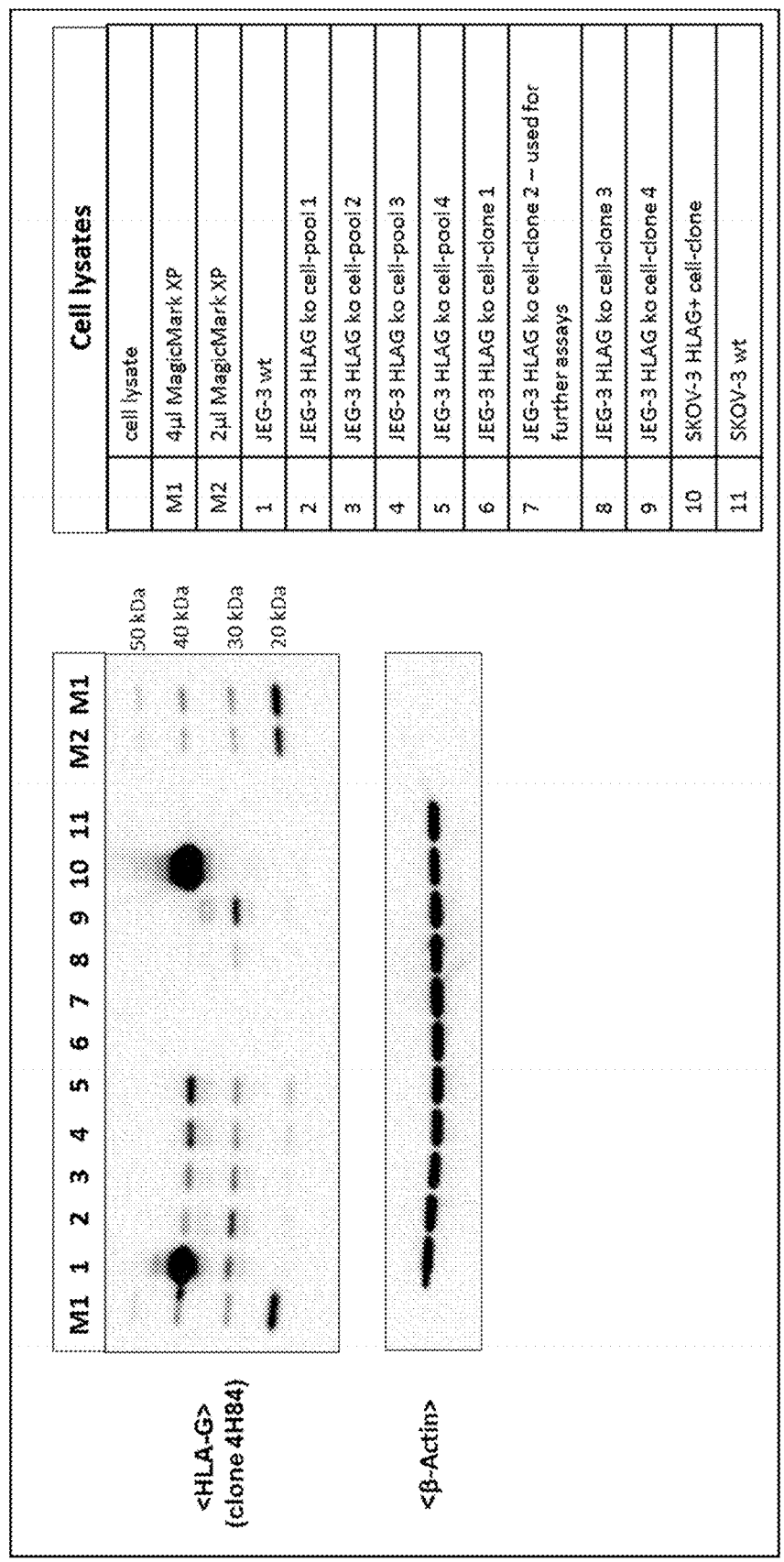

FIGS. 6A-6C: The impact of the blockade of HLA-G with inhibitory anti-HLA-G antibodies on the restoration of TNFα production assessed on different donors.

FIG. 6A: Anti-HLAG antibodies HLA-G-0031 (#0031), HLA-G-0039 (#0039), and HLA-G-0041 (#0041) evaluated on a representative monocyte donor.

FIG. 6B: Anti-HLAG antibody HLA-G-0090 (#0090)] evaluated on a different monocyte donor.

FIG. 6C: Western blot analysis of HLAG expression in wt JEG-3 cells and knock down variants.

DETAILED DESCRIPTION OF THE INVENTION

When used herein, the terms "HLA-G" and "human HLA-G", refer to the HLA-G human major histocompatibility complex, class I, G, also known as human leukocyte antigen G (HLA-G) (exemplary SEQ ID NO: 35). Typically, HLA-G forms an MHC class I complex together with β2 microglobulin (b2M or β2m). In one embodiment HLA-G refers to the MHC class I complex of HLA-G and β2 microglobulin.

As used herein, an antibody "binding to human HLA-G", "specifically binding to human HLA-G", "that binds to human HLA-G" or "anti-HLA-G antibody" refers to an antibody specifically binding to the human HLA-G antigen or its extracellular domain (ECD) with a binding affinity of a $K_D$-value of $5.0 \times 10^{-8}$ mol/l or lower, in one embodiment of a $K_D$-value of $1.0 \times 10^{-9}$ mol/l or lower, in one embodiment of a $K_D$-value of $5.0 \times 10^{-8}$ mol/l to $1.0 \times 10^{-13}$ mol/l. In one embodiment the antibody binds to HLA-G ß2M MHC I complex comprising SEQ ID NO: 43).

The binding affinity is determined with a standard binding assay, such as surface plasmon resonance technique (BIAcore®, GE-Healthcare Uppsala, Sweden) e.g., using constructs comprising HLA-G extracellular domain (e.g., in its natural occurring three-dimensional structure). In one embodiment binding affinity is determined with a standard binding assay using exemplary soluble HLA-G comprising MHC class I complex comprising SEQ ID NO: 43.

HLA-G has the regular MHC I fold and consists of two chains: Chain 1 consists of three domains: alpha 1, alpha 2 and alpha 3. The alpha 1 and alpha 2 domains form a peptide binding groove flanked by two alpha helices. Small peptides (approximately 9mers) can bind to this groove akin to other MHCI proteins. Chain 2 is beta 2 microglobulin which is shared with various other MHCI proteins.

HLA-G can form functionally active complex oligomeric structures (Kuroki, K et al. Eur J Immunol. 37 (2007) 1727-1729). Disulfide-linked dimers are formed between Cys 42 of two HLA-G molecules. (Shiroishi M et al., J Biol Chem 281 (2006) 10439-10447. Trimers and Tetrameric complexes have also been described e.g., in Kuroki, K et al. Eur J Immunol. 37 (2007) 1727-1729, Allan D. S., et al. J Immunol Methods. 268 (2002) 43-50 and T Gonen-Gross et al., J Immunol 171 (2003)1343-1351). HLA-G has several free cysteine residues, unlike most of the other MHC class I molecules. Boyson et al., Proc Nat Acad Sci USA, 99: 16180 (2002) reported that the recombinant soluble form of HLA-G5 could form a disulfide-linked dimer with the intermolecular Cys42-Cys42 disulfide bond. In addition, the membrane-bound form of HLA-G1 can also form a disulfide-linked dimer on the cell surface of the Jeg3 cell line, which endogenously expresses HLA-G. Disulfide-linked dimer forms of HLA-G1 and HLA-G5 have been found on the cell surface of trophoblast cells as well (Apps, R., Tissue Antigens, 68:359 (2006)).

HLA-G is predominantly expressed on cytotrophoblasts in the placenta. Several tumors (including pancreatic, breast, skin, colorectal, gastric & ovarian) express HLA-G (Lin, A. et al., Mol Med. 21 (2015) 782-791; Amiot, L., et al., Cell Mol Life Sci. 68 (2011) 417-431). The expression has also been reported to be associated with pathological conditions like inflammatory diseases, GvHD and cancer. Expression of HLA-G has been reported to be associated with poor prognosis in cancer. Tumor cells escape host immune surveillance by inducing immune tolerance/suppression via HLA-G expression.

Figure 1:
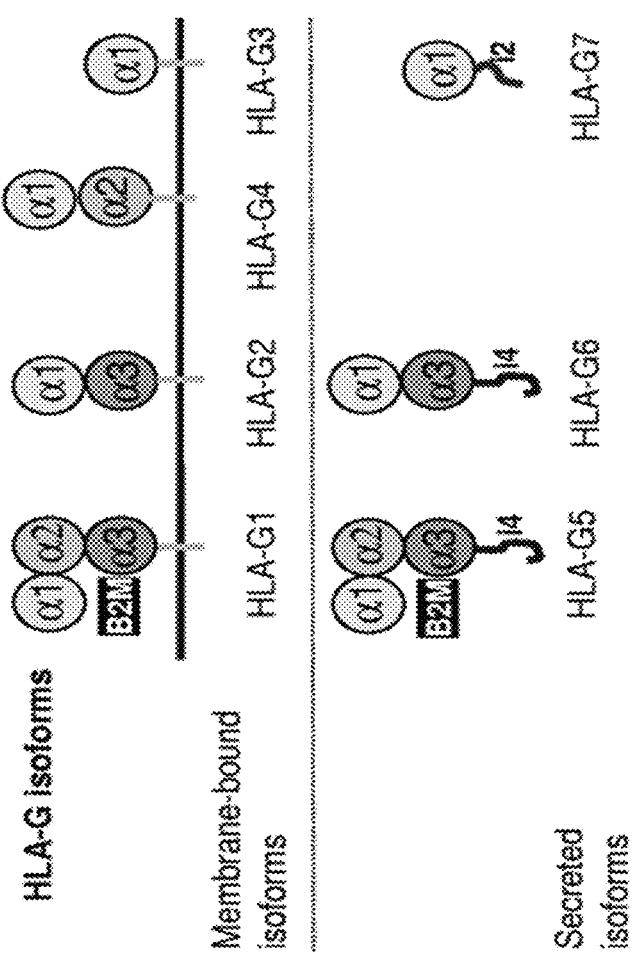
FIG. 1: Different isoforms of HLA-G
Figure 2B:
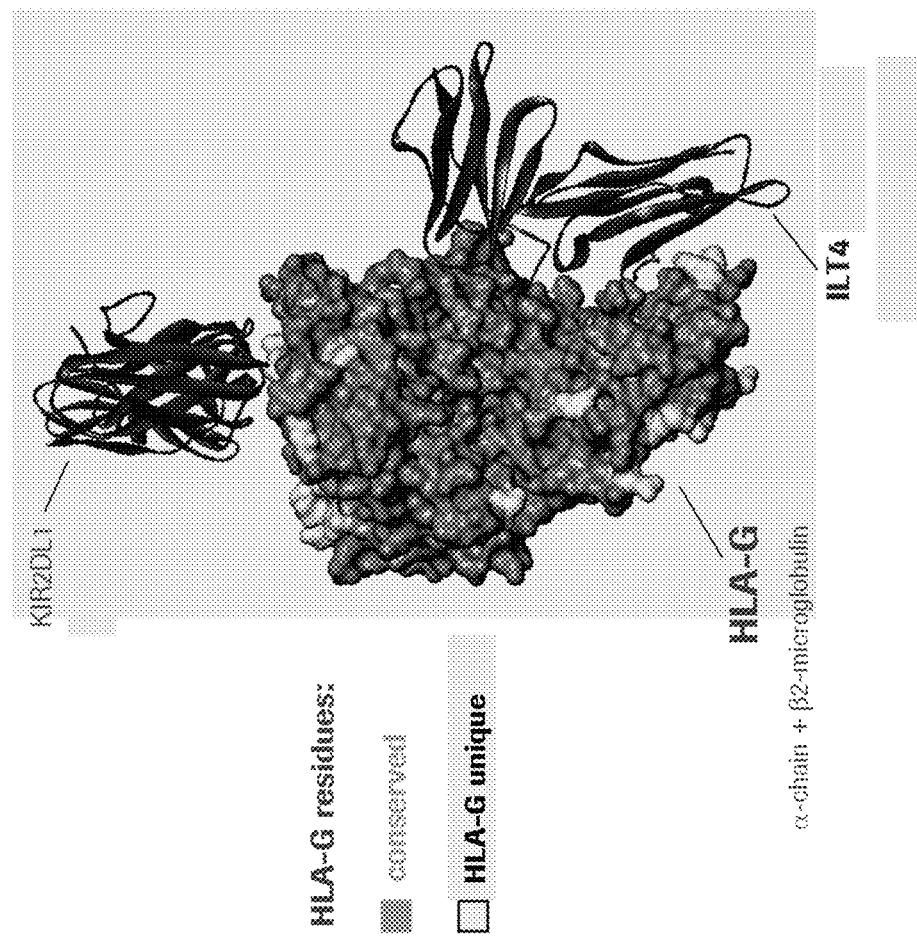

For HLA-G there exist 7 isoforms, 3 secreted and 4 membrane bound forms (as schematically shown in FIG. 1). The most important functional isoforms of HLA-G include b2-microglobulin-associated HLA-G1 and HLA-G5. However, the tolerogenic immunological effect of these isoforms is different and is dependent on the form (monomer, dimer) of ligands and the affinity of the ligand-receptor interaction.

HLA-G protein can be produced using standard molecular biology techniques. The nucleic acid sequence for HLA-G isoforms is known in the art. See for example GENBANK Accession No. AY359818.

The HLA-G isomeric forms promote signal transduction through ILTs, in particular ILT2, ILT4, or a combination thereof.

ILTs: ILTs represent Ig types of activating and inhibitory receptors that are involved in regulation of immune cell activation and control the function of immune cells (Borges, L., et al., Curr Top Microbial Immunol, 244:123-136 (1999)). ILTs are categorized into three groups: (i) inhibitory, those containing a cytoplasmic immunoreceptor tyrosine-based inhibitory motif (ITIM) and transducing an inhibitory signal (ILT2, ILT3, ILT4, ILT5, and LIR8); (ii) activating, those containing a short cytoplasmic tail and a charged amino acid residue in the transmembrane domain (ILT1, ILT7, ILT8, and LIR6alpha) and delivering an activating signal through the cytoplasmic immunoreceptor tyrosine-based activating motif (ITAM) of the associated common gamma chain of Fc receptor; and (iii) the soluble molecule ILT6 lacking the transmembrane domain. A number of recent studies have highlighted immunoregulatory roles for ILTs on the surface of antigen presenting cells (APC). ILT2, ILT3, and ILT4 receptors, the most characterized immune inhibitory receptors, are expressed predominantly on myeloid and plasmacytoid DC. ILT3 and ILT4 are upregulated by exposing immature DC to known immunosuppressive factors, including IL-10, vitamin D3, or suppressor CD8 T cells (Chang, C. C., et al., Nat Immunol, 3:237-243 (2002)). The expression of ILTs on DC is tightly controlled by inflammatory stimuli, cytokines, and growth factors, and is down-regulated following DC activation (Ju, X. S., et al., Gene, 331:159-164 (2004)). The expression of ILT2 and ILT4 receptors is highly regulated by histone acetylation, which contributes to strictly controlled gene expression exclusively in the myeloid lineage of cells (Nakajima, H., J Immunol, 171:6611-6620 (2003)).

Engagement of the inhibitory receptors ILT2 and ILT4 alters the cytokine and chemokine secretion/release profile of monocytes and can inhibit Fc receptor signaling (Colonna, M., et al. J Leukoc Biol, 66:375-381 (1999)). The role and function of ILT3 on DC have been precisely described by the Suciu-Foca group (Suciu-Foca, N., Int Immunopharmacol, 5:7-11 (2005)). Although the ligand for ILT3 is unknown, ILT4 is known to bind to the third domain of HLA class I molecules (HLA-A, HLA-B, HLA-C, and HLA-G), competing with CD8 for MHC class I binding (Shiroishi, M., Proc Natl Acad Sci USA, 100:8856-8861 (2003)). The preferential ligand for several inhibitory ILT receptors is HLA-G. HLA-G plays a potential role in maternal-fetal tolerance and in the mechanisms of escape of tumor cells from immune recognition and destruction (Hunt, J. S., et al., Faseb J, 19:681-693 (2005)). It is most likely that regulation of DC function by HLA-G-ILT interactions is an important pathway in the biology of DC. It has been determined that human monocyte-derived DC that highly express ILT2 and ILT4 receptors, when treated with HLA-G and stimulated with allogeneic T cells, still maintain a stable tolerogenic-like phenotype (CD80low, CD86low, HLA-DRlow) with the potential to induce T cell anergy (Ristich, V., et al., Eur J Immunol, 35:1133-1142 (2005)). Moreover, the HLA-G interaction with DC that highly express ILT2 and ILT4 receptors resulted in down-regulation of several genes involved in the MHC class II presentation pathway. A lysosomal thiol reductase, IFN-gamma inducible lysosomal thiol reductase (GILT), abundantly expressed by professional APC, was greatly reduced in HLA-G-modified DC. The repertoire of primed CD4+ T cells can be influenced by DC expression of GILT, as in vivo T cell responses to select antigens were reduced in animals lacking GILT after targeted gene disruption (Marie, M., et al., Science, 294:1361-1365 (2001)). The HLA-G/ILT interaction on DC interferes with the assembly and transport of MHC class II molecules to the cell surface, which might result in less efficient presentation or expression of structurally abnormal MHC class II molecules. It was determined that HLA-G markedly decreased the transcription of invariant chain (CD74), HLA-DMA, and HLA-DMB genes on human monocyte-derived DC highly expressing ILT inhibitory receptors (Ristich, V., et al; Eur J Immunol 35:1133-1142 (2005)).

Another receptor of HLA-G is KIR2DL4 because KIR2DL4 binds to cells expressing HLA-G (US2003232051; Cantoni, C. et al. Eur J Immunol 28 (1998) 1980; Rajagopalan, S. and E. O. Long. [published erratum appears in J Exp Med 191 (2000) 2027] J Exp Med 189 (1999) 1093; Ponte, M. et al. PNAS USA 96 (1999) 5674). KIR2DL4 (also referred to as 2DL4) is a KIR family member (also designated CD158d) that shares structural features with both activating and inhibitory receptors (Selvakumar, A. et al. Tissue Antigens 48 (1996) 285). 2DL4 has a cytoplasmic ITIM, suggesting inhibitory function, and a positively charged amino acid in the transmembrane region, a feature typical of activating KIR. Unlike other clonally distributed KIRs, 2DL4 is transcribed by all NK cells (Valiante, N. M. et al. Immunity 7 (1997) 739; Cantoni, C. et al. Eur J Immunol 28 (1998) 1980; Rajagopalan, S. and E. O. Long. [published erratum appears in J Exp Med 191 (2000) 2027] J Exp Med 189 (1999) 1093).

HLA-G has also been shown to interact with CD8 (Sanders et al, J. Exp. Med., 1991) on cytotoxic T cells and induce CD95 mediated apoptosis in activated CD8 positive cytotoxic T cells (Fournel et al, J. Immun., 2000). This mechanism of elimination of cytotoxic T cells has been reported to be one of the mechanisms of immune escape and induction of tolerance in pregnancy, inflammatory diseases and cancer (Amodio G. et al, Tissue Antigens, 2014).

As used herein an anti-HLA-G antibody that "does not crossreact with" or that "does not specifically bind to" a modified human HLA-G ß2M MHC I complex comprising SEQ ID NO:44; a mouse H2Kd ß2M MHC I complex comprising SEQ ID NO:45 rat RT1A ß2M MHC I complex comprising SEQ ID NO:47, human HLA-A2 ß2M MHC I complex comprising SEQ ID NO:39 and SEQ ID NO: 37 refers to an anti-HLA-G antibody that does substantially not bind to any of these counterantigens. In one embodiment an anti-HLA-G antibody that "does not crossreact with" or that "does not specifically bind to" a modified human HLA-G ß2M MHC I complex comprising SEQ ID NO:44; a mouse H2Kd ß2M MHC I complex comprising SEQ ID NO:45, a rat RT1A ß2M MHC I complex comprising SEQ ID NO:47, and/or a human HLA-A2 ß2M MHC I complex comprising SEQ ID NO:39 and SEQ ID NO: 37 refers to an anti-HLA-G antibody that shows only unspecific binding with a binding affinity of a $K_D$-value of $5.0 \times 10^{-6}$ mol/l or higher (until no more binding affinity is detectable). The binding affinity is determined with a standard binding assay, such as surface plasmon resonance technique (BIAcore®, GE-Healthcare Uppsala, Sweden) with the respective antigen: a modified human HLA-G ß2M MHC I complex comprising SEQ ID NO:44; a mouse H2Kd ß2M MHC I complex comprising SEQ ID NO:45 rat RT1A ß2M MHC I complex comprising SEQ ID NO:47, and/or a human HLA-A2 ß2M MHC I complex comprising SEQ ID NO:39 and SEQ ID NO: 37 The assay setup as well as the construction/preparation of the antigens is described in the Examples.

The term "inhibits ILT2 binding to HLAG on JEG-3 cells (ATCC HTB36)" refers to the inhibition of binding interaction of recombinant ILT2 in an assay as described e.g., in Example 6.

The terms "restoration of HLA-G specific suppressed immune response" or to "restore HLA-G specific suppressed immune response" refers to a restoration of Lipopolysaccharide (LPS)-induced TNFalpha production by monocytes in co-culture with HLA-G-expressing cells in particular JEG-3 cells. Thus the antibodies of the invention restore an HLAG specific release of TNF alpha in Lipopolysaccharide (LPS) stimulated co-cultures of HLA-G expressing JEG-3 cells (ATCC HTB36) and monocytes compared to untreated co-cultured JEG-3 cells (untreated co-cultures are taken 0% negative reference; monocyte only cultures are taken as 100% positive reference, in which TNF alpha section is not suppressed by any HLA-G/IL-T2 specific effects (see Example 7). In this context "HLA-G specific suppressed immune response" refers to an immune suppression of monocytes due to the HLA-G expression on JEG-3 cells. In contrast, the anti-HLA-G antibodies of the present invention are not able to restore the immune response by monocytes co-cultured with JEG3 cell with an HLA-G knock out. As other commercial anti-HLA-Gs are able to induce TNF alpha by monocytes co-cultured with JEG3 cell with an HLA-G knock out, these antibodies, there is a non-HLA-G specific TNF alpha release by these antibodies.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence. A preferred VH acceptor human framework for a humanized variant of the obtained antibody HLAG-0031 is HUMAN_IGHV1-3. A preferred VL acceptor human framework for a humanized variant of the obtained antibody HLAG-0031 are HUMAN_IGKV1-17 (V-domain, with one additional back-mutation at position R46F, Kabat numbering).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA₁, and IgA₂. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, ADRIAMYCIN®, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447), or the C-terminal glycine (Gly446) and the C-terminal lysine (Lys447), of the Fc region may or may not be present. In one embodiment the anti-HLA-G antibody as described herein is of IgG1 isotype and comprises a constant heavy chain domain of SEQ ID NO: 53 or of SEQ ID NO: 54. In one embodiment it comprises additionally the C-terminal glycine (Gly446). In one embodiment it comprises additionally the C-terminal glycine (Gly446) and the C-terminal lysine (Lys447). In one embodiment the anti-HLA-G antibody as described herein is of IgG4 isotype and comprises and constant heavy chain domain of SEQ ID NO: 55. In one embodiment it comprises additionally the C-terminal glycine (Gly446). In one embodiment it comprises additionally the C-terminal glycine (Gly446) and the C-terminal lysine (Lys447). Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
  (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
  (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));
  (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and
  (d) combinations of (a), (b), and/or (c), including HVR amino acid residues 24-34 (L1), 50-56 (L2), 89-97 (L3), 31-35 (H1), 50-63 (H2), and 95-102 (H3).

Unless otherwise indicated, HVR residues and other residues in the variable domain (e.g., FR residues) are numbered herein according to Kabat et al., Kabat et al.,

*Sequences of Proteins of Immunological Interest*, 5th Ed. Public Health Service, National Institutes of Health, Bethesda, Md. (1991).

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-HLA-G antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See e.g., Portolano, S. et al., J. Immunol. 150 (1993) 880-887; Clackson, T. et al., Nature 352 (1991) 624-628).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

I. Compositions and Methods

In one aspect, the invention is based, in part, on the finding that the selected anti-HLA-G antibodies of the invention bind to certain epitopes of HLA-G with high specificity (no crossreactivity with other species and human HLA-A consensus sequences), and have ability to specifically inhibit ILT2 and or ILT4 binding to HLA-G. They inhibit e.g. ILT2 binding to HLA-G and revert specifically HLA-G mediated immune suppression by increased release of immunomodulatory cytokines like TNF alpha upon appropriate stimulation, and show no effect on HLAG knockout cells.

In certain embodiments, antibodies that bind to HLA-G are provided. Antibodies of the invention are useful, e.g., for the diagnosis or treatment of cancer.

A. Exemplary Anti-HLA-G Antibodies

In one aspect, the invention provides an (isolated) antibody that binds to human HLA-G (anti-HLA-G antibody) and that inhibits ILT2 binding to HLAG on JEG-3 cells (ATCC HTB36) and restores HLA-G specific suppressed immune response (e.g., suppressed Tumor necrose factor (TNF) alpha release) by monocytes co-cultured with JEG-3 cells (ATCC HTB36). Thus the antibodies of the invention restore an HLAG specific release of TNF alpha in Lipopolysaccharide (LPS) stimulated co-cultures of HLA-G expressing JEG-3 cells (ATCC HTB36) and monocytes compared to untreated co-cultured JEG-3 cells (untreated co-cultures are taken 0% negative reference; monocyte only cultures are taken as 100% positive reference, in which TNF alpha section is not suppressed by any HLA-G/IL-T2 specific effects ((see Example 7). In contrast, the antibodies of the present invention are not able to restore the immune response by monocytes co-cultured with JEG3 cell with an HLA-G knock out.

One embodiment of the invention is an (isolated) antibody that binds to human HLA-G (in one embodiment the antibody binds to HLA-G ß2M MHC I complex comprising SEQ ID NO: 43), wherein the antibody comprises A) (a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6; or B) (a) HVR-H1 comprising the amino acid sequence of SEQ ID NO:9; (b) HVR-H2 comprising the amino acid sequence of SEQ ID NO:10; (c) HVR-H3 comprising the amino acid sequence of SEQ ID NO:11; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14; or C) (a) HVR-H1 comprising the amino acid sequence of SEQ ID NO:17; (b) HVR-H2 comprising the amino acid sequence of SEQ ID NO:18; (c) HVR-H3 comprising the amino acid sequence of SEQ ID NO:19; (d) HVR-L1 comprising the amino acid sequence of SEQ ID NO:20; (e) HVR-L2 comprising the amino acid sequence of SEQ ID NO:21; and (f) HVR-L3 comprising the amino acid sequence of SEQ ID NO:22; or D) (a) HVR-H1 comprising the amino acid sequence of SEQ ID NO:25; (b) HVR-H2 comprising the amino acid sequence of SEQ ID NO:26; (c) HVR-H3 comprising the amino acid sequence of SEQ ID NO:27; (d) HVR-L1 comprising the amino acid sequence of SEQ ID NO:28; (e) HVR-L2 comprising the amino acid sequence of SEQ ID NO:29; and (f) HVR-L3 comprising the amino acid sequence of SEQ ID NO:30.

One embodiment of the invention is an (isolated) antibody that binds to human HLA-G (in one embodiment the antibody binds to HLA-G ß2M MHC I complex comprising SEQ ID NO: 43), wherein the antibody comprises A) (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; or B) (a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14; or C) (a) a VH domain comprising (i) HVR-H1 comprising the amino acid sequence of SEQ ID NO:17, (ii) HVR-H2 comprising the amino acid sequence of SEQ ID NO:18, and (iii) HVR-H3 comprising an amino acid sequence selected from SEQ ID NO:19; and (b) a VL domain comprising (i) HVR-L1 comprising the amino acid sequence of SEQ ID NO:20; (ii) HVR-L2 comprising the amino acid sequence of SEQ ID NO:21 and (iii) HVR-L3 comprising the amino acid sequence of SEQ ID NO:22; or D) (a) a VH domain comprising (i) HVR-H1 comprising the amino acid sequence of SEQ ID NO:25, (ii) HVR-H2 comprising the amino acid sequence of SEQ ID NO:26, and (iii) HVR-H3 comprising an amino acid sequence selected from SEQ ID NO:27; and (b) a VL domain comprising (i) HVR-L1 comprising the amino acid sequence of SEQ ID NO:28; (ii) HVR-L2 comprising the amino acid sequence of SEQ ID NO:29 and (iii) HVR-L3 comprising the amino acid sequence of SEQ ID NO:30.

One embodiment of the invention is an isolated antibody that binds to human HLA-G (in one embodiment the antibody binds to HLA-G ß2M MHC I complex comprising SEQ ID NO: 43), wherein the antibody
A)
i) comprises a VH sequence of SEQ ID NO:7 and a VL sequence of SEQ ID NO:8;
ii) or humanized variant of the VH and VL of the antibody under i); or
iii) comprises a VH sequence of SEQ ID NO:33 and a VL sequence of SEQ ID NO:34; or
B)
i) comprises a VH sequence of SEQ ID NO:15 and a VL sequence of SEQ ID NO:16; or
C)
i) comprises a VH sequence of SEQ ID NO:23 and a VL sequence of SEQ ID NO:24; or
D)
i) comprises a VH sequence of SEQ ID NO:31 and a VL sequence of SEQ ID NO:32.

One embodiment of the invention is an (isolated) antibody that binds to human HLA-G (in one embodiment the antibody binds to HLA-G ß2M MHC I complex comprising SEQ ID NO: 43), wherein the antibody comprises
(a) HVR-H1 comprising the amino acid sequence of SEQ ID NO:1; (b) HVR-H2 comprising the amino acid sequence of SEQ ID NO:2; (c) HVR-H3 comprising the amino acid sequence of SEQ ID NO:3; (d) HVR-L1 comprising the amino acid sequence of SEQ ID NO:4; (e) HVR-L2 comprising the amino acid sequence of SEQ ID NO:5; and (f) HVR-L3 comprising the amino acid sequence of SEQ ID NO:6.

One embodiment of the invention is an (isolated) antibody that binds to human HLA-G (in one embodiment the antibody binds to HLA-G ß2M MHC I complex comprising SEQ ID NO: 43), wherein the antibody comprises
(a) HVR-H1 comprising the amino acid sequence of SEQ ID NO:9; (b) HVR-H2 comprising the amino acid sequence of SEQ ID NO:10; (c) HVR-H3 comprising the amino acid sequence of SEQ ID NO:11; (d) HVR-L1 comprising the amino acid sequence of SEQ ID NO:12; (e) HVR-L2 comprising the amino acid sequence of SEQ ID NO:13; and (f) HVR-L3 comprising the amino acid sequence of SEQ ID NO:14.

One embodiment of the invention is an (isolated) antibody that binds to human HLA-G (in one embodiment the antibody binds to HLA-G ß2M MHC I complex comprising SEQ ID NO: 43), wherein the antibody comprises
(a) HVR-H1 comprising the amino acid sequence of SEQ ID NO:17; (b) HVR-H2 comprising the amino acid sequence of SEQ ID NO:18; (c) HVR-H3 comprising the amino acid sequence of SEQ ID NO:19; (d) HVR-L1 comprising the amino acid sequence of SEQ ID NO:20; (e) HVR-L2 comprising the amino acid sequence of SEQ ID NO:21; and (f) HVR-L3 comprising the amino acid sequence of SEQ ID NO:22.

One embodiment of the invention is an (isolated) antibody that binds to human HLA-G (in one embodiment the antibody binds to HLA-G ß2M MHC I complex comprising SEQ ID NO: 43), wherein the antibody comprises
(a) HVR-H1 comprising the amino acid sequence of SEQ ID NO:25; (b) HVR-H2 comprising the amino acid sequence of SEQ ID NO:26; (c) HVR-H3 comprising the amino acid sequence of SEQ ID NO:27; (d) HVR-L1 comprising the amino acid sequence of SEQ ID NO:28; (e) HVR-L2 comprising the amino acid sequence of SEQ ID NO:29; and (f) HVR-L3 comprising the amino acid sequence of SEQ ID NO:30.

One embodiment of the invention is an (isolated) antibody that binds to human HLA-G (in one embodiment the antibody binds to HLA-G ß2M MHC I complex comprising SEQ ID NO: 43), wherein the antibody comprises
i) a VH sequence of SEQ ID NO:7 and a VL sequence of SEQ ID NO:8;
ii) or humanized variant of the VH and VL of the antibody under i).

One embodiment of the invention is an (isolated) antibody that binds to human HLA-G (in one embodiment the antibody binds to HLA-G ß2M MHC I complex comprising SEQ ID NO: 43), wherein the antibody comprises
i) a VH sequence of SEQ ID NO:33 and a VL sequence of SEQ ID NO:34.

One embodiment of the invention is an (isolated) antibody that binds to human HLA-G (in one embodiment the antibody binds to HLA-G ß2M MHC I complex comprising SEQ ID NO: 43), wherein the antibody comprises
a VH sequence of SEQ ID NO:15 and a VL sequence of SEQ ID NO:16.

One embodiment of the invention is an (isolated) antibody that binds to human HLA-G (in one embodiment the antibody binds to HLA-G ß2M MHC I complex comprising SEQ ID NO: 43), wherein the antibody comprises
a VH sequence of SEQ ID NO:23 and a VL sequence of SEQ ID NO:24.

One embodiment of the invention is an (isolated) antibody that binds to human HLA-G (in one embodiment the antibody binds to HLA-G ß2M MHC I complex comprising SEQ ID NO: 43), wherein the antibody comprises
a VH sequence of SEQ ID NO:31 and a VL sequence of SEQ ID NO:32.

One embodiment of the invention is an (isolated) antibody that binds to human HLA-G (in one embodiment the antibody binds to HLA-G ß2M MHC I complex comprising SEQ ID NO: 43), wherein the antibody comprises
A) (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence SEQ ID NO:3; and wherein the VH domain comprises an amino acid sequence of at least 95%, 96%, 97%, 98%, 99% or 100% (in one preferred embodiment 98% or 99% or 100%) sequence identity to the amino acid sequence of SEQ ID NO: 33; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; and wherein the VL domain comprises an amino acid sequence of at least 95%, 96%, 97%, 98%, 99% or 100% (in one preferred embodiment 98% or 99% or 100%) sequence identity to the amino acid sequence of SEQ ID NO: 34; or B) (a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and wherein the VH domain comprises an amino acid sequence of at least 95%, 96%, 97%, 98%, 99% or 100% (in one preferred embodiment 98% or 99% or 100%) sequence identity to the amino acid sequence of SEQ ID NO: 15; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14; and wherein the VL domain comprises an amino acid sequence of at least 95%, 96%, 97%, 98%, 99% or 100% (in one preferred embodiment 98% or 99% or 100%) sequence identity to the amino acid sequence of SEQ ID NO: 16; or C) (a) a VH domain comprising (i) HVR-H1 comprising the amino acid sequence of SEQ ID NO:17, (ii) HVR-H2 comprising the amino acid sequence of SEQ ID NO:18, and (iii) HVR-H3 comprising an amino acid sequence selected from SEQ ID NO:19; and wherein the VH domain comprises an amino acid sequence of at least 95%, 96%, 97%, 98%, 99% or 100% (in one preferred embodiment 98% or 99% or 100%) sequence identity to the amino acid sequence of SEQ ID NO: 23; and (b) a VL domain comprising (i) HVR-L1 comprising the amino acid sequence of SEQ ID NO:20; (ii) HVR-L2 comprising the amino acid sequence of SEQ ID NO:21 and (iii) HVR-L3 comprising the amino acid sequence of SEQ ID NO:22; and wherein the VL domain comprises an amino acid sequence of at least 95%, 96%, 97%, 98%, 99% or 100% (in one preferred embodiment 98% or 99% or 100%) sequence identity to the amino acid sequence of SEQ ID NO: 14; or D) (a) a VH domain comprising (i) HVR-H1 comprising the amino acid sequence of SEQ ID NO:25, (ii) HVR-H2 comprising the amino acid sequence of SEQ ID NO:26, and (iii) HVR-H3 comprising an amino acid sequence selected from SEQ ID NO:27; and wherein the VH domain comprises an amino acid sequence of at least 95%, 96%, 97%, 98%, 99% or 100% (in one preferred embodiment 98% or 99% or 100%) sequence identity to the amino acid sequence of SEQ ID NO: 31; and (b) a VL domain comprising (i) HVR-L1 comprising the amino acid sequence of SEQ ID NO:28; (ii) HVR-L2 comprising the amino acid sequence of SEQ ID NO:29 and (iii) HVR-L3 comprising the amino acid sequence of SEQ ID NO:30; and wherein the VL domain comprises an amino acid sequence of at least 95%, 96%, 97%, 98%, 99% or 100% (in one preferred embodiment 98% or 99% or 100%) sequence identity to the amino acid sequence of SEQ ID NO: 32.

One embodiment of the invention is an (isolated) antibody that binds to human HLA-G (in one embodiment the antibody binds to HLA-G ß2M MHC I complex comprising SEQ ID NO: 43), wherein the antibody comprises
a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; and
wherein the antibody binds to HLA-G ß2M MHC I complex comprising SEQ ID NO: 43 with a binding affinity which is substantially the same as (in one embodiment with a KD value of the binding affinity is reduced at most 10-fold compared to, in one embodiment with a KD value of the binding affinity is reduced at most 5-fold compared to) an antibody comprising a VH sequence of SEQ ID NO:33 and a VL sequence of SEQ ID NO:34 (as determined in surface plasmon resonance assay).

One embodiment of the invention is an (isolated) antibody that binds to human HLA-G (in one embodiment the antibody binds to HLA-G ß2M MHC I complex comprising SEQ ID NO: 43), wherein the antibody comprises
a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence SEQ ID NO:3; and wherein the VH domain comprises an amino acid sequence of at least 95%, 96%, 97%, 98%, 99% or 100% (in one preferred embodiment 98% or 99% or 100%) sequence identity to the amino acid sequence of SEQ ID NO: 33; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; and wherein the VL domain comprises an amino acid sequence of at least 95%, 96%, 97%, 98%, 99% or 100% (in one preferred embodiment 98% or 99% or 100%) sequence identity to the amino acid sequence of SEQ ID NO: 34;
and wherein the antibody binds to HLA-G ß2M MHC I complex comprising SEQ ID NO: 43 with a binding affinity which is substantially the same as (in one embodiment with a KD value of the binding affinity is reduced at most 10-fold compared to, in one embodiment with a KD value of the binding affinity is reduced at most 5-fold compared to) an antibody comprising a VH sequence of SEQ ID NO:33 and a VL sequence of SEQ ID NO:34 (as determined in surface plasmon resonance assay); and or
wherein the antibody is characterized independently by the following properties: the anti-HLA-G antibody
a) does not crossreact with a modified human HLA-G ß2M MHC I complex comprising SEQ ID NO:44; and/or
b) does not crossreact with human HLA-A2 ß2M MHC I complex comprising SEQ ID NO:39 and SEQ ID NO: 37; and/or c) does not crossreact with a mouse H2Kd ß2M MHC I complex comprising SEQ ID NO:45; and/or
d) does not crossreact with rat RT1A ß2M MHC I complex comprising SEQ ID NO:47; and/or
e) inhibits ILT2 binding to monomeric HLA-G ß2M MHC I complex (comprising SEQ ID NO: 43); and/or
f) inhibits ILT2 binding to trimeric HLA-G ß2M MHC I complex (comprising SEQ ID NO: 43), by more than 50% (in one embodiment by more than 60%) (when compared to the binding without antibody) (see Example 4b); and/or
g) inhibits ILT2 binding to monomeric and/or dimeric and/or trimeric HLA-G ß2M MHC I complex (comprising SEQ ID NO: 43), by more than 50% (in on embodiment by more than 80%) (when compared to the binding without antibody) (see Example 4b); and/or
h) inhibits ILT2 binding to (HLA-G on) JEG3 cells (ATCC No. HTB36) (by more than 50% (in one embodiment by more than 80%)) (when compared to the binding without antibody) (see Example 6); and/or
i) binds to (HLA-G on) JEG3 cells (ATCC No. HTB36) (see Example 5), and inhibits ILT2 binding to (HLA-G on) JEG3 cells (ATCC No. HTB36) (by more than 50% (in one embodiment by more than 80%)) (when compared to the binding without antibody) (see Example 6); and/or
j) inhibits CD8a binding to HLAG by more than 80% (when compared to the binding without antibody) (see e.g., Example 4c); and/or
k) restores HLA-G specific suppressed immune response (e.g., suppressed Tumor necrose factor (TNF) alpha release) by monocytes co-cultured with JEG-3 cells (ATCC HTB36).

One embodiment of the invention is an (isolated) antibody that binds to human HLA-G (in one embodiment the antibody binds to HLA-G ß2M MHC I complex comprising SEQ ID NO: 43), wherein the antibody binds to the same epitope as an antibody comprising a VH sequence of SEQ ID NO:33 and a VL sequence of SEQ ID NO:34.

One embodiment of the invention is an (isolated) antibody that binds to human HLA-G (in one embodiment the antibody binds to HLA-G ß2M MHC I complex comprising SEQ ID NO: 43), wherein the antibody comprises
a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence SEQ ID NO:11; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14; and
wherein the antibody binds to HLA-G ß2M MHC I complex comprising SEQ ID NO: 43 with a binding affinity which is substantially the same as (in one embodiment with a KD value of the binding affinity is reduced at most 10-fold compared to, in one embodiment with a KD value of the binding affinity is reduced at most 5-fold compared to) an antibody comprising a VH sequence of SEQ ID NO:15 and a VL sequence of SEQ ID NO:16 (as determined in surface plasmon resonance assay).

One embodiment of the invention is an (isolated) antibody that binds to human HLA-G (in one embodiment the antibody binds to HLA-G ß2M MHC I complex comprising SEQ ID NO: 43), wherein the antibody comprises
a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence SEQ ID NO:11; and wherein the VH domain comprises an amino acid sequence of at least 95%, 96%, 97%, 98%, 99% or 100% (in one preferred embodiment 98% or 99% or 100%) sequence identity to the amino acid sequence of SEQ ID NO: 15; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14; and wherein the VL domain comprises an amino acid sequence of at least 95%, 96%, 97%, 98%, 99% or 100% (in one preferred embodiment 98% or 99% or 100%) sequence identity to the amino acid sequence of SEQ ID NO: 16;
and wherein the antibody binds to HLA-G ß2M MHC I complex comprising SEQ ID NO: 43 with a binding affinity which is substantially the same as (in one embodiment with a KD value of the binding affinity is reduced at most 10-fold compared to, in one embodiment with a KD value of the binding affinity is reduced at most 5-fold compared to) an antibody comprising a VH sequence of SEQ ID NO:15 and a VL sequence of SEQ ID NO:16 (as determined in surface plasmon resonance assay); and/or
wherein the antibody is characterized independently by the following properties: the anti-HLA-G antibody
a) does not crossreact with a modified human HLA-G ß2M MHC I complex comprising SEQ ID NO:44; and/or
b) does not crossreact with human HLA-A2 ß2M MHC I complex comprising SEQ ID NO:39 and SEQ ID NO: 37; and/or
c) does not crossreact with a mouse H2Kd ß2M MHC I complex comprising SEQ ID NO:45; and/or
d) does not crossreact with rat RT1A ß2M MHC I complex comprising SEQ ID NO:47; and/or
e) inhibits ILT2 binding to monomeric HLA-G ß2M MHC I complex (comprising SEQ ID NO: 43); and/or
f) inhibits ILT2 binding to trimeric HLA-G ß2M MHC I complex (comprising SEQ ID NO: 43), by more than 50% (in one embodiment by more than 60%) (when compared to the binding without antibody) (see Example 4b); and/or
g) inhibits ILT2 binding to monomeric and/or dimeric and/or trimeric HLA-G ß2M MHC I complex (comprising SEQ ID NO: 43), by more than 50% (in on embodiment by more than 80%) (when compared to the binding without antibody) (see Example 4b); and/or
h) inhibits ILT2 binding to (HLA-G on) JEG3 cells (ATCC No. HTB36) (by more than 50% (in one embodiment by more than 80%)) (when compared to the binding without antibody) (see Example 6); and/or
i) binds to (HLA-G on) JEG3 cells (ATCC No. HTB36) (see Example 5), and inhibits ILT2 binding to (HLA-G on) JEG3 cells (ATCC No. HTB36) (by more than 50% (in one embodiment by more than 80%)) (when compared to the binding without antibody) (see Example 6); and/or j) inhibits CD8a binding to HLAG by more than 80% (when compared to the binding without antibody) (see e.g., Example 4c); and/or k) restores HLA-G specific suppressed immune response (e.g., suppressed Tumor necrose factor (TNF) alpha release) by monocytes co-cultured with JEG-3 cells (ATCC HTB36).

One embodiment of the invention is an (isolated) antibody that binds to human HLA-G (in one embodiment the antibody binds to HLA-G ß2M MHC I complex comprising SEQ ID NO: 43), wherein the antibody binds to the same epitope as an antibody comprising a VH sequence of SEQ ID NO:15 and a VL sequence of SEQ ID NO:16.

One embodiment of the invention is an (isolated) antibody that binds to human HLA-G (in one embodiment the antibody binds to HLA-G ß2M MHC I complex comprising SEQ ID NO: 43), wherein the antibody comprises
a) a VH domain comprising (i) HVR-H1 comprising the amino acid sequence of SEQ ID NO:17, (ii) HVR-H2 comprising the amino acid sequence of SEQ ID NO:18, and (iii) HVR-H3 comprising an amino acid sequence SEQ ID NO:19; and (b) a VL domain comprising (i) HVR-L1 comprising the amino acid sequence of SEQ ID NO:20; (ii) HVR-L2 comprising the amino acid sequence of SEQ ID NO:21 and (iii) HVR-L3 comprising the amino acid sequence of SEQ ID NO:22; and
wherein the antibody binds to HLA-G ß2M MHC I complex comprising SEQ ID NO: 43 with a binding affinity which is substantially the same as (in one embodiment with a KD value of the binding affinity is reduced at most 10-fold compared to, in one embodiment with a KD value of the binding affinity is reduced at most 5-fold compared to) an antibody comprising a VH sequence of SEQ ID NO:23 and a VL sequence of SEQ ID NO:24 (as determined in surface plasmon resonance assay).

One embodiment of the invention is an (isolated) antibody that binds to human HLA-G (in one embodiment the antibody binds to HLA-G ß2M MHC I complex comprising SEQ ID NO: 43), wherein the antibody comprises
a) a VH domain comprising (i) HVR-H1 comprising the amino acid sequence of SEQ ID NO:17, (ii) HVR-H2 comprising the amino acid sequence of SEQ ID NO:18, and (iii) HVR-H3 comprising an amino acid sequence SEQ ID NO:19; and wherein the VH domain comprises an amino acid sequence of at least 95%, 96%, 97%, 98%, 99% or 100% (in one preferred embodiment 98% or 99% or 100%) sequence identity to the amino acid sequence of SEQ ID NO: 23; and (b) a VL domain comprising (i) HVR-L1 comprising the amino acid sequence of SEQ ID NO:20; (ii) HVR-L2 comprising the amino acid sequence of SEQ ID NO:21 and (iii) HVR-L3 comprising the amino acid sequence of SEQ ID NO:22; and wherein the VL domain comprises an amino acid sequence of at least 95%, 96%, 97%, 98%, 99% or 100% (in one preferred embodiment 98% or 99% or 100%) sequence identity to the amino acid sequence of SEQ ID NO: 24;
and wherein the antibody binds to HLA-G ß2M MHC I complex comprising SEQ ID NO: 43 with a binding affinity which is substantially the same as (in one embodiment with a KD value of the binding affinity is reduced at most 10-fold compared to, in one embodiment with a KD value of the binding affinity is reduced at most 5-fold compared to) an antibody comprising a VH sequence of SEQ ID NO:23 and a VL sequence of SEQ ID NO:24 (as determined in surface plasmon resonance assay); and/or
wherein the antibody is characterized independently by the following properties: the anti-HLA-G antibody
a) does not crossreact with a modified human HLA-G ß2M MHC I complex comprising SEQ ID NO:44; and/or
b) does not crossreact with human HLA-A2 ß2M MHC I complex comprising SEQ ID NO:39 and SEQ ID NO: 37; and/or
c) does not crossreact with a mouse H2Kd ß2M MHC I complex comprising SEQ ID NO:45; and/or
e) does not crossreact with rat RT1A ß2M MHC I complex comprising SEQ ID NO:47; and/or
f) inhibits ILT2 binding to monomeric HLA-G ß2M MHC I complex (comprising SEQ ID NO: 43); and/or
g) inhibits ILT2 binding to trimeric HLA-G ß2M MHC I complex (comprising SEQ ID NO: 43), by more than 50% (in one embodiment by more than 60%) (when compared to the binding without antibody) (see Example 4b); and/or
h) inhibits ILT2 binding to monomeric and/or dimeric and/or trimeric HLA-G ß2M MHC I complex (comprising SEQ ID NO: 43), by more than 50% (in on embodiment by more than 80%) (when compared to the binding without antibody) (see Example 4b); and/or
i) inhibits ILT2 binding to (HLA-G on) JEG3 cells (ATCC No. HTB36) (by more than 50% (in one embodiment by more than 80%)) (when compared to the binding without antibody) (see Example 6); and/or
j) binds to (HLA-G on) JEG3 cells (ATCC No. HTB36) (see Example 5), and inhibits ILT2 binding to (HLA-G on) JEG3 cells (ATCC No. HTB36) (by more than 50% (in one embodiment by more than 80%)) (when compared to the binding without antibody) (see Example 6); and/or
k) inhibits CD8a binding to HLAG by more than 80% (when compared to the binding without antibody) (see e.g., Example 4c); and/or
l) restores HLA-G specific suppressed immune response (e.g., suppressed Tumor necrose factor (TNF) alpha release) by monocytes co-cultured with JEG-3 cells (ATCC HTB36).

One embodiment of the invention is an (isolated) antibody that binds to human HLA-G (in one embodiment the antibody binds to HLA-G ß2M MHC I complex comprising SEQ ID NO: 43), wherein the antibody binds to the same epitope as an antibody comprising a VH sequence of SEQ ID NO:23 and a VL sequence of SEQ ID NO:24.

One embodiment of the invention is an (isolated) antibody that binds to human HLA-G (in one embodiment the antibody binds to HLA-G ß2M MHC I complex comprising SEQ ID NO: 43), wherein the antibody comprises
a) a VH domain comprising (i) HVR-H1 comprising the amino acid sequence of SEQ ID NO:25, (ii) HVR-H2 comprising the amino acid sequence of SEQ ID NO:26, and (iii) HVR-H3 comprising an amino acid sequence SEQ ID NO:27; and (b) a VL domain comprising (i) HVR-L1 comprising the amino acid sequence of SEQ ID NO:28; (ii) HVR-L2 comprising the amino acid sequence of SEQ ID NO:29 and (iii) HVR-L3 comprising the amino acid sequence of SEQ ID NO:30; and wherein the antibody binds to HLA-G β2M MHC I complex comprising SEQ ID NO: 43 with a binding affinity which is substantially the same as (in one embodiment with a KD value of the binding affinity is reduced at most 10-fold compared to, in one embodiment with a KD value of the binding affinity is reduced at most 5-fold compared to) an antibody comprising a VH sequence of SEQ ID NO:31 and a VL sequence of SEQ ID NO:32 (as determined in surface plasmon resonance assay).

One embodiment of the invention is an (isolated) antibody that binds to human HLA-G (in one embodiment the antibody binds to HLA-G β2M MHC I complex comprising SEQ ID NO: 43), wherein the antibody comprises
 a) a VH domain comprising (i) HVR-H1 comprising the amino acid sequence of SEQ ID NO:25, (ii) HVR-H2 comprising the amino acid sequence of SEQ ID NO:26, and (iii) HVR-H3 comprising an amino acid sequence SEQ ID NO:27; and wherein the VH domain comprises an amino acid sequence of at least 95%, 96%, 97%, 98%, 99% or 100% (in one preferred embodiment 98% or 99% or 100%) sequence identity to the amino acid sequence of SEQ ID NO: 31; and (b) a VL domain comprising (i) HVR-L1 comprising the amino acid sequence of SEQ ID NO:28; (ii) HVR-L2 comprising the amino acid sequence of SEQ ID NO:29 and (iii) HVR-L3 comprising the amino acid sequence of SEQ ID NO:30; and wherein the VL domain comprises an amino acid sequence of at least 95%, 96%, 97%, 98%, 99% or 100% (in one preferred embodiment 98% or 99% or 100%) sequence identity to the amino acid sequence of SEQ ID NO: 32;

and wherein the antibody binds to HLA-G β2M MHC I complex comprising SEQ ID NO: 43 with a binding affinity which is substantially the same as (in one embodiment with a KD value of the binding affinity is reduced at most 10-fold compared to, in one embodiment with a KD value of the binding affinity is reduced at most 5-fold compared to) an antibody comprising a VH sequence of SEQ ID NO:31 and a VL sequence of SEQ ID NO:32 (as determined in surface plasmon resonance assay); and or wherein the antibody is characterized independently by the following properties: the anti-HLA-G antibody
 a) does not crossreact with a modified human HLA-G β2M MHC I complex comprising SEQ ID NO:44; and/or
 b) does not crossreact with human HLA-A2 β2M MHC I complex comprising SEQ ID NO:39 and SEQ ID NO: 37; and/or
 c) does not crossreact with a mouse H2Kd β2M MHC I complex comprising SEQ ID NO:45; and/or
 d) does not crossreact with rat RT1A β2M MHC I complex comprising SEQ ID NO:47; and/or
 e) inhibits ILT2 binding to monomeric HLA-G β2M MHC I complex (comprising SEQ ID NO: 43); and/or
 f) inhibits ILT2 binding to trimeric HLA-G β2M MHC I complex (comprising SEQ ID NO: 43), by more than 50% (in one embodiment by more than 60%) (when compared to the binding without antibody) (see Example 4b); and/or
 g) inhibits ILT2 binding to monomeric and/or dimeric and/or trimeric HLA-G β2M MHC I complex (comprising SEQ ID NO: 43), by more than 50% (in on embodiment by more than 80%) (when compared to the binding without antibody) (see Example 4b); and/or
 h) inhibits ILT2 binding to (HLA-G on) JEG3 cells (ATCC No. HTB36) (by more than 50% (in one embodiment by more than 80%)) (when compared to the binding without antibody) (see Example 6); and/or
 i) binds to (HLA-G on) JEG3 cells (ATCC No. HTB36) (see Example 5), and inhibits ILT2 binding to (HLA-G on) JEG3 cells (ATCC No. HTB36) (by more than 50% (in one embodiment by more than 80%)) (when compared to the binding without antibody) (see Example 6); and/or
 j) inhibits CD8a binding to HLAG by more than 80% (when compared to the binding without antibody) (see e.g., Example 4c); and/or
 k) restores HLA-G specific suppressed immune response (e.g., suppressed Tumor necrose factor (TNF) alpha release) by monocytes co-cultured with JEG-3 cells (ATCC HTB36).

One embodiment of the invention is an (isolated) antibody that binds to human HLA-G (in one embodiment the antibody binds to HLA-G β2M MHC I complex comprising SEQ ID NO: 43), wherein the antibody binds to the same epitope as an antibody comprising a VH sequence of SEQ ID NO:31 and a VL sequence of SEQ ID NO:32.

In one embodiment of the invention the antibody is of IgG1 isotype. In one embodiment of the invention the antibody is of IgG1 isotype with mutations L234A, L235A and P329G (numbering according to the EU index of Kabat)

In a further aspect, an anti-HLA-G antibody according to any of the above embodiments may incorporate any of the features, singly or in combination, as described in Sections 1-7 below:

1. Antibody Affinity

In certain embodiments, an antibody provided herein has a dissociation constant KD of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one preferred embodiment, KD is measured using surface plasmon resonance assays using a BIACORE®) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$ or ka) and dissociation rates ($k_{off}$ or kd) are calculated using a simple one-to-one Langmuir binding model (BIACORE® Evaluation Software version 3.2) by simultaneously fitting the association and dissociation sensorgrams. The equilibrium dissociation constant KD is calculated as the ratio kd/ka ($k_{off}/k_{on}$.) See, e.g., Chen, Y. et al., J. Mol. Biol. 293 (1999) 865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing SDR (a-CDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R. et al., Monoclonal Antibody Production Techniques and Applications, Marcel Dekker, Inc., New York (1987), pp. 51-63; and Boerner, P. et al., J. Immunol. 147 (1991) 86-95) Human antibodies generated via human B-cell hybridoma technology are also described in Li, J. et al., Proc. Natl. Acad. Sci.

USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R. et al., Methods in Molecular Biology 178 (2001) 1-37 and further described, e.g., in the McCafferty, J. et al., Nature 348 (1990) 552-554; Clackson, T. et al., Nature 352 (1991) 624-628; Marks, J. D. et al., J. Mol. Biol. 222 (1992) 581-597; Marks, J. D. and Bradbury, A., Methods in Molecular Biology 248 (2003) 161-175; Sidhu, S. S. et al., J. Mol. Biol. 338 (2004) 299-310; Lee, C. V. et al., J. Mol. Biol. 340 (2004) 1073-1093; Fellouse, F. A., Proc. Natl. Acad. Sci. USA 101 (2004) 12467-12472; and Lee, C. V. et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G. et al., Ann. Rev. Immunol. 12 (1994) 433-455. Phage typically displays antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths, A. D. et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for HLA-G and the other is for any other antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g., Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g., US 2006/0025576).

The antibody or fragment herein also includes a "Dual Acting Fab" or "DAF" comprising an antigen binding site that binds to HLA-G as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793, WO2011/117330, WO2012/025525, WO2012/025530, WO2013/026835, WO2013/026831, WO2013/164325, or WO 2013/174873.

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Exemplary changes are provided in Table 1 under the heading of "exemplary substitutions", and as further described below in reference to amino acid side chain classes. Conservative substitutions are shown in Table 1 under the heading of "preferred substitutions". Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604).

In one embodiment of the invention such antibody is an IgG1 with mutations L234A and L235A or with mutations L234A, L235A and P329G. In another embodiment or IgG4 with mutations S228P and L235E or S228P, L235E or and P329G (numbering according to EU index of Kabat et al, Kabat et al., Sequences of Proteins of Immunological Interest, 5th Ed. Public Health Service, National Institutes of Health, Bethesda, Md., 1991).

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc region variants.

c) Cysteine Engineered Antibody Variants

In certain embodiments, it may be desirable to create cysteine engineered antibodies, e.g., "THIOMAB™" antibodies, in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

d) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-HLA-G antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell, a HEK293 cell or lymphoid cell (e.g., Y0, NS0, Sp20 cell). In one embodiment, a method of making an anti-HLA-G antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HLA-G antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-HLA-G antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with HLA-G-0031 (comprising a VH sequence of SEQ ID NO:7 and a VL sequence of SEQ ID NO:8) for binding to HLA-G. One embodiment of the invention is an antibody which competes for binding to human HLA-G with an anti-HLA-G antibody comprising all 3 HVRs of VH sequence of SEQ ID NO:7 and all 3 HVRs of VL sequence of SEQ ID NO:8. In certain embodiments, such a competing antibody binds to the same epitope (e.g., a linear or a conformational epitope) that is bound by anti-HLA-G antibody HLA-G-0031. In one embodiment an anti-HLA-G antibody is provided which binds to the same epitope on HLA-G as an antibody comprising a VH sequence of SEQ ID NO:7 and a VL sequence of SEQ ID NO:8. In another aspect, competition assays may be used to identify an antibody that competes with HLA-G-0090 (comprising a VH sequence of SEQ ID NO:31 and a VL sequence of SEQ ID NO:32) for binding to HLA-G. One embodiment of the invention is an antibody which competes for binding to human HLA-G with an anti-HLA-G antibody comprising all 3 HVRs of VH sequence of SEQ ID NO:31 and all 3 HVRs of VL sequence of SEQ ID NO:32. In certain embodiments, such a competing antibody binds to the same epitope (e.g., a linear or a conformational epitope) that is bound by anti-HLA-G antibody HLA-G-0090. In one embodiment an anti-HLA-G antibody is provided which binds to the same epitope on HLA-G as an antibody comprising a VH sequence of SEQ ID NO:31 and a VL sequence of SEQ ID NO:32. Detailed exemplary methods for mapping an epitope to which an antibody binds are provided in Morris, G. E. (ed.), Epitope Mapping Protocols, In: Methods in Molecular Biology, Vol. 66, Humana Press, Totowa, N.J. (1996).

In an exemplary competition assay, immobilized HLA-G is incubated in a solution comprising a first labeled antibody that binds to HLA-G (e.g., anti-HLA-G antibody HLA-G-0031 or HLA-G-0090) and a second unlabeled antibody that is being tested for its ability to compete with the first antibody for binding to HLA-G. The second antibody may be present in a hybridoma supernatant. As a control, immobilized HLA-G is incubated in a solution comprising the first labeled antibody but not the second unlabeled antibody. After incubation under conditions permissive for binding of the first antibody to HLA-G, excess unbound antibody is removed, and the amount of label associated with immobilized HLA-G is measured. If the amount of label associated with immobilized HLA-G is substantially reduced in the test sample relative to the control sample, then that indicates that the second antibody is competing with the first antibody for binding to HLA-G. See Harlow, E. and Lane, D., Antibodies: A Laboratory Manual, Chapter 14, Cold Spring Harbor Laboratory, Cold Spring Harbor, N.Y. (1988). For another exemplary competition assay see Example 2 (Epitope mapping ELISA/Binding competition assay).

2. Activity Assays

In one aspect, assays are provided for identifying anti-HLA-G antibodies thereof having biological activity. Biological activity may include, e.g., the ability to enhance the activation and/or proliferation of different immune cells including T-cells. E.g., they enhance release of immunomodulating cytokines (e.g., interferon-gamma (IFN-gamma) and/or tumor necrosis factor alpha (TNF alpha)). Other immunomodulating cytokines which are or can be enhanced are e.g., IL1ß, IL6, IL12, Granzyme B etc. binding to different cell types. Antibodies having such biological activity in vivo and/or in vitro are also provided.

In certain embodiments, an antibody of the invention is tested for such biological activity as described e.g., in Examples below.

D. Immunoconjugates (Cancer Only or Modify for Target)

The invention also provides immunoconjugates comprising an anti-HLA-G antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman, L. M. et al., Cancer Res. 53 (1993) 3336-3342; and Lode, H. N. et al., Cancer Res. 58 (1998) 2925-2928); an anthracycline such as daunomycin or doxorubicin (see Kratz, F. et al., Curr. Med. Chem. 13 (2006) 477-523; Jeffrey, S. C. et al., Bioorg. Med. Chem. Lett. 16 (2006) 358-362; Torgov, M. Y. et al., Bioconjug. Chem. 16 (2005) 717-721; Nagy, A. et al., Proc. Natl. Acad. Sci. USA 97 (2000) 829-834; Dubowchik, G. M.

et al., Bioorg. & Med. Chem. Letters 12 (2002) 1529-1532; King, H. D. et al., J. Med. Chem. 45 (20029 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S. et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V. et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

E. Methods and Compositions for Diagnostics and Detection

In certain embodiments, any of the anti-HLA-G antibodies provided herein are useful for detecting the presence of HLA-G in a biological sample. The term "detecting" as used herein encompasses quantitative or qualitative detection. In certain embodiments, a biological sample comprises a cell or tissue, such as immune cell or T cell infiltrates and or tumor cells.

In one embodiment, an anti-HLA-G antibody for use in a method of diagnosis or detection is provided. In a further aspect, a method of detecting the presence of HLA-G in a biological sample is provided. In certain embodiments, the method comprises contacting the biological sample with an anti-HLA-G antibody as described herein under conditions permissive for binding of the anti-HLA-G antibody to HLA-G, and detecting whether a complex is formed between the anti-HLA-G antibody and HLA-G. Such method may be an in vitro or in vivo method. In one embodiment, an anti-HLA-G antibody is used to select subjects eligible for therapy with an anti-HLA-G antibody, e.g., where HLA-G is a biomarker for selection of patients.

In certain embodiments, labeled anti-HLA-G antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, 0-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-HLA-G antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules.

The formulations to be used for in vivo administration are generally sterile. Sterility may be readily accomplished, e.g., by filtration through sterile filtration membranes.

G. Therapeutic Methods and Compositions

Any of the anti-HLA-G antibodies (or antigen binding proteins) provided herein may be used in therapeutic methods.

In one aspect, an anti-HLA-G antibody for use as a medicament is provided. In further aspects, an anti-HLA-G antibody or use in treating cancer is provided. In certain embodiments, an anti-HLA-G antibody for use in a method of treatment is provided. In certain embodiments, the invention provides an anti-HLA-G antibody for use in a method of treating an individual having cancer comprising administering to the individual an effective amount of the anti-HLA-G antibody.

In further embodiments, the invention provides an anti-HLA-G antibody for use as immunomodulatory agent/to directly or indirectly induce proliferation, activation of immune cells (e.g., by release of immunostimulatory cytokines like TNFalpha (TNFa) and IFNgamma (IFNg) or further recruitment of immune cells. In certain embodiments, the invention provides an anti-HLA-G antibody for use in a method of immunomodulatory agent/to directly or indirectly induce proliferation, activation of immune cells e.g. by release of immunostimulatory cytokines like TNFa and IFNgamma or further recruitment of immune cells in an individual comprising administering to the individual an effective of the anti-HLA-G antibody for immunomodulation/or directly or indirectly induce proliferation, activation of immune cells e.g. by release of immunostimulatory cytokines like TNFa and IFNgamma or further recruitment of immune cells.

In further embodiments, the invention provides an anti-HLA-G antibody for use as immunostimulatory agent/or stimulating tumor necrosis factor alpha (TNF alpha) release. In certain embodiments, the invention provides an anti-HLA-G antibody for use in a method of immunomodulation to directly or indirectly induce proliferation, activation e.g. by release of immunostimulatory cytokines like TNFa and IFNg or further recruitment of immune cells in an individual comprising administering to the individual an effective of the anti-HLA-G antibody immunomodulation to directly or indirectly induce proliferation, activation e.g. by release of immunostimulatory cytokines like TNFa and IFNg or further recruitment of immune cells.

In further embodiments, the invention provides an anti-HLA-G antibody for use in the inhibition of immunosuppression in tumors (tumor cells). In further embodiments, the invention provides an anti-HLA-G antibody for use in restoration of HLA-G specific suppressed immune response (e.g., cytokine release by immune cells (e.g., TNF alpha release by monocytes).

An "individual" according to any of the above embodiments is preferably a human. In a further aspect, the invention provides for the use of an anti-HLA-G antibody in the manufacture or preparation of a medicament. In one embodiment, the medicament is for treatment of cancer. In a further embodiment, the medicament is for use in a method of treating cancer comprising administering to an individual having cancer an effective amount of the medicament. In a further embodiment, the medicament is for inducing cell mediated lysis of cancer cells. In a further embodiment, the medicament is for use in a method of inducing cell mediated lysis of cancer cells in an individual suffering from cancer comprising administering to the individual an amount effective of the medicament to induce apoptosis in a cancer cell/or to inhibit cancer cell proliferation. An "individual" according to any of the above embodiments may be a human.

In a further aspect, the invention provides a method for treating cancer. In one embodiment, the method comprises administering to an individual having cancer an effective amount of an anti-HLA-G. An "individual" according to any of the above embodiments may be a human.

In a further aspect, the invention provides a method for inducing cell mediated lysis of cancer cells in an individual suffering from cancer. In one embodiment, the method comprises administering to the individual an effective amount of an anti-HLA-G to induce cell mediated lysis of cancer cells in the individual suffering from cancer. In one embodiment, an "individual" is a human.

In a further aspect, the invention provides pharmaceutical formulations comprising any of the anti-HLA-G antibodies provided herein, e.g., for use in any of the above therapeutic methods. In one embodiment, a pharmaceutical formulation comprises any of the anti-HLA-G antibodies provided herein and a pharmaceutically acceptable carrier.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intra-arterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-HLA-G antibody.

It is understood that any of the above formulations or therapeutic methods may be carried out using an immunoconjugate of the invention in place of or in addition to an anti-HLA-G antibody.

II. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples and figures are provided to aid the understanding of the present invention, the true scope of which is set forth in the appended claims. It is understood that modifications can be made in the procedures set forth without departing from the spirit of the invention.

Description of the Amino Acid Sequences

Anti-HLAG antibodies (variable regions and hypervariable regions (HVRs)):

SEQ ID NO: 1 heavy chain HVR-H1, HLA-G-0031
SEQ ID NO: 2 heavy chain HVR-H2, HLA-G-0031
SEQ ID NO: 3 heavy chain HVR-H3, HLA-G-0031
SEQ ID NO: 4 light chain HVR-L1, HLA-G-0031
SEQ ID NO: 5 light chain HVR-L2, HLA-G-0031
SEQ ID NO: 6 light chain HVR-L3, HLA-G-0031
SEQ ID NO: 7 heavy chain variable domain VH, HLA-G-0031
SEQ ID NO: 8 light chain variable domain VL, HLA-G-0031
SEQ ID NO: 9 heavy chain HVR-H1, HLA-G-0039
SEQ ID NO: 10 heavy chain HVR-H2, HLA-G-0039
SEQ ID NO: 11 heavy chain HVR-H3, HLA-G-0039
SEQ ID NO: 12 light chain HVR-L1, HLA-G-0039
SEQ ID NO: 13 light chain HVR-L2, HLA-G-0039
SEQ ID NO: 14 light chain HVR-L3, HLA-G-0039
SEQ ID NO: 15 heavy chain variable domain VH, HLA-G-0039
SEQ ID NO: 16 light chain variable domain VL, HLA-G-0039
SEQ ID NO: 17 heavy chain HVR-H1, HLA-G-0041
SEQ ID NO: 18 heavy chain HVR-H2, HLA-G-0041
SEQ ID NO: 19 heavy chain HVR-H3, HLA-G-0041
SEQ ID NO: 20 light chain HVR-L1, HLA-G-0041
SEQ ID NO: 21 light chain HVR-L2, HLA-G-0041
SEQ ID NO: 22 light chain HVR-L3, HLA-G-0041
SEQ ID NO: 23 heavy chain variable domain VH, HLA-G-0041

SEQ ID NO: 24 light chain variable domain VL, HLA-G-0041
SEQ ID NO: 25 heavy chain HVR-H1, HLA-G-0090
SEQ ID NO: 26 heavy chain HVR-H2, HLA-G-0090
SEQ ID NO: 27 heavy chain HVR-H3, HLA-G-0090
SEQ ID NO: 28 light chain HVR-L1, HLA-G-0090
SEQ ID NO: 29 light chain HVR-L2, HLA-G-0090
SEQ ID NO: 30 light chain HVR-L3, HLA-G-0090
SEQ ID NO: 31 heavy chain variable domain VH, HLA-G-0090
SEQ ID NO: 32 light chain variable domain VL, HLA-G-0090
SEQ ID NO: 33 humanized variant heavy chain variable domain VH, HLA-G-0031-0104 (HLA-G-0104)
SEQ ID NO: 34 humanized variant light chain variable domain VL, HLA-G-0031-0104 (HLA-G-0104)
Further Sequences
SEQ ID NO: 35: exemplary human HLA-G
SEQ ID NO: 36: exemplary human HLA-G extracellular domain (ECD)
SEQ ID NO: 37: exemplary human ß2M
SEQ ID NO: 38: modified human HLA-G (wherein the HLA-G specific amino acids have been replaced by HLA-A consensus amino acids (=degrafted HLA-G see also FIG. 1) ECD)
SEQ ID NO: 39: exemplary human HLA-A2
SEQ ID NO: 40: exemplary human HLA-A2 ECD
SEQ ID NO: 41: exemplary mouse H2Kd ECD
SEQ ID NO: 42: exemplary rat RT1A ECD
SEQ ID NO: 43: exemplary human HLA-G ß2M MHC class I complex
SEQ ID NO: 44: exemplary modified human HLA-G ß2M MHC class I complex (wherein the HLA-G specific amino acids have been replaced by HLA-A consensus amino acids (=degrafted HLA-G) see also FIG. 1)
SEQ ID NO: 45: exemplary mouse H2Kd ß2M MHC class I complex
SEQ ID NO: 46: exemplary human HLA-G/mouse H2Kd ß2M MHC class I complex wherein the positions specific for human HLA-G are grafted onto the mouse H2Kd framework
SEQ ID NO: 47: exemplary rat RT1A ß2M MHC class I complex
SEQ ID NO: 48: exemplary human HLA-G/rat RT1A ß2M MHC class I complex wherein the positions specific for human HLA-G are grafted onto the rat RT1A framework
SEQ ID NO: 49 linker and his-Tag
SEQ ID NO: 50 peptide
SEQ ID NO: 51 human kappa light chain constant region
SEQ ID NO: 52 human lambda light chain constant region
SEQ ID NO: 53 human heavy chain constant region derived from IgG1
SEQ ID NO: 54 human heavy chain constant region derived from IgG1 with mutations L234A, L235A and P329G
SEQ ID NO: 55 human heavy chain constant region derived from IgG4

The Amino Acid Sequences of the Anti-HLAG Antibodies (Variable Regions with Underlined and Bold Hypervariable Regions (HVRs)):

SEQ ID NO: 7: heavy chain variable domain VH, HLA-G-0031:
QVKLMQSGAALVKPGTSVKMSCNASGYTFTDYWVSWVKQSHGKRLEWV

GEISPNSGASNFDENFKDKATLTVDKSTSTAYMELSRLTSEDSAIYYCTR

SSHGSFRWFAYWGQGTLVTVSS

SEQ ID NO: 8: light chain variable domain VL, HLA-G-0031:
AIVLNQSPSSIVASQGEKVTITCRASSSVSSNHLHWYQQKPGAFPKFVIY

STSQRASGIPSRFSGSGSGTSYSFTISRVEAEDVATYYCQQGSSNPYTFG

AGTKLELK

SEQ ID NO: 33: humanized variant heavy chain variable domain VH, HLA-G-0031-0104 (HLA-G-0104):
QVQLVQSGAEVKKPGASVKVSCKASGYTFTDYWVSWVRQAPGQRLEWM

GEISPNSGASNFDENFQGRVTITRDTSASTAYMELSSLRSEDTAVYYCTR

SSHGSFRWFAYWGQGTLVTVSS

SEQ ID NO: 34: humanized variant light chain variable domain VL, HLA-G-0031-0104 (HLA-G-0104):
DIQMTQSPSSLSASVGDRVTITCRASSSVSSNHLHWYQQKPGKAPKFLIY

STSQRASGVPSRFSGSGSGTEFTLTISSLQPEDFATYYCQQGSSNPYTFG

QGTKLEIK

SEQ ID NO: 15: heavy chain variable domain VH, HLA-G-0039:
EVQLLESGGGLVQPGGSLRLSCAASGFTFSSYAMNWVRQAPGKGLEWVS

VISGSGVSTYYADSVKGRFTISRDNSRNTLSLQMNSLRAEDTAVYYCAKD

GSYNYGYGDYFDYWGQGTLVTVSS

SEQ ID NO: 16: light chain variable domain VL, HLA-G-0039
DIVMTQSPDSLAVSLGERATINCKSSQSVLYSSKNKNYLAWYQQKPGQPP

KLFIYWASTRESGVPDRFSGSGSGTDFTLTISSLQAEDVAVYYCQQYYNT

PRTFGQGTKVEIK

SEQ ID NO: 23: heavy chain variable domain VH, HLA-G-0041:
EVQLLESGGGLVQPGGSLRLSCAASGFTFSTYGMSWVRQAPGKGLEWVS

VISGGGYSTYYADSVKGRFTISRDNSKNTLYLQMNRLAEDTAVYYCAK

DGSYNYGYGDYFDYVVGQGTLVTVSS

SEQ ID NO: 24: light chain variable domain VL, HLA-G-0041
DIVMTQSPDSLAVSLGERATINCKSSQNVLYSSNNKNYLAWYQQKPGQPP

KLLIYWASTRESGVPDRFSGSGSGTDFTLTISSLQAEDVAVYYCQQYNT

PRTFGQGTKVEIK

SEQ ID NO: 31: heavy chain variable domain VH, HLA-G-0090:
QVQLQQSGPGLLKPSQTLSLTCAISGDSVSSNRAAWNWIRQSPSRGLEWL

GRTYYRSKWYNDYAVSVQGRITLIPDTSKNQFSLRLNSVTPEDTAVYYCA

SVRAVAPFDYWGQGVLVTVSS

SEQ ID NO: 32: light chain variable domain VL, HLA-G-0090
DIVMTQSPDSLAVSLGERATINCKSSQSVLNSSNNKNNLAWYQQPGQPP

KLLIYWASTRESGVPDRFSGSGSGTDFTLTISSLQAEDVAVYFCQQYYRT

PWTFGQGTKVEIK

In the following specific embodiments of the invention are listed:

1. An isolated antibody that specifically binds to human HLA—wherein the antibody comprises
   A) (a) a VH domain comprising (i) HVR-H1 comprising the amino acid sequence of SEQ ID NO:1, (ii) HVR-H2 comprising the amino acid sequence of SEQ ID NO:2, and (iii) HVR-H3 comprising an amino acid sequence selected from SEQ ID NO:3; and (b) a VL domain comprising (i) HVR-L1 comprising the amino acid sequence of SEQ ID NO:4; (ii) HVR-L2 comprising the amino acid sequence of SEQ ID NO:5 and (iii) HVR-L3 comprising the amino acid sequence of SEQ ID NO:6; or
   B) (a) a VH domain comprising (i) HVR-H1 comprising the amino acid sequence of SEQ ID NO:9, (ii) HVR-H2 comprising the amino acid sequence of SEQ ID NO:10, and (iii) HVR-H3 comprising an amino acid sequence selected from SEQ ID NO:11; and (b) a VL domain comprising (i) HVR-L1 comprising the amino acid sequence of SEQ ID NO:12; (ii) HVR-L2 comprising the amino acid sequence of SEQ ID NO:13 and (iii) HVR-L3 comprising the amino acid sequence of SEQ ID NO:14; or
   C) (a) a VH domain comprising (i) HVR-H1 comprising the amino acid sequence of SEQ ID NO:17, (ii) HVR-H2 comprising the amino acid sequence of SEQ ID NO:18, and (iii) HVR-H3 comprising an amino acid sequence selected from SEQ ID NO:19; and (b) a VL domain comprising (i) HVR-L1 comprising the amino acid sequence of SEQ ID NO:20; (ii) HVR-L2 comprising the amino acid sequence of SEQ ID NO:21 and (iii) HVR-L3 comprising the amino acid sequence of SEQ ID NO:22; or
   D) (a) a VH domain comprising (i) HVR-H1 comprising the amino acid sequence of SEQ ID NO:25, (ii) HVR-H2 comprising the amino acid sequence of SEQ ID NO:26, and (iii) HVR-H3 comprising an amino acid sequence selected from SEQ ID NO:27; and (b) a VL domain comprising (i) HVR-L1 comprising the amino acid sequence of SEQ ID NO:28; (ii) HVR-L2 comprising the amino acid sequence of SEQ ID NO:29 and (iii) HVR-L3 comprising the amino acid sequence of SEQ ID NO:30.
2. The antibody according to embodiment 1, wherein the antibody comprises
   A)
   i) comprises a VH sequence of SEQ ID NO:7 and a VL sequence of SEQ ID NO:8;
   ii) or humanized variant of the VH and VL of the antibody under i); or
   iii) comprises a VH sequence of SEQ ID NO:33 and a VL sequence of SEQ ID NO:34; or
   B)
   comprises a VH sequence of SEQ ID NO:15 and a VL sequence of SEQ ID NO:16; or
   C)
   comprises a VH sequence of SEQ ID NO:23 and a VL sequence of SEQ ID NO:24; or
   D)
   comprises a VH sequence of SEQ ID NO:31 and a VL sequence of SEQ ID NO:32.
3. An isolated antibody that binds to human HLA-G, wherein the antibody
   a) binds to the same epitope as an antibody which comprises a VH sequence of SEQ ID NO:7 and a VL sequence of SEQ ID NO:8;
   or b) binds to the same epitope as an antibody which comprises a VH sequence of SEQ ID NO:31 and a VL sequence of SEQ ID NO:32.
4. The anti-HLA-G antibody according to any one of embodiments 1 to 4, wherein the antibody
   a) does not crossreact with a modified human HLA-G ß2M MHC I complex comprising SEQ ID NO:44; and/or
   b) does not crossreact with human HLA-A2 ß2M MHC I complex comprising SEQ ID NO:39 and SEQ ID NO: 37; and/or
   c) does not crossreact with a mouse H2Kd ß2M MHC I complex comprising SEQ ID NO:45; and/or
   e) does not crossreact with rat RT1A ß2M MHC I complex comprising SEQ ID NO:47; and/or
   f) inhibits ILT2 binding to monomeric HLA-G ß2M MHC I complex (comprising SEQ ID NO: 43); and/or
   g) inhibits ILT2 binding to trimeric HLA-G ß2M MHC I complex (comprising SEQ ID NO: 43), by more than 50% (in one embodiment by more than 60%) (when compared to the binding without antibody) (see Example 4b); and/or
   h) inhibits ILT2 binding to monomeric and/or dimeric and/or trimeric HLA-G ß2M MHC I complex (comprising SEQ ID NO: 43), by more than 50% (in on embodiment by more than 80%) (when compared to the binding without antibody) (see Example 4b); and/or
   i) inhibits ILT2 binding to (HLA-G on) JEG3 cells (ATCC No. HTB36) (by more than 50% (in one embodiment by more than 80%)) (when compared to the binding without antibody) (see Example 6); and/or
   j) binds to (HLA-G on) JEG3 cells (ATCC No. HTB36) (see Example 5), and inhibits ILT2 binding to (HLA-G on) JEG3 cells (ATCC No. HTB36) (by more than 50% (in one embodiment by more than 80%)) (when compared to the binding without antibody) (see Example 6); and/or
   k) inhibits CD8a binding to HLAG by more than 80% (when compared to the binding without antibody) (see e.g., Example 4c); and/or
   l) restores HLA-G specific suppressed immune response (e.g., suppressed Tumor necrose factor (TNF) alpha release) by monocytes co-cultured with JEG-3 cells (ATCC HTB36).
5. The antibody according to any one of the preceding embodiments, wherein the antibody is of IgG1 isotype.
6. The antibody according to embodiment 5, wherein the antibody is of IgG1 isotype with mutations L234A, L235A and P329G (numbering according to the EU index of Kabat).
7. Isolated nucleic acid encoding the antibody according to any one of the preceding embodiments.
8. A host cell comprising the nucleic acid of embodiment 7.
9. A method of producing an antibody comprising culturing the host cell of embodiment 7 so that the antibody is produced.
10. The method of embodiment 9, further comprising recovering the antibody from the host cell.
11. A pharmaceutical formulation comprising the antibody according to any one of embodiments 1 to 6 and a pharmaceutically acceptable carrier.
12. The antibody according to any one of embodiments 1 to 6 for use as a medicament.

13. The antibody according to any one of embodiments 1 to 6 for use in treating cancer.
14. Use of the antibody according any one of embodiments 1 to 6 in the manufacture of a medicament.
15. The use of embodiment 14, wherein the medicament is for treatment of cancer.
16. A method of treating an individual having cancer comprising administering to the individual an effective amount of the antibody of embodiments 1 to 6.
17. A method for selecting anti-HLAG antibodies (e.g., according to embodiments 1 to 6) comprising the following steps:
    a) determining the binding of anti-HLAG antibodies to human HLA-G ß2M MHC I complex comprising SEQ ID NO: 43 by a Surface Plasmon Resonance assay;
    b) determining the inhibition of ILT2 binding to monomeric and/or dimeric and/or trimeric HLA-G ß2M MHC I complex by the respective anti-HLAG antibodies; and
    c) selecting anti-HLAG antibodies which inhibit ILT2 binding to monomeric HLA-G ß2M MHC I complex by more than 50% (in one embodiment by more than 80%) (when compared to the binding without antibody), or selecting anti-HLAG antibodies which inhibit ILT2 binding to monomeric and/or dimeric and/or trimeric HLA-G ß2M MHC I complex by more than 50% (in one embodiment by more than 70%) (when compared to the binding without antibody).
    d) restores HLA-G specific suppressed immune response (e.g., suppressed Tumor necrose factor (TNF) alpha release) by monocytes co-cultured with JEG-3 cells (ATCC HTB36).
18. A method for selecting anti-HLAG antibodies (e.g., according to embodiment 6) comprising the following steps:
    a) determining the binding of anti-HLAG antibodies to JEG3 cells (ATCC No. HTB36) in a flow cytometry assay (using Fluorescence-activated cell sorting) (FACS assay).
    b) determining the inhibition of ILT2 binding to JEG3 cells (ATCC No. HTB36) by the respective anti-HLAG antibodies a flow cytometry assay (using Fluorescence-activated cell sorting) (FACS assay); and
    c) selecting anti-HLAG antibodies which bind to JEG3 (ATCC No. HTB36) cells, and which inhibit ILT2 binding to JEG3 cells (ATCC No. HTB36) by more than 50% (in one embodiment by more than 80%) when compared to the binding without antibody.

EXAMPLES

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Description of the Basic/Standard Mammalian Expression Plasmid

For the expression of a desired gene/protein (e.g., full length antibody heavy chain, full length antibody light chain, or an MHC class I molecule, e.g., HLA-G, or an MHC class I molecule fused to peptide and beta-2 microglobulin, e.g., HLA-G fused to HLA-G binding peptide and or beta-2 microglobulin) a transcription unit comprising the following functional elements is used:
  the immediate early enhancer and promoter from the human cytomegalovirus (P-CMV) including intron A,
  a human heavy chain immunoglobulin 5'-untranslated region (5'UTR),
  a murine immunoglobulin heavy chain signal sequence,
  a gene/protein to be expressed (e.g., full length antibody heavy chain or MHC class I molecule), and
  the bovine growth hormone polyadenylation sequence (BGH pA).

Beside the expression unit/cassette including the desired gene to be expressed the basic/standard mammalian expression plasmid contains
  an origin of replication from the vector pUC18 which allows replication of this plasmid in E. coli, and
  a beta-lactamase gene which confers ampicillin resistance in E. coli.

Protein Determination

The protein concentration of purified polypeptides was determined by determining the optical density (OD) at 280 nm, using the molar extinction coefficient calculated on the basis of the amino acid sequence of the polypeptide.

Example 1

Generation of HLA-G Chimeric Molecules for Screening and Counterscreening

Due to high homology (>98%) with other MHC I molecules, immunisation with HLA-G molecules results in generation of polyclonal sera, composed of a mixture of MHC-I crossreactive antibodies as well as truly HLA-G specific antibodies.

So far, no tools have been provided to select truly HLA-G specific antibodies without crossreactivity to other human MHC-I (e.g., HLA-A), and to further select those with receptor blocking function.

We identified unique HLA-G positions in combination to positions necessary for structural conformity and receptor interaction (ILT2/4 and KIR2DL4.)

Unique and proximal positions of human HLA-G were then "grafted" on MHC class I complex molecules from different rodent species (such as rat RT1A and mouse H2kd) to generate "chimeric" immunogen/screening antigens.

Antibodies generated were subjected to stringent screening for binding/specificity, (and no binding/specificity to counterantigens, respectively).

Screening Antigens:
  rec. HLA-G expressed as human HLA-G ß2M MHC complex comprising SEQ ID NO: 43
  HLA-G specific sequences grafted onto rat RT-1 and mouse H2kd (SEQ ID NO: 46: human HLA-G/mouse H2Kd ß2M MHC class I complex wherein the positions specific for human HLA-G are grafted onto the mouse H2Kd framework and SEQ ID NO: 48: human HLA- G/rat RT1A β2M MHC class I complex wherein the positions specific for human HLA-G are grafted onto the rat RT1A framework)

Natural HLA-G MHC class I complex expressing cells (e.g., Jeg3 cells), or human HLA-G transfected cell lines SKOV3 HLA-G+ and PA-TU-8902 HLA-G+

Screening Counter Antigens:

Counter antigens (MHC class I complexes) with other HLA-A sequences (HLA-A2 and HLA-G$^{degrafted\ with\ HLA-A\ consensus\ sequence}$) combined with different peptides) (see e.g., SEQ ID NO 40 (HLA-A2) and SEQ ID NO: 44 HLA-A consensus sequence on HLA-G framework)

Counter antigens (MHC class I complexes) from other species such as rat RT-1 and mouse H2kd (SEQ ID NO: 45 and SEQ ID NO: 47)

Unmodified tumor cell lines SKOV3 and PA-TU-8902, which are characterized by absence of HLA-G expression.

Design of Chimeric HLA-G Antigens for Use in Immunization and Screening for the Generation of HLA-Specific Antibodies (See FIG. 1):

Design of a chimeric rat MHC I molecule (RT 1-A) carrying HLA-G unique positions (SEQ ID NO: 48) for use in immunization of wildtype (wt) and transgenic rats, or rabbits and mice etc., and/or for use screening assays:

HLA-G unique positions were identified by the alignment of 2579 HLA-A, 3283 HLA-B, 2133 HLA-C, 15 HLA-E, 22 HLA-F, and 50 HLA-G sequences from IMGT (as available on 6 Feb. 2014). Those residues of HLA-G that occur in less than 1% (mostly ~0%) of the sequences of any of the 3 sequence sets HLA-A, HLA-B, and a combined set of HLA-C+HLA-E+HLA-F are called HLA-G unique positions.

The 4 core HLA-G unique positions (2 in alpha-1 and 2 in alpha-3) show no polymorphism in the set of HLA-G sequences and none of the other HLA genes contain the HLA-G specific residues at these positions (except 1×HLA-A for M100, 1×HLA-B for Q103, and 1×HLA-C for Q103).

The crystal structure of rat RT1-A (Rudolph, M. G. et al. J. Mol. Biol. 324: 975-990 (2002); PDB code: 1KJM) was superimposed on the crystal structure of human HLA-G (Clements, C. S. et al. PROC. NATL. ACAD. SCI. USA 102: 3360-3365 (2005); PDB code: 1YDP). The overall structure of the alpha-chain and the associated beta-2-microglobulin is conserved.

HLA-G unique positions were identified in the RT1-A structure by comparison of the sequence and structural alignments. In a first step, unique HLA-G positions were identified that are exposed on the molecular surface of HLA-G and RT1-A and thus accessible for an antibody. Unique positions that are buried within the protein fold were excluded for engineering. In a second step, structurally proximal residues were identified, that also need to be exchanged to make the corresponding region "HLA-G-like", i.e., to generate real HLA-G epitopes containing the unique positions rather than generating HLA-G/rat RT1-A chimeric epitopes that would be artificial. All the positions that were thus selected for mutation were analyzed for structural fit of the respective residue from HLA-G to avoid possible local disturbances of the molecular structure upon mutation.

A chimeric mouse MHC I molecule (H2Kd) carrying HLA-G unique positions (SEQ ID NO: 46) for use in immunization and/or for use screening assays was generated analogously.

Design of HLA-A Based Counter Antigens by "De-Grafting" of HLA-G Unique Positions Towards an HLA-A Consensus Sequence for Use as a Counter-Antigen in Screening (SEQ ID NO:44)

Unique positions derived from the multiple sequence alignment were analyzed in a crystal structure of human HLA-G (PDB code: 1YDP). First, positions that are not exposed on the HLA-G surface and are thus not accessible for an antibody were excluded for engineering. Second, the surface exposed residues were analyzed for feasibility of amino acid exchange (i.e., exclusion of possible local disturbances of the molecular structure upon mutation of the relevant position). In total, 14 positions were validated for exchange. The amino acids in the validated positions were mutated towards an HLA-A consensus sequence derived from a multiple sequence alignment of 2579 HLA-A sequences downloaded from IMGT (as available on 6 Feb. 2014).

Generation of Expression Plasmids for Soluble Classical and Non-Classical MHC Class I Molecules The recombinant MHC class I genes encode N-terminally extended fusion molecules consisting of a peptide known to be bound by the respective MHC class I molecule, beta-2 microglobulin, and the respective MHC class I molecule.

The expression plasmids for the transient expression of soluble MHC class I molecules comprised besides the soluble MHC class I molecule expression cassette an origin of replication from the vector pUC18, which allows replication of this plasmid in *E. coli*, and a beta-lactamase gene which confers ampicillin resistance in *E. coli*.

The transcription unit of the soluble MHC class I molecule comprised the following functional elements:
- the immediate early enhancer and promoter from the human cytomegalovirus (P-CMV) including intron A,
- a human heavy chain immunoglobulin 5'-untranslated region (5'UTR),
- a murine immunoglobulin heavy chain signal sequence,
- an N-terminally truncated *S. aureus* sortase A encoding nucleic acid, and
- the bovine growth hormone polyadenylation sequence (BGH pA).

The amino acid sequences of the mature soluble MHC class I molecules derived from the various species are:
SEQ ID NO: 43: exemplary human HLA-G β2M MHC class I complex
SEQ ID NO: 44: exemplary modified human HLA-G β2M MHC class I complex (wherein the HLA-G specific amino acids have been replaced by HLA consensus amino acids (=degrafted HLA-G see also FIG. 1)
SEQ ID NO: 45: exemplary mouse H2Kd β2M MHC class I complex
SEQ ID NO: 46: exemplary human HLA-G/mouse H2Kd β2M MHC complex wherein the positions specific for human HLA-G are grafted onto the mouse H2Kd framework
SEQ ID NO: 47: exemplary rat RT1A β2M MHC class I complex
SEQ ID NO: 48: exemplary human HLA-G/rat RT1A β2M MHC complex wherein the positions specific for human HLA-G are grafted onto the rat RT1A framework For the exemplary HLA-A2 β2M MHC class I complex used in screening the following components were used and the complex was expressed in *E. Coli* and purified.

MHCI complex HLA-A2/b2M (SEQ ID NOs 40 and 37) (both with an additional N-terminal methionine)+VLD-FAPPGA peptide (SEQ ID NO: 50)+linker and his-Tag (SEQ ID NO: 49)

Example 2

Immunization Campaigns

A) Immunization of Mice and Rats a. Chimeric Proteins (for Tolerance Against Unspecific MHC-I/HLA and Direction to Unique HLA-G Positions)

Balb/C mice obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2531-19-10 and 55.2-1-54-2532-51-11) and performed according to the German Animal Welfare Act and the Directive 2010/63 of the European Parliament and Council.

Balb/C mice (n=5), 6-8 week old, received five rounds of immunization with a chimeric H2Kd/HLA-G molecule (SEQ ID NO: 46 ("HLA-G-0006")) over a course of 4 weeks. Before each immunization, mice were anesthetized with a gas mixture of oxygen and isoflurane. For the first immunization, 15 µg protein dissolved in 20 mM His/HisCl, 140 mM NaCl, pH 6.0, were mixed with an equal volume of CFA (BD Difco, #263810) and administered subcutaneously (s.c.) to six sites proximal to draining lymph nodes, along the back of the mice, with two sites at the nape of the neck and two sites bilaterally to the groin and calf. Another 15 µg of protein emulsified in RIM ADJUVANT® (Sigma-Aldrich, #S6322) was administered to six juxtaposed sites along the abdomen, with two sites each bilaterally to the axilla, groin, and thigh. Descending antigen doses of booster immunizations were given on days 7 (10 µg), 14 (5 µg), 21 (5 µg), and 28 (5 µg) in a similar fashion except RIBI adjuvant was used throughout, and only along the abdomen. Three days after the final immunization, mice were euthanized and the bilateral popliteal, superficial inguinal, axillary, and branchial lymph nodes were isolated aseptically and prepared for hybridoma generation. Serum was tested for recombinant human HLA-G and immunogen-specific total IgG antibody production by ELISA after the third and fifth immunization.

Another set of Balb/C mice (n=5), 6-8 week old, received three immunizations with the chimeric H2Kd/HLA-G molecule (HLA-G-0006) over a course of 3 months. For the first immunization, 100 µg protein dissolved in 20 mM His/HisCl, 140 mM NaCl, pH 6.0, were mixed with an equal volume of CFA (BD Difco, #263810) and administered intraperitoneally (i.p.). Booster immunizations were given on days 28 and 56 in a similar fashion, except that incompletes Freund's adjuvant (IFA from BD Difco, #DIFC263910) was used. Four to five weeks after the final immunization, mice received approximately 25 µg of the immunogen intravenously (i.v.) in sterile PBS and 72 h later, spleens were aseptically harvested and prepared for hybridoma generation. Serum was tested for recombinant human HLA-G (SEQ ID NO: 43 ("HLA-G-0003")), and immunogen-specific chimeric H2Kd/HLA-G molecule (SEQ ID NO: 46 ("HLA-G-0006")) and counterscreened with "degrafted" human HLA-G with consensus HLA-A specific positions (SEQ ID NO: 44 ("HLA-G-0007")) and murine H2kd protein (SEQ ID NO: 45 "HLA-G-0009")) total IgG antibody production by ELISA after the third immunization.

b. Wt HLA-G Protein

CD® rats obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2532-51-11) and performed according to the German Animal Welfare Act and the Directive 2010/63 of the European Parliament and Council.

CD® rats (n=4), 6-8 week old, received four immunizations with recombinant human HLA-G protein (SEQ ID NO: 43 ("HLA-G-0003")) over a course of 4 months. For the first immunization, 100 µg protein dissolved in 20 mM His/HisCl, 140 mM NaCl, pH 6.0, were mixed with an equal volume of CFA (BD Difco, #263810) and administered intraperitoneally. Booster immunizations were given on days 28, 56 and 84 in a similar fashion, except that incompletes Freund's adjuvant (IFA from BD Difco, #DIFC263910) was used throughout. Three to four weeks after the final immunization, rats received approximately 75 µg of the immunogen i.v. in sterile PBS; and 72 h later, spleens were aseptically harvested and prepared for hybridoma generation. Serum was tested for recombinant HLA-G (SEQ ID NO: 43 ("HLA-G-0003"))-specific IgG1, IgG1a, IgG2b and IgG2c antibody production by ELISA after the third and fourth immunization and counterscreened with "degrafted" human HLA-G with consensus HLA-A specific positions (SEQ ID NO: 44 ("HLA-G-0007")).

c. JEG3 Cells (ATCC No. HTB36) (Naturally Expressing HLA-G)

CD® rats obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number AZ. 55.2-1-54-2531-83-13) and performed according to the German Animal Welfare Act and the Directive 2010/63 of the European Parliament and Council.

Two groups of CD® rats (n=2), 6-8 week old, received either five (group A) or seven (group B) immunizations using JEG-3 cells (ATCC HTB36) over a course of five (A) to seven (B) months, respectively. For the first immunization, 1×10⁶cells dissolved in sterile PBS, were mixed with an equal volume of CFA (BD Difco, #263810) and administered intraperitoneally. Booster immunizations were given to A and B on days 28, 56, 84, 112, 140 (B only) and 168 (B only) in a similar fashion, except that incompletes Freund's adjuvant (IFA from BD Difco, #DIFC263910) was used throughout. Three weeks after the final immunization, rats received 100 µg of recombinant human HLA-G protein (SEQ ID NO: 43 ("HLA-G-0003")) i.v. in sterile PBS; and 72 h later, spleens were aseptically harvested and prepared for hybridoma generation. Serum was tested for recombinant HLA-G (SEQ ID NO: 43 ("HLA-G-0003"))-specific IgG1, IgG1a, IgG2b and IgG2c antibody production-specific IgG1, IgG2a, IgG2b and IgG2c antibody production by ELISA after the third, fifth and seventh immunization, respectively and counterscreened with "degrafted" human HLA-G with consensus HLA-A specific positions (SEQ ID NO: 44 ("HLA-G-0007")).

d. JEG3/DNA IMS (for Boosting Effect)

CD® rats obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number AZ. 55.2-1-54-2531-83-13) and performed according to the German Animal Welfare Act and the Directive 2010/63 of the European Parliament and Council.

CD® rats (n=5), 6-8 week old, received plasmid DNA and cell-based immunizations in an alternating regime over a course of three months. The plasmid DNA HLA-G-0030 (p17747) encoding for human HLA-G as a single chain molecule as well as the naturally HLA-G expressing JEG-3 cells (ATCC HTB36) were used for this purpose, respectively.

For the first immunization, animals were isoflurane-anesthetized and intradermally (i.d.) immunized with 100 g plasmid DNA in sterile $H_2O$ applied to one spot at the shaved back, proximal to the animal's tail. After i.d. application, the spot was electroporated using following parameters on an ECM 830 electroporation system (BTX Harvard Apparatus): two times 1000V/cm for 0.1 ms each, separated by an interval of 125 ms, followed by four times 287.5V/cm for 10 ms, separated also by intervals of 125 ms. For the second immunization on day 14, animals received 1×10∂cells dissolved in sterile PBS, that were mixed with an equal volume of CFA (BD Difco, #263810) and, after generation of a stable emulsion, administered intraperitoneally. Booster immunizations were given on days 28 (DNA), 42 (cells), 56 (DNA), 70 (cells) in a similar fashion, except that incompletes Freund's adjuvant (IFA from BD Difco, #DIFC263910) was used for cell immunizations throughout. Four weeks after the final immunization, rats received 100 µg of soluble recombinant human HLA-G MHC class I protein (SEQ ID NO: 43 ("HLA-G-0003")) i.v. in sterile PBS; and 72 h later, spleens were aseptically harvested and prepared for hybridoma generation. Serum was tested for soluble recombinant human HLA-G MHC class I protein (SEQ ID NO: 43 ("HLA-G-0003"))-specific IgG1, IgG2a, IgG2b and IgG2c antibody production by ELISA after the third, fifth and sixth immunization, respectively and counterscreened with "degrafted" human HLA-G with consensus HLA-A specific positions (SEQ ID NO: 44 ("HLA-G-0007")).

In all immunization strategies a highly polyreactive humoral immune response was induced, recognizing HLA-G, as well as proteins used for counterscreening (e.g., recombinant "degrafted" human HLA-G, chimeric H2Kd/HLA-G molecule or related human HLA-A2 molecules) as analyzed in an ELISA format using polyclonal sera from immunized animals (no data shown).

B) Immunization of Humanized OMNIRAT® Line 7 Rats

OMNIRAT® Line 7 rats were partnered from Open Monoclonal Technology, Inc. (2747 Ross Road, Palo Alto, Calif. 94303, USA) and were bred and obtained from Charles River Laboratories International, Inc. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2532-51-11 and 55.2-1-54-2531-83-13) and performed according to the German Animal Welfare Act and the Directive 2010/63 of the European Parliament and Council.

OMNIRAT® Line 7 rats (n=4), 6-8 week old, received four immunizations with recombinant chimeric HLA-G protein (SEQ ID NO: 48 ("HLA-G-0011")) over a course of 4 months. For the first immunization, 100 µg protein dissolved in 20 mM His/HisCl, 140 mM NaCl, pH 6.0, were mixed with an equal volume of CFA (BD Difco, #263810) and administered intraperitoneally. Booster immunizations were given on days 28, 56 and 84 in a similar fashion, except that incompletes Freund's adjuvant (IFA from BD Difco, #DIFC263910) was used throughout. Three to four weeks after the final immunization, rats received approximately 50p g of the immunogen i.v. and 25 µg of the immunogen i.p. in sterile PBS and 72 hrs later, spleens were aseptically harvested and prepared for hybridoma generation. Serum was tested for recombinant HLA-G (SEQ ID NO: 48 ("HLA-G-0011"))-specific IgG1, IgG2a, IgG2b and IgG2c antibody production by ELISA after the third and fourth immunization and counterscreened with "degrafted" human HLA-G with consensus HLA-A specific positions (SEQ ID NO: 44 ("HLA-G-0007")).

Alternatively, OMNIRAT® Line 7 rats (n=5), 6-8 week old, received plasmid DNA and cell-based immunizations in an alternating regime over a course of three months. The plasmid DNA encoding for human HLA-G as a single chain molecule (human HLA-G MHC class I protein (SEQ ID NO: 43 ("HLA-G-0003")) as well as the naturally HLA-G expressing JEG-3 cells (ATCC HTB36) were used for this purpose, respectively.

For the first immunization, animals were isoflurane-anesthetized and intradermally (i.d.) immunized with 100 µg plasmid DNA in sterile $H_2O$ applied to one spot at the shaved back, proximal to the animal's tail. After i.d. application, the spot was electroporated using following parameters on an ECM 830 electroporation system (BTX Harvard Apparatus): two times 1000V/cm for 0.1 ms each, separated by an interval of 125 ms, followed by four times 287.5V/cm for 10 ms, separated also by intervals of 125 ms. For the second immunization on day 14, animals received 1×10∂cells dissolved in sterile PBS, that were mixed with an equal volume of CFA (BD Difco, #263810) and, after generation of a stable emulsion, administered intraperitoneally. Booster immunizations were given on days 28 (DNA), 42 (cells), 56 (DNA), 70 (cells) in a similar fashion, except that incompletes Freund's adjuvant (IFA from BD Difco, #DIFC263910) was used for cell immunizations throughout. Four weeks after the final immunization, rats received 100 µg of soluble recombinant human HLA-G MHC class I protein (SEQ ID NO: 43 ("HLA-G-0003")) i.v. in sterile PBS; and 72 h later, spleens were aseptically harvested and prepared for hybridoma generation. Serum was tested for soluble recombinant human HLA-G MHC class I protein (SEQ ID NO: 43 ("HLA-G-0003"))-specific IgG1, IgG2a, IgG2b and IgG2c antibody production by ELISA after the third, fifth and sixth immunization, respectively and counterscreened with "degrafted" human HLA-G with consensus HLA-A specific positions (SEQ ID NO: 44 ("HLA-G-0007")).

In all immunization strategies a highly polyreactive humoral immune response was induced, recognizing HLA-G, as well as proteins used for counterscreening (e.g., recombinant "degrafted" human HLA-G, chimeric H2Kd/HLA-G molecule or related human HLA-A2 molecules) as analyzed in an ELISA format using polyclonal sera from immunized animals (no data shown).

Obtained Antibodies

Using the above methods, the following antibodies which specifically bind to human anti-HLA-G were obtained: rat HLA-G 0031 from CD® rats, human HLAG 0039, HLA-G 0041 and HLA-G 0090 from humanized rats.

Binding properties of the obtained anti-HLA-G specific antibodies and biological activities were determined as described in the following Examples and compared to known reference antibodies. Antibody HLA-G-0031 was humanized using its HVRs and VH acceptor human framework of HUMAN_IGHV1-3 and VL acceptor human frameworks HUMAN_IGKV1-17 (V-domain, with one additional back-mutation at position R46F, Kabat numbering).

For the identification of a suitable human acceptor framework during the humanization of the HLAG binder HLAG-0031 a combination of two methodologies was used. On the one hand a classical approach was taken by searching for an acceptor framework with high sequence homology to the parental antibody and subsequent in silico grafting of the CDR regions onto this acceptor framework. Each amino acid difference of the identified frameworks to the parental antibody was judged for impact on the structural integrity of the binder and backmutations towards the parental sequence were considered whenever appropriate.

On the other hand, an in silico tool described in WO 2016/062734 was used to predict the orientation of the VH and VL domains of the humanized versions towards each other. This was carried out for the virtual grafts of the CDRs on all possible human germline combinations. The results were compared to the VH VL domain orientation of the parental binder to select for framework combinations which are close in geometry to the starting antibody.

Anti-HLAG Antibody Antibodies (SEQ ID Nos of Variable Regions and Hypervariable Regions (HVRs)):

| Anti-HLAG antibody | HVR-H1 | HVR-H2 | HVR-H3 | HVR-L1 | HVR-L2 | HVR-L3 | VH | VL |
|---|---|---|---|---|---|---|---|---|
| HLA-G-0031 | SEQ ID NO: 1 | SEQ ID NO: 2 | SEQ ID NO: 3 | SEQ ID NO: 4 | SEQ ID NO: 5 | SEQ ID NO: 6 | SEQ ID NO: 7 | SEQ ID NO: 8 |
| HLA-G-0031-0104 (humanized variant of HLA-G-0031) (HLA-G-0104) | SEQ ID NO: 1 | SEQ ID NO: 2 | SEQ ID NO: 3 | SEQ ID NO: 4 | SEQ ID NO: 5 | SEQ ID NO: 6 | SEQ ID NO: 33 | SEQ ID NO: 34 |
| HLA-G-0039 | SEQ ID NO: 9 | SEQ ID NO: 10 | SEQ ID NO: 11 | SEQ ID NO: 12 | SEQ ID NO: 13 | SEQ ID NO: 14 | SEQ ID NO: 15 | SEQ ID NO: 16 |
| HLA-G-0041 | SEQ ID NO: 17 | SEQ ID NO: 18 | SEQ ID NO: 19 | SEQ ID NO: 20 | SEQ ID NO: 21 | SEQ ID NO: 22 | SEQ ID NO: 23 | SEQ ID NO: 24 |
| HLA-G-0090 | SEQ ID NO: 25 | SEQ ID NO: 26 | SEQ ID NO: 27 | SEQ ID NO: 28 | SEQ ID NO: 29 | SEQ ID NO: 30 | SEQ ID NO: 31 | SEQ ID NO: 32 |

Example 3

A) Binding of Anti HLA-G Antibodies to Soluble Human HLA-G, Soluble Degrafted Human HLA-G with HLA-A Specific Sequence, Human HLA-A2, and Rat/Mouse H2-Kd Antibodies obtained from immunisation were screened for their binding properties to human, HLA-G, chimeric, degrafted HLA-G, HLA-A2 and rat/mouse H2-Kd. The respective assays are described below. For the testing of human HLA-G either monomeric, as well as dimeric and trimeric forms were used (see preparation below).

Dimerization/Trimerization of Human HLA-G MHC Class I Protein

Supernatant containing monomeric His tagged soluble human HLA-G MHC class I protein (SEQ ID NO: 23) was loaded on to a HisTrap™ HP column (GE Healthcare #17-5248-02) with 5 ml Ni-Sepharose at the flow rate of 0.2 ml/min overnight at room temperature using an ÄKTA FPLC™ Column was then washed with 2% DPBS containing 0.5M Imidazole (Merck #8.14223.025) until baseline was reached. Column was then equilibrated with 10 mM DTT in 2% DPBS containing 0.5M Imidazole and incubated for 30 min at room temperature. DTT was washed out from the column with PBS/10 mM Imidazole and the protein was eluted at a gradient of 2-100% DPBS with 0.5 mM Imidazole. After concentrating the eluate using AMICON® Ultra 15 M/Ultracel® 10K, the protein was incubated for 24 hours at room temperature followed by 48 hours at 4° C. to allow dimer/multimerization. Separation of the dimers and trimers was then performed using SEC in Superdex® 200 HILOAD® 16/60 (GE Healthcare #17-5175-01) and washed with 0.5M NaOH overnight. The column was equilibrated with PBS followed by saturation with 10 mg/ml BSA. The dimers (fraction A9) and the trimers (fraction A8) were then collected, aliquoted and stored at −80° C. till further use.

Human Wt HLA-G Binding ELISA

Streptavidin coated plates (Nunc™, MicroCoat #11974998001) were coated with 25 µl/well biotinylated human wt HLA-G at a concentration of 250 ng/ml and incubated at 4° C. overnight. After washing (3×90 µl/well with PBST-buffer) 25 µl anti-HLA-G samples (1:3 dilution in OSEP buffer) or reference antibody (G233, Thermo/Pierce #MA1-19449, 500 ng/ml) were added and incubated 1 h at RT. After washing (3×90 µl/well with PBST-buffer) 25 µl/well goat-anti-mouse H+L-POD (Biorad #170-6561, 1:2000 in OSEP) or donkey-anti-rabbit IgG POD (GE #NA9340V, 1:5000 in OSE) was added and incubated at RT for 1 h on shaker. For detection of rat IgGs a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (6×90 µl/well with PBST-buffer) 25 µl/well TMB substrate (Roche, 11835033001) was added and incubated until OD 2-3. Measurement took place on a Tecan SAFIRE 2™ instrument at 370/492 nm.

Human Degrafted HLA-G with HLA-A Specific Sequences Binding ELISA

Streptavidin coated plates (Nunc™, MicroCoat #11974998001) were coated with 25 µl/well biotinylated human degrafted HLA-G at a concentration of 250 ng/ml and incubated at 4° C. overnight. After washing (3×90 µl/well with PBST-buffer) 25 µl anti-HLA-G samples (1:3 dilution in OSEP buffer) or rat serum (1:600 dilution in OSEP) were added and incubated 1 h at RT. After washing (3×90 µl/well with PBST-buffer) 25 µl/well of a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (6×90 µl/well with PBST-buffer) 25 µl/well TMB substrate (Roche, 11835033001) was added and incubated until OD 2-3. Measurement took place on a Tecan SAFIRE 2™ instrument at 370/492 nm.

Rat MHC I (RT1-A) Binding ELISA

Streptavidin coated plates (NUNC™, MicroCoat #11974998001) were coated with 25 µl/well biotinylated rat MHC I (RT1-A) at a concentration of 250 ng/ml and incubated at 4° C. overnight. After washing (3×90 µl/well with PBST-buffer) 25 µl anti-HLA-G samples (1:3 dilution in OSEP buffer) or rat serum (1:600 dilution in OSEP) were added and incubated 1 h at RT. After washing (3×90 µl/well with PBST-buffer) 25 µl/well of a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (6×90 µl/well with PBST-buffer) 25 µl/well TMB substrate (Roche, 11835033001) was added and incubated until OD 2-3. Measurement took place on a Tecan SAFIRE 2™ instrument at 370/492 nm.

HLA-A2 Binding ELISA

Streptavidin coated plates (NUNC™, MicroCoat #11974998001) were coated with 25 µl/well biotinylated human HLA-A2 at a concentration of 250 ng/ml and incubated at 4° C. overnight. After washing (3×90 µl/well with PBST-buffer) 25 µl anti-HLA-G samples (1:3 dilution in OSEP buffer) or rat serum (1:600 dilution in OSEP) were added and incubated 1 h at RT. After washing (3×90 µl/well with PBST-buffer) 25 µl/well of a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on a shaker. After washing (6×90 µl/well with PBST-buffer) 25 µl/well TMB substrate (Roche, 11835033001) was added and incubated until OD 2-3. Measurement took place on a Tecan SAFIRE 2™ instrument at 370/492 nm.

Binding Kinetics of Anti-HLA-G Antibodies

Binding kinetics of anti-HLA-G antibodies to human HLA-G, human HLA-G degrafted and human HLA-A2 were investigated by surface plasmon resonance using a BIACORE® T200 instrument (GE Healthcare). All experiments were performed at 25° C. using PBS Buffer (pH 7.4+0.05% Tween20™) as running buffer and PBS Buffer (+0.1% BSA) as dilution buffer. Anti-human Fc (JIR009-005-098, Jackson) or anti-rat Fc (JIR112-005-071, Jackson) or anti-Mouse Fc (JIR115-005-071, Jackson) antibodies were immobilized on a Series S CM5 Sensor Chip (GE Healthcare) at pH 5.0 by using an amine coupling kit supplied by GE Healthcare. Anti-HLA-G antibodies were captured on the surface leading to a capturing response of 50-200 RU. HLA-G molecules were injected for 180 s at 30 µl/min with concentrations from 2.5 up to 800 nM (2×1:2 and 4×1:3 dilution series) onto the surface (association phase). The dissociation phase was monitored for 300-600 sec by washing with running buffer. The surface was regenerated by injecting H3PO4 (0.85%) for 60+30 seconds for anti-human Fc capturing antibodies, glycine pH1.5 for 60 seconds and glycine pH2.0 for 60 seconds for anti-rat Fc capturing antibodies, H3PO4 (0.85%) for 80+60 seconds for anti-mouse Fc capturing antibodies. Bulk refractive index differences were corrected by subtracting the response obtained from a mock surface. Blank injections were subtracted (double referencing). The derived curves were fitted to a 1:1 Langmuir binding model using the BIAevaluation software.

Cross-Blocking of Anti-HLA-G Antibodies

Cross-blocking experiments of anti-HLA-G antibodies binding to human HLA-G were investigated by surface plasmon resonance using a BIACORE® T200 or B4000 instrument (GE Healthcare). All experiments were performed at 25° C. using PBS Buffer (pH 7.4+0.05% Tween20™) as running buffer.

Anti-human Fab (GE-Healthcare, 28-9583-25) antibodies were immobilized on a Series S CM5 Sensor Chip (GE Healthcare) according to the protocol of the provider, to capture antibodies from OMT rats that contain a human Ck Domain. Anti-HLA-G antibodies were captured for 70 s at a concentration of 15 µg/ml. Wt HLA-G was injected (30 µl/min) at a concentration of 500 or 1000 nM for 60 seconds. Wt rat-antibody was then injected for 90 seconds at a concentration of 30 µg/ml. The dissociation phase was monitored for 60 or 240 sec by washing with running buffer. The surface was regenerated by injecting Glycine pH 1.5 for 60 seconds and an additional stabilization period of 90 sec.

In another assay setup, Anti-human Fab (GE-Healthcare, 28-9583-25) antibodies were immobilized on a Series S CM5 Sensor Chip (GE Healthcare) according to the protocol of the provider, to capture antibodies from OMT rats that contain a human Ck Domain. Anti-HLA-G antibodies were captured for 90 s at a concentration of 30 µg/ml. Unoccupied binding sites on the capture antibodies were blocked by 4×120 sec. injection of human IgG (JIR009-000-003) at a concentration of 500 µg/ml and a flow rate of 30 µl/min. Wt HLA-G was injected (30 µl/min) at a concentration of 500 nM for 90 seconds. The second antibody from OMT rats (human Ck Domain) was then injected for 90 seconds at a concentration of 30 µg/ml. The dissociation phase was monitored for 240 sec by washing with running buffer. The surface was regenerated by injecting Glycine pH 1.5 for 60 seconds and an additional stabilization period of 90 sec.

TABLE

Binding of HLA-G antibodies to recombinant soluble HLA-G MHC class 1 complex, in its monomeric, dimeric and trimeric form (ELISA)

| antibody | HLA-G Monomer EC50 [nM] | HLA-G Dimer EC50 [nM] | HLA-G Trimer EC50 [nM] |
|---|---|---|---|
| HLA-G-0031 | 7.19 | 1.87 | 1.86 |
| HLA-G-0039 | 7.35 | 4.10 | 5.29 |
| HLA-G-0041 | 4.95 | 5.31 | 4.87 |
| HLA-G-0090 | n.a. | n.a. | n.a. |

The above table summarizes the binding of different rat anti-human HLA-G monoclonal antibodies, derived from wt protein IMS. Shown are the relative EC50 values [ng/ml] of the respective binding to rec. wt monomeric, dimeric and trimeric HLA-G proteins as assessed by ELISA. The ELISA was set up by coating the biotinylated wt HLA-G antigen to streptavidin plates. After incubation and washing steps, the respective antibodies were bound in a concentration range from 10-0 µg in 1:2 dilution steps. Detection of bound antibodies was carried out by anti-Fc-antibody-POD conjugates. EC50 values were determined from the resulting binding curves at the antibody concentrations generating the half-maximal signal. In the case of the non-biotinylated HLA-G dimer and trimer antigens, immobilization was carried out by random coating on assay plates.

HLA-G wt versus HLA-G degraft binding ELISA:

| Antibody | wt HLA-G (SEQ ID NO: 43) (monomer) | | HLA-A consensus on HLA-G degraft (SEQ ID NO: 44) | |
|---|---|---|---|---|
| | EC50 rel [ng/ml] | Max. OD | EC50 rel [ng/ml] | Max. OD |
| HLA-G-0031 | 7.19 | 1.6 | — | 0.13 |
| HLA-G-0039 | 7.35 | 1.4 | — | 0.13 |
| HLA-G-0041 | 8.60 | 2.3 | — | 0.15 |
| HLA-G-0090 | 10.37 | 3.4 | — | 0.2 |

The above table summarizes the binding of different rat anti-human HLA-G monoclonal antibodies, derived from wt protein IMS both of wt as well as OMT rats. Shown are the relative EC50 values [ng/ml] and maximal OD of the respective binding to rec. wt monomeric HLA-G protein or the so-called degrafted HLA-G (HLA-A consensus sequence on HLA-G backbone) protein as assessed by ELISA. The ELISA was set up by coating the biotinylated wt HLA-G or consensus antigen to streptavidin plates. After incubation and washing steps, the respective antibodies were bound in a concentration range from 10-0 µg in 1:2 dilution steps. Detection of bound antibodies was carried out by anti-Fc-antibody-POD conjugates. EC50 values were determined from the resulting binding curves at the antibody concentrations generating the half-maximal signal.

HLA-G Wt Versus HLA-G Degraft Binding—Surface Plasmon Resonance

Binding Affinities for HLA-G Antibodies to Recombinant HLA-G (SEQ ID NO:43) and Control Modified Human HLA-G 82M MHC Class I Complex (Wherein the HLA-G Specific Amino Acids have been Replaced by HLA-A Consensus Amino Acids (=Degrafted HLA-G SEQ ID NO: 44) ("-" Indicates No Detectable Binding)

| Anti-body | wt HLA-G (SEQ ID NO: 25) (monomer) | | | | HLA-A consensus on HLA-G degraft (SEQ ID NO: 26) | | | |
|---|---|---|---|---|---|---|---|---|
| | ka (1/Ms) | kd (1/s) | t 1/2 (min) | KD (M) | ka (1/Ms) | kd (1/s) | t 1/2 (min) | KD (M) |
| HLA-G-0031 | 4.9E+04 | 3.7E−03 | 3 | 7.5E−08 | — | — | — | — |
| HLA-G-0031-0104 (humanized) | 8.3E+04 | 2.0E−03 | 6 | 2.4E−08 | | | | |
| HLA-G-0039 | 4.6E+05 | 4.4E−04 | 27 | 9.5E−10 | — | — | — | — |
| HLA-G-0041 | 3.8E+05 | 4.9E−04 | 23 | 1.3E−09 | — | — | — | — |
| HLA-G-0090 | 2.3E+05 | 8.5E−04 | 14 | 3.6E−09 | — | — | — | — |

The above table summarizes the antibody affinities and t½ values against wt and degrafted HLA-G as assessed by Surface plasmon resonance (Biacore®) analysis.

Binding kinetics of anti-HLA-G antibodies to human HLA-G and human HLA-G degrafted were investigated by surface plasmon resonance using a BIACORE® T200 instrument (GE Healthcare). All experiments were performed at 25° C. using PBS Buffer (pH 7.4+0.05% Tween20™) as running buffer and PBS Buffer (+0.1% BSA) as dilution buffer. Anti-human Fc (JIR009-005-098, Jackson) or anti-rat Fc (JIR112-005-071, Jackson) or anti-Mouse Fc (JIR115-005-071, Jackson) antibodies were immobilized on a Series S CM5 Sensor Chip (GE Healthcare) at pH 5.0 by using an amine coupling kit supplied by GE Healthcare. Anti-HLA-G antibodies were captured on the surface leading to a capturing response of 50-200 RU. Non-biotinylated HLA-G molecules were injected for 180 s at 30 µl/min with concentrations from 2.5 up to 800 nM (2×1:2 and 4×1:3 dilution series) onto the surface (association phase). The dissociation phase was monitored for 300-600 sec by washing with running buffer. The surface was regenerated by injecting H3PO4 (0.85%) for 60+30 seconds for anti-human Fc capturing antibodies, glycine pH 1.5 for 60 seconds and glycine pH2.0 for 60 seconds for anti-rat Fc capturing antibodies, H3PO4 (0.85%) for 80+60 seconds for anti-mouse Fc capturing antibodies. Bulk refractive index differences were corrected by subtracting the response obtained from a mock surface. Blank injections were subtracted (double referencing). The derived curves were fitted to a 1:1 Langmuir binding model using the BIAevaluation software ("-" in the table above indicates that no binding could be detected).

In a further experiment the following reference antibodies (obtained from different commercial vendors) were compared for binding to monomeric human HLA-G MHC I (SEQ ID NO: 43 ("HLA-G-0003")) and "degrafted" human HLA-G with consensus HLA-A specific positions (SEQ ID NO: 44 ("HLA-G-0007")):

MEM/G9, 87G, G233, 2A12, 4H184, 5A6G7, 6D463, 9-1F10, MEM-G/1, MEM-Gill, MEM-G/2 and MEM-G/4 ("-" Indicates No Detectable Binding).

| Antigen | Antibody | ka (1/Ms) | kd (1/s) | t 1/2 (Min) | KD (M) |
|---|---|---|---|---|---|
| wt HLA-G (SEQ ID NO: 43) | MEM/G9 | 1.5E+05 | 1.1E−03 | 10 | 7.7E−09 |
| | 87G | — | — | — | — |
| | G233 | 1.8E+05 | 3.7E−03 | 3 | 2.0E−08 |

-continued

| Antigen | Antibody | ka (1/Ms) | kd (1/s) | t 1/2 (Min) | KD (M) |
|---|---|---|---|---|---|
| (monomer) | 2A12 | — | — | — | — |
| | 4H84 | — | — | — | — |
| | 5A6G7 | — | — | — | — |
| | 6D463 | — | — | — | — |
| | 9-1F10 | — | — | — | — |
| | MEM-G/1 | — | — | — | — |
| | MEM-G/11 | 7.4E+04 | 8.5E−04 | 14 | 1.2E−08 |
| | MEM-G/2 | — | — | — | — |
| | MEM-G/4 | — | — | — | — |

-continued

| Antigen | Antibody | ka (1/Ms) | kd (1/s) | t 1/2 (Min) | KD (M) |
|---|---|---|---|---|---|
| HLA-A consensus on HLA-G degraft (SEQ ID NO: 44) | MEM/G9 | 1.2E+05 | 3.6E−02 | 0.3 | 3.0E−07 |
| | 87G | — | — | — | — |
| | G233 | — | — | — | — |
| | 2A12 | — | — | — | — |
| | 4H84 | — | — | — | — |
| | 5A6G7 | — | — | — | — |
| | 6D463 | — | — | — | — |
| | 9-1F10 | — | — | — | — |
| | MEM-G/1 | — | — | — | — |
| | MEM-G/11 | 8.9E+04 | 1.2E−03 | 10 | 1.3E−08 |
| | MEM-G/2 | — | — | — | — |
| | MEM-G/4 | — | — | — | — |

Interestingly, most of the measured antibodies did not show any specific binding to monomeric human HLA-G MHC I (SEQ ID NO: 43 ("HLA-G-0003")) including also antibody 87G. The binding to oligomeric forms of HLA-G as described in literature might be avidity driven due to the increased binding sites of oligomeric forms.

Only antibody MEM/G9 with a KD value of the binding affinity of $7.7E^{-09}$ M, antibody G233 with a KD value of $2.0E^{-08}$ M and MEM-G/11 with a KD value of the binding affinity of $1.2E^{-08}$ M showed binding to monomeric wt human HLA-G MHC I complex. However, one of these antibodies MEM-G/11 also showed some binding/crossreactivity to HLA-A consensus on HLA-G degraft (SEQ ID NO:44).

In addition, another antibody (MEM/G9) also showed stronger unspecific binding to HLA-A consensus on HLA-G degraft (SEQ ID NO:44).

Example 4 a) Receptor Binding Inhibition (with Mono-, Di- and Trimeric HLA-G): ILT-2 and ILT-4 Blocking ELISA Streptavidin coated plates (NUNC™, MicroCoat #11974998001) were coated with 25 µl/well biotinylated human wt HLA-G at a concentration of 500-1000 ng/ml and incubated at 4° C. overnight. After washing (3×90 µl/well with PBST-buffer) 25 µl anti-HLA-G samples were added in decreasing concentrations starting at 10 or 3 µg/ml, then diluted in 1:3 or 1:2 steps and incubated 1 h at RT. After washing (3×90 µl/well with PBST-buffer) 25 µl/well c-myc-tagged recombinant ILT-2 receptor was added at a concentration of 200 ng/ml and incubated for 1 h at room temperature. After washing (3×90 µl/well with PBST-buffer) 25 µl/well goat-anti-c-myc-POD (Bethyl #A190-104P 1:7000 in PBST+0.5% BSA) or anti humanFcgPOD (JIR, 109-036-098, 1:8000 in PBST+0.5% BSA) was added and incubated at RT for 1 h on a shaker. After washing (3×90 µl/well with PBST-buffer), 25 µl/well TMB substrate (Roche, 11835033001) was added and incubated until OD 2-3. Measurement took place on a Tecan SAFIRE 2™ instrument at 370/492 nm.

| Candidate | % inh. ILT2 (3 µg/ml antibody) | % inh. ILT4 (3 µg/ml antibody) |
|---|---|---|
| HLA-G-0031 | 72.8 | 39.8 |
| HLA-G-0039 | 14.0 | 23.9 |
| HLA-G-0041 | 17.4 | 18.4 |
| HLA-G-0090 | 100 | Not tested |

The table above summarizes the extent of ILT-2 and ILT-4 blocking of different antibodies bound to HLA-G at a concentration of 3 µg/ml, relative to an HLA-G:receptor interaction that is not blocked. HLA-G-0090 was tested in a separate experiment for ILT2 blockade, ILT4 blocking was not assessed.

b) Biochemical Comparison of Anti-HLA-G Antibodies for their ILT2 and -4 Binding Inhibition Properties Using a Different Assay Set-Up The ELISA was set up by coating the Fc tagged ILT2 and ILT4 respectively to MAXISORP™ microtiter plates. After incubation and washing steps, the respective antibodies were added at a concentration of 100 nM. Soluble His tagged monomeric, dimeric or trimeric HLA-G was added to the wells. After incubation and washing steps, detection of bound receptor was carried out by anti-His-antibody-POD conjugates. Percentage inhibition (%) was calculated in comparison to values obtained from wells with ILT2/4+ HLA-G (mono-, di-, or Trimer) without anti HLA-G or ILT2/4 antibodies (100% binding=0% inhibition).

| | % inhibition of ILT2 binding | | | % inhibition of ILT4 binding | | |
|---|---|---|---|---|---|---|
| Antibody | Monomer | Dimer | Trimer | Monomer | Dimer | Trimer |
| HLAG-0031 | 101 | 99 | 100 | 17 | 54 | 68 |
| HLAG-0039 | −450 | 25 | 70 | −224 | −105 | −43 |
| HLAG-0041 | −437 | 23 | 67 | −184 | −113 | −39 |
| HLAG-0090* | 92 | 100 | 99 | 31 | 31 | 47 |
| MEM-G/9 | −442 | 1 | 4 | −14 | −44 | −40 |
| 87G | −49 | 19 | 29 | 13 | 18 | 14 |
| G233 | 12 | −132 | 3 | −898 | −20 | 58 |
| anti-ILT2/ILT4 | 113 | 100 | 101 | 44 | 60 | 60 |

The above tables summarize the blocking of interaction between rec. HLA-G proteins (monomer and oligomers) to its receptors ILT2 and ILT4 by the described HLAG antibodies at a concentration of 110 nM (*HLAG-0090 was tested at a concentration of 44 nM) as assessed by ELISA. Shown are the % inhibitions of the HLA-G/receptor interaction (for ILT2 and ILT4). The less pronounced ILT4 inhibition depends on the major ß2M dependent interaction of this receptor.

Figure 4B:
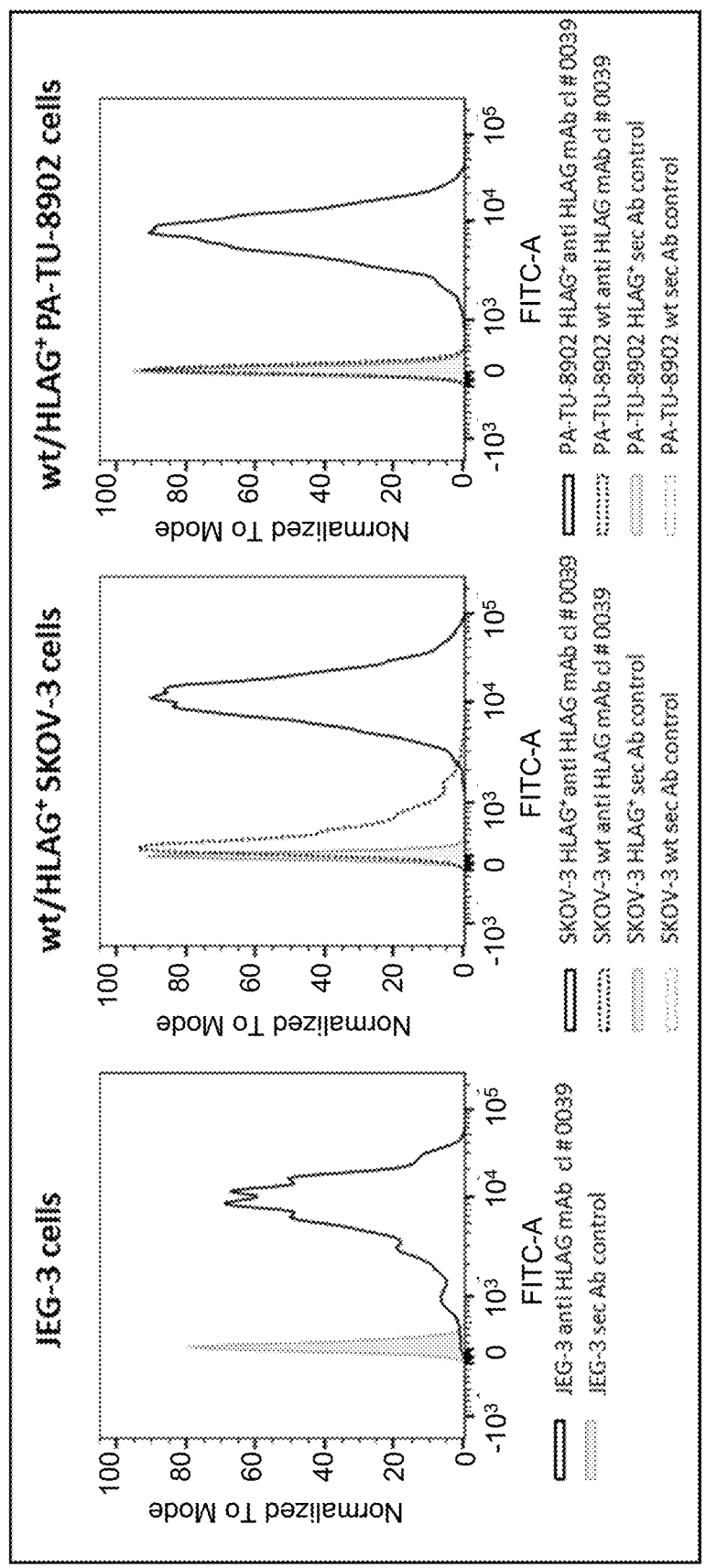

The bar graphs in FIGS. 4A and 4B show % inhibition achieved by the described anti-HLA-G antibodies in comparison to commercially available antibodies. Commercially available HLA-G antibodies 87G, MEM/G09 and G233 do not block HLA-G/ILT2 or ILT4 interaction as efficiently as the described antibodies. Further, the commercially available antibodies lead to increased binding of HLA-G to ILT2 or ILT4 upon binding in some cases.

c) Inhibition of CD8a Binding to HLAG by Anti-HLAG Antibodies

Streptavidin coated 384 well plates were blocked with 30 µl/well of blocking solution. Blocking solution prepared by diluting 5% Polyvinylalcohol (PVA, Sigma #P8136) and 8% Polyvinylpyrrolidone (PVP, Sigma #PVP360) 1:10 in Starting block T20 (Thermo Scientific #37543) by adding 3.5 ml PVA+3.5 ml and PVP to 35 ml Starting Block T20. 30 µl of Biotinylated HLAG (3 µg/ml) diluted in blocking solution were added to each well and incubated at room temperature for 1 hour on a shaker. Wells were washed 3 times with 100 µl of PBS (PAN Biotech #P04-36500) containing 0.1% Tween-20™ (Merck #8.22184.500). The wells were then incubated with 30 µl of anti-HLAG antibodies diluted in blocking buffer in triplicates for 1 hour at room temperature on a shaker and then washed 3 times with 100 µl of PBS containing 0.1% Tween-20™. Recombinant CD8a (Sino Biological #10980-H08H, reconstituted at stored for 1 week at 4° C.) was diluted in blocking solution (1.25 µg/ml), and 30 µl were added to all the wells and incubated for 2 hours at room temperature on a shaker. Wells were washed 3 times with 100 µl of PBS containing 0.1% Tween-20™. HRP conjugated polyclonal anti-CD8a rat IgG antibody (USBiological #033547-HRP) was diluted in 3% Bovine Serum Albumin Fraction V (Roche #10735086001)/PBS 0.2% Tween20™ and 30 µl of this dilution was added to each well. The plate was then incubated for 1 hour at room temperature on a shaker and washed 3 times with 100 µl of PBS containing 0.1% Tween-20™. 30 µl of TMB substrate (BM-Blue, soluble HRP substrate, Roche #11484281001) was then added to each well followed by 25 minutes of incubation at room temperature on a shaker. The reaction was then stopped by adding 25 µl of sulfuric acid to each well and the absorbance as measured at 450 nM in a plate reader. Specific binding of CD8a to HLAG was calculated by subtracting the average of the background values form the average of the binding values. Total binding of CD8 to HLAG in the absence of antibodies was considered 100% binding or 0% inhibition.

Figure 4C:
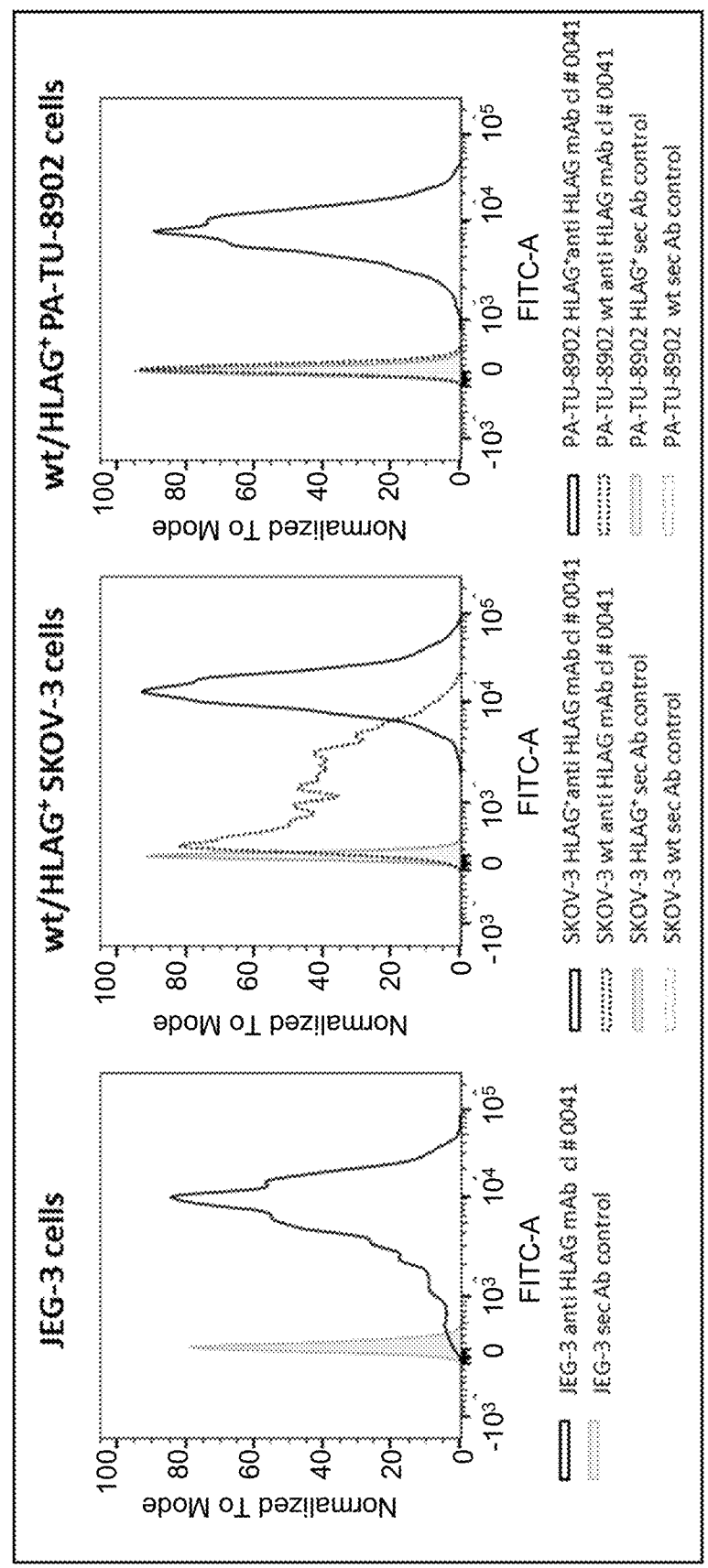

The bar graph in FIG. 4C shows % inhibition achieved by the described anti-HLA-G antibodies in comparison to commercially available antibodies. Commercially available HLA-G antibodies 87G do not block HLA-G/CD8a interaction, whereas MEM/G09 and G233 partially inhibit HLAG interaction with CD8a compared to described antibodies in this set up.

Example 5

Binding of Anti HLA-G Antibodies to Cells
a) Cell-Surface HLA-G Binding ELISA

25 µl/well of JEG3 cells (naturally expressing HLA-G, 20000 cells/well), Skov-3 cells or Skov-3 cells expressing recombinant HLA-G on the cell surface (both 10000 cells/well) were seeded into tissue culture treated 384-well plates (Corning, 3701) and incubated at 37° C. overnight. The next day 12.5 µl of anti-HLA-G samples (final dilution 1:3) were added and incubated for 2 h at 4° C. Cells were fixed by addition of 50 µl/well glutaraldehyde to a final concentration of 0.05% (Sigma Cat. No: G5882; Lot No.: 056K5318). After washing (3×90 µl/well with PBST-buffer) 25 µl/well goat-anti-mouse H+L-POD (Biorad #170-6561 1:2000 in OSEP) or donkey-anti-rabbit IgG POD (GE #NA9340V, 1:5000 in OSE) was added and incubated at RT for 1 h on shaker. For detection of rat IgGs a mixture of goat-anti-rat IgG1-POD (Bethyl #A110-106P), goat-anti-rat IgG2a-POD (Bethyl #A110-109P) and goat-anti-rat IgG2b-POD (Bethyl #A110-111P) 1:10000 in OSEP was added and incubated at RT for 1 h on shaker. After washing (4×90 µl/well with PBST-buffer) 25 µl/well TMB substrate (Roche, 11835033001) was added and incubated until OD 2-3. Measurement took place on a Tecan SAFIRE 2™ instrument at 370/492 nm.

| Antibody | Jeg3 | wt Skov3 | HLA-G+ Skov3 | wt PA-TU-8902 | HLA-G+ PA-TU-8902 |
|---|---|---|---|---|---|
| HLA-G-0031 | +++ | − | +++ | − | +++ |
| HLA-G-0039 | +++ | + | +++ | − | +++ |
| HLA-G-0041 | +++ | ++ | +++ | − | +++ |
| HLA-G-0090 | +++ | − | +++ | − | +++ |

The above table summarizes the binding of different rat anti-human HLA-G monoclonal antibodies to HLA-G expressed on different cells and cell lines as assessed by FACS analysis. Either the binding to naturally HLA-G expressing JEG3 tumor cells or Skov3 or PA-TU-8902 transfectants and respective parental, untransfected cells is described.

b) Binding of HLA-G Antibodies to Natural or Recombinant HLA-G Expressed on Cells (as Assessed by FACS Analysis)

For flow cytometry analysis, cells were stained with anti HLA-G mAbs at 4° C. Briefly, 25 µl/well of each cell suspension ($5 \times 10^4$ cells/well) was transferred into a polypropylene 96-Well V-bottom plate and prechilled in the fridge at 5° C. for 10 min. Anti-HLA-G samples were diluted in staining buffer to a 2-fold starting concentration of 80 µg/ml. A 4-fold serial dilution of the antibodies was performed and 25 µl/well of the antibody solution was added to the prepared cells and incubated for 1 h at 5° C. Cells were washed twice with 200 µl/well staining buffer and centrifugation at 300 g for 3 min. For detection fluorescent labeled anti-species antibody (goat anti rat IgG (H+L) conjugated to ALEXA® 488, Life technologies #A11006; or goat anti-mouse IgG (H+L), Life technologies #A11001) or goat anti-human IgG (H+L) conjugated to ALEXA® 488, Life technologies #A11013) was diluted to 20 µg/ml in staining buffer and cell pellets were resuspended in 50 µl/well detection antibody. After a 1-hour incubation at 5° C. cells were again washed twice with staining buffer, resuspended in 70 µl of staining buffer and measured at a FACSC$_{ANTO}$™ 11.

Figure 4D:
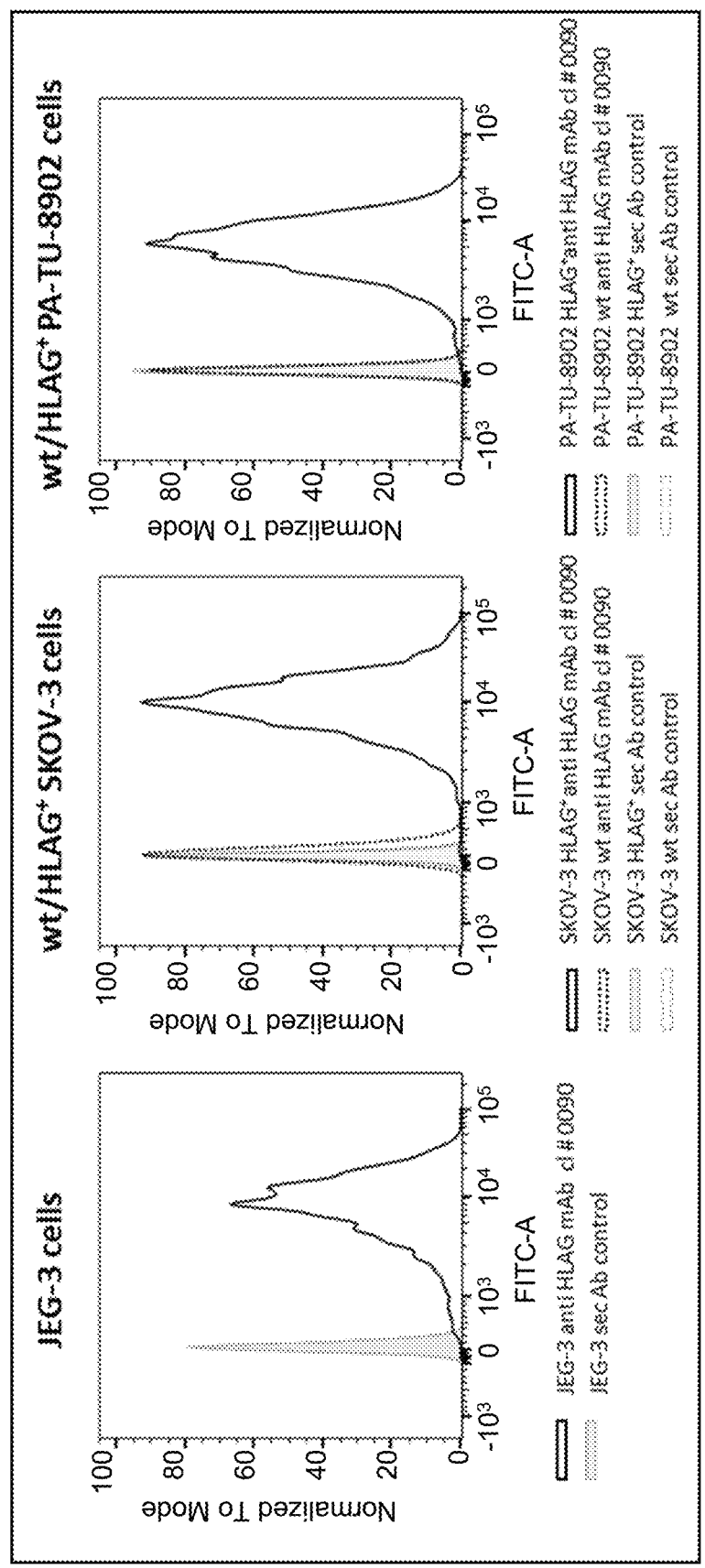

An exemplary FACS staining for anti-HLA-G antibodies HLA-G 0031, HLAG 0039, HLA-G 0041 and HLA-G 0090 is given in the FACS overlays of FIG. 4.

Example 6

Anti HLA-G Antibodies Inhibit/Modulate the Binding of ILT2 to HLA-G Expressed on JEG3 Cells For analysis, JEG3 cells (ATCC HTB36) were stained with ILT2-Fc fusion proteins (control=no inhibition) with or without pre-incubation with different anti-HLA-G antibodies. For the pre-incubation with anti-HLA-G antibodies 25 µl/well of the cell suspension was transferred into a polypropylene 96-Well V-bottom plate and prechilled in the at 4° C. for 10 min. Anti HLA-G antibodies or reference antibodies (G233, MEM-G/9 or 87G) were diluted in staining buffer to a 2-fold concentration of 80 µg/ml and 25 µl/well of the antibody solution was added to the prepared cells and incubated for 1 h at 5° C. Cells were washed twice with 200 µl/well staining buffer with centrifugation at 300 g for 3 min and finally resuspended in 25 µl/well staining buffer.

The detection of human ILT2-Fc Chimera protein (RD #2017-T2-050) to a) JEG3 cells pre-incubated anti HLA-G mAb or b) untreated JEG3 cells as reference was determined as follows: Briefly, the ILT2-Fc or control human IgG (Jackson-Immuno-Research #009-000-003) were diluted in staining buffer to a 2-fold concentration of 20 µg/ml (ILT2) and 25 µl/well of the ILT2-Fc protein solution was added to the prepared cells and incubated for 2 h at 5° C. Cells were again washed twice with 200 µl/well staining buffer the human ILT2-Fc protein was detected with fluorescent labeled anti human IgG Fc-gamma specific antibody (F(ab')$_2$ Fragment Goat Anti-Human IgG, Fcγ fragment specific-FITC, Jackson-Immuno-Research #109-096-008) at a dilution of 10 µg/ml in staining buffer. Cell pellets were resuspended in 50 µl/well detection antibody. After a 1-hour incubation at 5° C. cells were washed twice with staining buffer, resuspended in 70 µl and measured at a FACSC$_{ANTO}$™ II to determine ILT2 binding to JEG 3 cells.

As control, the anti-HLA-G antibodies bound to JEG-3 pre-incubated cells were detected by using anti-species antibody (goat anti-rat IgG (H+L) conjugated to ALEXA® 488, (Life technologies #A11006), or goat-anti mouse IgG (H+L)-ALEXA® 488, (Life technologies, #A11001) at a concentration of 10 µg/ml.

The graph in FIG. 5 shows the respective ability of different HLA-G antibodies to modify the interaction and binding of recombinant ILT2 to HLA-G naturally expressed on JEG3 tumor cells.

The following table summarizes the results from the experiments. The binding of the anti-HLA-G antibodies to JEG3 cells is depicted as +=weak binding-+++=strong binding. The ability of the anti-HLA-G antibodies either to inhibit/block or increase the binding of ILT2 to the HLA-G expressing JEG3 cells. In the last column, the binding of the recombinant ILT2 to the cells or the inhibition/blockade thereof is shown/quantified (staining of ILT2-Fc in the absence of an anti-HLA-G antibody was set to 100% binding which 0% inhibition, a negative value indicates an even increased binding; staining signal differences below 5% were not significant as categorizes with no effect):

from Miltenyi (#130-091-153) according to the manufacturer's instructions (negative selection). The isolated monocytes were resuspended in primary cell culture medium (RPMI 1640, PAN #P04-17500 supplemented with 10% FCS, Gibco #10500; 2 mM L-glutamine, Sigma #G7513; 1 mM Sodium Pyruvate, Gibco #11360; MEM Non-Essential Amino Acids, Gibco #11140; 0.1 mM 2-Mercaptoethanol, Gibco #31350; MEM Vitamins, Gibco #11120; Penicillin Streptomycin, Gibco #15140) at a density of 5×10e5 cells/ml. The enrichment of $CD14^+$ $CD16^+$ cells was monitored by flow cytometry and ILT2 and ILT4 expression of the cells was analyzed. For the co-culture assay of the enriched monocytes with HLA-G-expressing cells, JEG-3 cells ((ATCC HTB36) were seeded one day prior to the assay in a 96-well-flat bottom tissue culture plate with 8×10e3 cells/well in 100 µl in JEG-3 culture medium (MEM Eagle with EBSS and L-glutamine, PAN #P04-00509 supplemented with 10% FCS, Gibco #10500; 1 mM Sodium Pyruvate, Gibco #11360; MEM Non-Essential Amino Acids Gibco #11140) to form a confluent layer on the day of the assay. In some experiments a JEG-3 HLAG knockout cell line was used and seeded as the JEG-3 wt cells as described above. The adherent JEG-3 cells were pre-incubated with a 4fold serial dilution of anti HLA-G antibodies in primary cell culture medium. Therefore the supernatant from the adher-

| Antibody | Binding on JEG-3 cells | HLA-G:ILT2 interaction | Inhibition of ILT2 binding to Jeg3 cells |
|---|---|---|---|
| no mAb (ctrl) | − | − | 0% inhibition = 100% binding |
| HLA-G-0031 | +++ | inhibits binding of ILT2 | 95.1% inhibition |
| HLA-G-0039 | +++ | increased binding of ILT2 | −72.9% (= increase/stimulation of ILT2 binding) |
| HLA-G-0041 | +++ | increased binding of ILT2 | −76.7% (= increase/stimulation of ILT2 binding) |
| HLA-G-0090 | +++ | inhibits binding of ILT2 | 91.8 % inhibition |
| 87G | ++ | no significant effect | 2.3% inhibition |
| MEM-G/9 | +++ | inhibits binding of ILT2 | −27.9% (= increase/stimulation of ILT2 binding) |
| G233 | +++ | inhibits binding of ILT2 | −55.8% (= increase/stimulation of ILT2 binding) |

Example 7

Monocyte Cytokine Restoration Assay (after HLA-G Mediated Suppression)

The following co-culture assay of HLA-G-expressing cells with Monocytes was used for the functional characterization of the different rat anti-human HLA-G monoclonal antibodies. Peripheral human Monocytes were isolated from blood of healthy donors. Briefly, blood was collected in tubes containing an anticoagulant agent and diluted 1:2 in PBS. To isolate peripheral blood mononuclear cells (PBMCs) 30 ml of the mixture was transferred to each LEUCOSEP™ tube with prefilled separation medium. The PBMC specific band was collected after 12 min centrifugation (1200×g without brake), washed three times with PBS and centrifuged for 10 min at 300×g. Finally, cell pellets were resuspended in MACS buffer from Miltenyi and human monocytes were isolated from the PBMCs via magnetic separation with the human Monocyte Isolation Kit II ent JEG-3 cells was removed and 50 µl/Well of the prepared antibody solution was added and incubated at 37° C. and 5% CO2 in a humidified atmosphere for 1 h. Human monocytes were added to the anti HLA-G antibodies pre-incubated JEG-3 cells with 2.5×10e4 human monocytes/Well in 50 µl primary cell culture medium and co-culture was incubated at 37° C. and 5% CO2 in a humidified atmosphere overnight (approx. 18-20 hours). On the next day a LPS stimulation with 50 ng/ml LPS was performed for 7 h and afterwards the supernatant of the co-culture was harvested. The concentration of TNF alpha of the co-culture supernatant was determined using the Human TNF alpha ELISA READY-SET-Go!® from eBioscience (#88-7346-88).

The below tables summarize the functional characteristics of given HLA-G antibodies for a specific donor at different antibody characteristics.

Tables: Functional Anti-HLA-G Antibodies are Able to Restore an HLA-G Specific Suppressed Immune Response, i.e. Restoration of LPS-Induced TNFa Production by Monocytes in Co-Culture with HLA-G-Expressing Cells: Percentage % TNF Release (Restoration) of Functional Anti-HLA-G Antibodies Functional anti-HLA-G antibodies are able to induce (restore a suppressed) immune response, i.e. restoration of LPS-induced TNFa production by monocytes in co-culture with HLA-G-expressing cells (for negative control for an HLAG specific TNF induction an HLAG knock-out cell line was used, to distinguish whether antibodies show either no TNF induction (truly HLA-G specific ones) or show an TNF induction on the knock-out cell lines (which cannot be HLAG specific).

The values of the % TNF induction of anti-HLA-G antibodies are calculated using the following condition: untreated co-culture of JEG3 cells and monocytes=0%, monocyte only culture (without HLA-G induced suppression)=100%.

| Cell line | JEG-3 HLAG knock-out (ko) | JEG-3 wild type (wt) | JEG-3 HLAG ko | JEG-3 wt | JEG-3 HLAG ko | JEG-3 wt | JEG-3 HLAG ko | JEG-3 wt |
|---|---|---|---|---|---|---|---|---|
| Anti-HLA-G antibody | HLAG-0031 | HLAG-0031 | HLAG-0041 | HLAG-0041 | 87G | 87G | G223 | G223 |
| 40 µg/ml | −20% | 275% | 12% | 53% | 86% | 150% | 154% | 144% |
| 10 µg/ml | 6% | 216% | 16% | 41% | 40% | 85% | 50% | 104% |
| 2.5 µg/ml | −40% | 170% | −13% | 63% | 3% | 38% | 29% | 63% |
| 0.63 µg/ml | −23% | 83% | −18% | 34% | −8% | 20% | 5% | 33% |
| 0.16 µg/ml | −29% | 23% | −1% | 43% | −12% | 25% | 0% | 20% |
| untreat | 0% | 0% | 0% | 0% | 0% | 0% | 0% | 0% |
| Monocytes only | 100% | 100% | 100% | 100% | 100% | 100% | 100% | 100% |

From above table it becomes clear that the antibodies of the present invention were able to induce a TNF alpha release in monocytes coculture with HLA-G expressing JEG-3 cells, while they were not able to induce a TNF alpha release in monocytes cocultured with JEG-3 cells with an HLA-G knock-out.

From the table it becomes clear that the reference antibodies are not truly HLA-G specific, as they induce strong TNF alpha release also in HLA-G knock out cell lines.

Dependent on the donor (different donor below) the percentage % TNF release (restoration) varies.

| Cell line Anti-HLA-G antibody | JEG-3 wild type (wt) HLAG-0090 | JEG-3 wild type (wt) HLAG-0031 | wild JEG-3 wild type (wt) HLAG-0041 |
|---|---|---|---|
| 40 µg/ml | 214% | 77% | |
| 10 µg/ml | 221% | 74% | 40% |
| 2.5 µg/ml | 233% | 67% | 59% |
| 0.63 µg/ml | 219% | 44% | 66% |
| 0.16 µg/ml | 198% | 14% | 44% |
| untreat | 0% | 0% | 0% |
| Monocytes only | 100% | 100% | 100% |

The invention claimed is:

1. An isolated antibody that binds to human HLA-G, wherein the antibody comprises
   A) (a) a VH domain comprising (i) HVR-H1 comprising an amino acid sequence of SEQ ID NO:1, (ii) HVR-H2 comprising an amino acid sequence of SEQ ID NO:2, and (iii) HVR-H3 comprising an amino acid sequence SEQ ID NO:3; and (b) a VL domain comprising (i) HVR-L1 comprising an amino acid sequence of SEQ ID NO:4; (ii) HVR-L2 comprising an amino acid sequence of SEQ ID NO:5, and (iii) HVR-L3 comprising an amino acid sequence of SEQ ID NO:6; or
   B) (a) a VH domain comprising (i) HVR-H1 comprising an amino acid sequence of SEQ ID NO:9, (ii) HVR-H2 comprising an amino acid sequence of SEQ ID NO:10, and (iii) HVR-H3 comprising an amino acid sequence SEQ ID NO:11; and (b) a VL domain comprising (i) HVR-L1 comprising an amino acid sequence of SEQ ID NO:12; (ii) HVR-L2 comprising an amino acid sequence of SEQ ID NO:13, and (iii) HVR-L3 comprising an amino acid sequence of SEQ ID NO:14; or
   C) (a) a VH domain comprising (i) HVR-H1 comprising an amino acid sequence of SEQ ID NO:17, (ii) HVR-H2 comprising an amino acid sequence of SEQ ID NO:18, and (iii) HVR-H3 comprising an amino acid sequence SEQ ID NO:19; and (b) a VL domain comprising (i) HVR-L1 comprising an amino acid sequence of SEQ ID NO:20; (ii) HVR-L2 comprising an amino acid sequence of SEQ ID NO:21 and (iii) HVR-L3 comprising an amino acid sequence of SEQ ID NO:22.

2. The antibody according to claim 1, wherein the antibody comprises
   A)
   i) a VH sequence of SEQ ID NO:7 and a VL sequence of SEQ ID NO:8;
   ii) a humanized variant of the VH and VL of the antibody under i); or
   iii) a VH sequence of SEQ ID NO:33 and a VL sequence of SEQ ID NO:34; or
   B)
   a VH sequence of SEQ ID NO:15 and a VL sequence of SEQ ID NO:16; or
   C)
   a VH sequence of SEQ ID NO:23 and a VL sequence of SEQ ID NO:24.

3. The anti-HLA-G antibody according to claim 1, wherein the antibody has at least one of the following properties:
   a) does not cross-react with a modified human HLA-G ß2M MHC I complex comprising SEQ ID NO:44;
   b) does not cross-react with human HLA-A2 ß2M MHC I complex comprising SEQ ID NO:39 and SEQ ID NO: 37;
   c) does not cross-react with a mouse H2Kd ß2M MHC I complex comprising SEQ ID NO:45;
   d) does not cross-react with rat RT1A ß2M MHC I complex comprising SEQ ID NO:47;
   e) inhibits ILT2 binding to monomeric HLA-G ß2M MHC I complex;
   f) inhibits ILT2 binding to trimeric HLA-G ß2M MHC I complex;
   g) inhibits ILT2 binding to monomeric HLA-G ß2M MHC I complex by more than 50%;
   h) inhibits ILT2 binding to dimeric HLA-G ß2M MHC I complex by more than 50%;
   i) inhibits ILT2 binding to trimeric HLA-G ß2M MHC I complex by more than 50%;
   j) inhibits ILT2 binding to JEG3 cells (ATCC No. HTB36);
   k) binds to HLA-G on JEG3 cells (ATCC No. HTB36), and inhibits ILT2 binding to HLA-G on JEG3 cells (ATCC No. HTB36); or
   l) inhibits CD8a binding to HLA-G by more than 80%.

4. The antibody according to claim 1, wherein the antibody is of IgG1 isotype.

5. The antibody according to claim 4, wherein the antibody is of IgG1 isotype with mutations L234A, L235A and P329G (numbering according to the EU index of Kabat).

6. A pharmaceutical formulation comprising the antibody according to claim 1 and a pharmaceutically acceptable carrier.

7. A method for selecting anti-HLA-G antibodies according to claim 1, comprising:
   a) determining the binding of anti-HLA-G antibodies to human HLA-G ß2M MHC I complex comprising SEQ ID NO: 43 by a Surface Plasmon Resonance assay;
   b) determining the inhibition of ILT2 binding to at least one of monomeric, dimeric, or trimeric HLA-G ß2M MHC I complex by the respective anti-HLA-G antibodies;
   c) (i) selecting anti-HLAG antibodies which inhibit ILT2 binding to monomeric HLA-G ß2M MHC I complex by more than 50% or by more than 80% when compared to the binding without antibody, or (ii) selecting anti-HLA-G antibodies which inhibit ILT2 binding to at least one of monomeric, dimeric, or trimeric HLA-G ß2M MHC I complex by more than 50% or by more than 70% when compared to the binding without antibody; and wherein the selecting anti-HLA-G antibodies restore HLA-G specific suppressed immune response by monocytes co-cultured with JEG-3 cells (ATCC HTB36).

8. The method of claim 7, wherein restoring HLA-G specific suppressed immune response by monocytes co-cultures with JEG-3 cells (ATCC HTB36) comprises suppressing tumor necrosis factor (TNF) alpha release from the monocytes.

9. A method for selecting anti-HLA-G antibodies of claim 4, comprising:
   a) determining the binding of anti-HLA-G antibodies to JEG3 cells (ATCC No. HTB36) in a flow cytometry assay;
   b) determining the inhibition of ILT2 binding to JEG3 cells (ATCC No. HTB36) by the respective anti-HLA-G antibodies a flow cytometry assay; and
   c) selecting anti-HLA-G antibodies which bind to JEG3 (ATCC No. HTB36) cells, and which inhibit ILT2 binding to JEG3 cells (ATCC No. HTB36) by more than 50% or by more than 80% when compared to the binding without antibody.

10. The method of claim 9, wherein the flow cytometry assay is fluorescence-activated cell sorting (FACS) assay.

11. A method of treating cancer in a subject, comprising administering to the subject an effective amount of the antibody of claim 1.

* * * * *

SEQUENCE LISTING

<160> NUMBER OF SEQ ID NOS: 55

<210> SEQ ID NO 1
<211> LENGTH: 5
<212> TYPE: PRT
<213> ORGANISM: rat

<400> SEQUENCE: 1

Asp Tyr Trp Val Ser
1               5

<210> SEQ ID NO 2
<211> LENGTH: 15
<212> TYPE: PRT

```
<213> ORGANISM: rat

<400> SEQUENCE: 2

Glu Ile Ser Pro Asn Ser Gly Ala Ser Asn Phe Asp Glu Asn Phe
1               5                   10                  15

<210> SEQ ID NO 3
<211> LENGTH: 11
<212> TYPE: PRT
<213> ORGANISM: rat

<400> SEQUENCE: 3

Ser Ser His Gly Ser Phe Arg Trp Phe Ala Tyr
1               5                   10

<210> SEQ ID NO 4
<211> LENGTH: 12
<212> TYPE: PRT
<213> ORGANISM: rat

<400> SEQUENCE: 4

Arg Ala Ser Ser Ser Val Ser Ser Asn His Leu His
1               5                   10

<210> SEQ ID NO 5
<211> LENGTH: 7
<212> TYPE: PRT
<213> ORGANISM: rat

<400> SEQUENCE: 5

Ser Thr Ser Gln Arg Ala Ser
1               5

<210> SEQ ID NO 6
<211> LENGTH: 9
<212> TYPE: PRT
<213> ORGANISM: rat

<400> SEQUENCE: 6

Gln Gln Gly Ser Ser Asn Pro Tyr Thr
1               5

<210> SEQ ID NO 7
<211> LENGTH: 120
<212> TYPE: PRT
<213> ORGANISM: rat

<400> SEQUENCE: 7

Gln Val Lys Leu Met Gln Ser Gly Ala Ala Leu Val Lys Pro Gly Thr
1               5                   10                  15

Ser Val Lys Met Ser Cys Asn Ala Ser Gly Tyr Thr Phe Thr Asp Tyr
            20                  25                  30

Trp Val Ser Trp Val Lys Gln Ser His Gly Lys Arg Leu Glu Trp Val
        35                  40                  45

Gly Glu Ile Ser Pro Asn Ser Gly Ala Ser Asn Phe Asp Glu Asn Phe
    50                  55                  60

Lys Asp Lys Ala Thr Leu Thr Val Asp Lys Ser Thr Thr Ala Tyr
65                  70                  75                  80

Met Glu Leu Ser Arg Leu Thr Ser Glu Asp Ser Ala Ile Tyr Tyr Cys
                85                  90                  95

Thr Arg Ser Ser His Gly Ser Phe Arg Trp Phe Ala Tyr Trp Gly Gln
            100                 105                 110
```

```
Gly Thr Leu Val Thr Val Ser Ser
        115                 120
```

<210> SEQ ID NO 8
<211> LENGTH: 108
<212> TYPE: PRT
<213> ORGANISM: rat

<400> SEQUENCE: 8

```
Ala Ile Val Leu Asn Gln Ser Pro Ser Ser Ile Val Ala Ser Gln Gly
1               5                   10                  15

Glu Lys Val Thr Ile Thr Cys Arg Ala Ser Ser Val Ser Ser Asn
            20                  25                  30

His Leu His Trp Tyr Gln Gln Lys Pro Gly Ala Phe Pro Lys Phe Val
        35                  40                  45

Ile Tyr Ser Thr Ser Gln Arg Ala Ser Gly Ile Pro Ser Arg Phe Ser
    50                  55                  60

Gly Ser Gly Ser Gly Thr Ser Tyr Ser Phe Thr Ile Ser Arg Val Glu
65                  70                  75                  80

Ala Glu Asp Val Ala Thr Tyr Tyr Cys Gln Gln Gly Ser Ser Asn Pro
                85                  90                  95

Tyr Thr Phe Gly Ala Gly Thr Lys Leu Glu Leu Lys
            100                 105
```

<210> SEQ ID NO 9
<211> LENGTH: 5
<212> TYPE: PRT
<213> ORGANISM: human

<400> SEQUENCE: 9

```
Ser Tyr Ala Met Asn
1               5
```

<210> SEQ ID NO 10
<211> LENGTH: 17
<212> TYPE: PRT
<213> ORGANISM: human

<400> SEQUENCE: 10

```
Val Ile Ser Gly Ser Gly Val Ser Thr Tyr Tyr Ala Asp Ser Val Lys
1               5                   10                  15

Gly
```

<210> SEQ ID NO 11
<211> LENGTH: 14
<212> TYPE: PRT
<213> ORGANISM: human

<400> SEQUENCE: 11

```
Asp Gly Ser Tyr Asn Tyr Gly Tyr Gly Asp Tyr Phe Asp Tyr
1               5                   10
```

<210> SEQ ID NO 12
<211> LENGTH: 17
<212> TYPE: PRT
<213> ORGANISM: human

<400> SEQUENCE: 12

```
Lys Ser Ser Gln Ser Val Leu Tyr Ser Ser Lys Asn Lys Asn Tyr Leu
1               5                   10                  15
```

Ala

<210> SEQ ID NO 13
<211> LENGTH: 7
<212> TYPE: PRT
<213> ORGANISM: human

<400> SEQUENCE: 13

Trp Ala Ser Thr Arg Glu Ser
1               5

<210> SEQ ID NO 14
<211> LENGTH: 9
<212> TYPE: PRT
<213> ORGANISM: human

<400> SEQUENCE: 14

Gln Gln Tyr Tyr Asn Thr Pro Arg Thr
1               5

<210> SEQ ID NO 15
<211> LENGTH: 123
<212> TYPE: PRT
<213> ORGANISM: human

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Val Ile Ser Gly Ser Gly Val Ser Thr Tyr Tyr Ala Asp Ser Val
    50                  55                  60

Lys Gly Arg Phe Thr Ile Ser Arg Asp Asn Ser Arg Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Gly Ser Tyr Asn Tyr Gly Tyr Gly Asp Tyr Phe Asp Tyr
            100                 105                 110

Trp Gly Gln Gly Thr Leu Val Thr Val Ser Ser
        115                 120

<210> SEQ ID NO 16
<211> LENGTH: 113
<212> TYPE: PRT
<213> ORGANISM: human

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Lys Asn Lys Asn Tyr Leu Ala Trp Tyr Gln Gln Lys Pro Gly Gln
        35                  40                  45

Pro Pro Lys Leu Phe Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Asn Thr Pro Arg Thr Phe Gly Gln Gly Thr Lys Val Glu Ile
            100                 105                 110

Lys

<210> SEQ ID NO 17
<211> LENGTH: 5
<212> TYPE: PRT
<213> ORGANISM: human

<400> SEQUENCE: 17

Thr Tyr Gly Met Ser
1               5

<210> SEQ ID NO 18
<211> LENGTH: 17
<212> TYPE: PRT
<213> ORGANISM: human

<400> SEQUENCE: 18

Val Ile Ser Gly Gly Gly Val Ser Thr Tyr Tyr Ala Asp Ser Val Lys
1               5                   10                  15

Gly

<210> SEQ ID NO 19
<211> LENGTH: 14
<212> TYPE: PRT
<213> ORGANISM: human

<400> SEQUENCE: 19

Asp Gly Ser Tyr Asn Tyr Gly Tyr Gly Asp Tyr Phe Asp Tyr
1               5                   10

<210> SEQ ID NO 20
<211> LENGTH: 17
<212> TYPE: PRT
<213> ORGANISM: human

<400> SEQUENCE: 20

Lys Ser Ser Gln Asn Val Leu Tyr Ser Ser Asn Asn Lys Asn Tyr Leu
1               5                   10                  15

Ala

<210> SEQ ID NO 21
<211> LENGTH: 7
<212> TYPE: PRT
<213> ORGANISM: human

<400> SEQUENCE: 21

Trp Ala Ser Thr Arg Glu Ser
1               5

<210> SEQ ID NO 22
<211> LENGTH: 9
<212> TYPE: PRT
<213> ORGANISM: human

<400> SEQUENCE: 22

Gln Gln Tyr Tyr Asn Thr Pro Arg Thr
1               5

```
<210> SEQ ID NO 23
<211> LENGTH: 123
<212> TYPE: PRT
<213> ORGANISM: human

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met Ser Trp Val Arg Gln Ala Pro Gly Lys Gly Leu Glu Trp Val
        35                  40                  45

Ser Val Ile Ser Gly Gly Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Lys Asp Gly Ser Tyr Asn Tyr Gly Tyr Gly Asp Tyr Phe Asp Tyr
            100                 105                 110

Trp Gly Gln Gly Thr Leu Val Thr Val Ser Ser
        115                 120

<210> SEQ ID NO 24
<211> LENGTH: 113
<212> TYPE: PRT
<213> ORGANISM: human

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Val Leu Tyr Ser
            20                  25                  30

Ser Asn Asn Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Thr Pro Arg Thr Phe Gly Gln Gly Thr Lys Val Glu Ile
            100                 105                 110

Lys

<210> SEQ ID NO 25
<211> LENGTH: 7
<212> TYPE: PRT
<213> ORGANISM: human

<400> SEQUENCE: 25

Ser Asn Arg Ala Ala Trp Asn
1               5

<210> SEQ ID NO 26
<211> LENGTH: 18
<212> TYPE: PRT
<213> ORGANISM: human
```

```
<400> SEQUENCE: 26

Arg Thr Tyr Tyr Arg Ser Lys Trp Tyr Asn Asp Tyr Ala Val Ser Val
1               5                   10                  15

Gln Gly

<210> SEQ ID NO 27
<211> LENGTH: 9
<212> TYPE: PRT
<213> ORGANISM: human

<400> SEQUENCE: 27

Val Arg Ala Val Ala Pro Phe Asp Tyr
1               5

<210> SEQ ID NO 28
<211> LENGTH: 17
<212> TYPE: PRT
<213> ORGANISM: human

<400> SEQUENCE: 28

Lys Ser Ser Gln Ser Val Leu Asn Ser Ser Asn Asn Lys Asn Asn Leu
1               5                   10                  15

Ala

<210> SEQ ID NO 29
<211> LENGTH: 7
<212> TYPE: PRT
<213> ORGANISM: human

<400> SEQUENCE: 29

Trp Ala Ser Thr Arg Glu Ser
1               5

<210> SEQ ID NO 30
<211> LENGTH: 9
<212> TYPE: PRT
<213> ORGANISM: human

<400> SEQUENCE: 30

Gln Gln Tyr Tyr Arg Thr Pro Trp Thr
1               5

<210> SEQ ID NO 31
<211> LENGTH: 121
<212> TYPE: PRT
<213> ORGANISM: human

<400> SEQUENCE: 31

Gln Val Gln Leu Gln Gln Ser Gly Pro Gly Leu Leu Lys Pro Ser Gln
1               5                   10                  15

Thr Leu Ser Leu Thr Cys Ala Ile Ser Gly Asp Ser Val Ser Ser Asn
            20                  25                  30

Arg Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Gln Gly Arg Ile Thr Leu Ile Pro Asp Thr Ser Lys Asn
65                  70                  75                  80

Gln Phe Ser Leu Arg Leu Asn Ser Val Thr Pro Glu Asp Thr Ala Val
                85                  90                  95
```

Tyr Tyr Cys Ala Ser Val Arg Ala Val Ala Pro Phe Asp Tyr Trp Gly
            100                 105                 110

Gln Gly Val Leu Val Thr Val Ser Ser
        115                 120

<210> SEQ ID NO 32
<211> LENGTH: 113
<212> TYPE: PRT
<213> ORGANISM: human

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asn Ser
            20                  25                  30

Ser Asn Asn Lys Asn Asn Leu Ala Trp Tyr Gln Gln Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Arg Thr Pro Trp Thr Phe Gly Gln Gly Thr Lys Val Glu Ile
            100                 105                 110

Lys

<210> SEQ ID NO 33
<211> LENGTH: 120
<212> TYPE: PRT
<213> ORGANISM: artificial
<220> FEATURE:
<223> OTHER INFORMATION: humanized variant heavy chain variable domain
      VH, HLA-G-0031-0104 (HLA-G-0104)

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Trp Val Ser Trp Val Arg Gln Ala Pro Gly Gln Arg Leu Glu Trp Met
        35                  40                  45

Gly Glu Ile Ser Pro Asn Ser Gly Ala Ser Asn Phe Asp Glu Asn Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Ser His Gly Ser Phe Arg Trp Phe Ala Tyr Trp Gly Gln
            100                 105                 110

Gly Thr Leu Val Thr Val Ser Ser
        115                 120

<210> SEQ ID NO 34
<211> LENGTH: 108
<212> TYPE: PRT
<213> ORGANISM: artificial
<220> FEATURE:
<223> OTHER INFORMATION: humanized variant light chain variable domain

VL, HLA-G-0031-0104 (HLA-G-0104)

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Ser Asn
            20                  25                  30

His Leu His Trp Tyr Gln Gln Lys Pro Gly Lys Ala Pro Lys Phe Leu
        35                  40                  45

Ile Tyr Ser Thr Ser Gln Arg Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Gln Gln Gly Ser Ser Asn Pro
                85                  90                  95

Tyr Thr Phe Gly Gln Gly Thr Lys Leu Glu Ile Lys
            100                 105

<210> SEQ ID NO 35
<211> LENGTH: 314
<212> TYPE: PRT
<213> ORGANISM: homo sapiens

<400> SEQUENCE: 35

Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
    50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala Ser Ser His Thr Leu Gln
                85                  90                  95

Trp Met Ile Gly Cys Asp Leu Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
    130                 135                 140

Arg Lys Cys Glu Ala Ala Asn Val Ala Glu Gln Arg Arg Ala Tyr Leu
145                 150                 155                 160

Glu Gly Thr Cys Val Glu Trp Leu His Arg Tyr Leu Glu Asn Gly Lys
                165                 170                 175

Glu Met Leu Gln Arg Ala Asp Pro Pro Lys Thr His Val Thr His His
            180                 185                 190

Pro Val Phe Asp Tyr Glu Ala Thr Leu Arg Cys Trp Ala Leu Gly Phe
        195                 200                 205

Tyr Pro Ala Glu Ile Ile Leu Thr Trp Gln Arg Asp Gly Glu Asp Gln
    210                 215                 220

Thr Gln Asp Val Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg

-continued

```
                    245                 250                 255
Tyr Thr Cys His Val Gln His Glu Gly Leu Pro Glu Pro Leu Met Leu
            260                 265                 270

Arg Trp Lys Gln Ser Ser Leu Pro Thr Ile Pro Ile Met Gly Ile Val
        275                 280                 285

Ala Gly Leu Val Val Leu Ala Val Val Thr Gly Ala Ala Val Ala
    290                 295                 300

Ala Val Leu Trp Arg Lys Lys Ser Ser Asp
305                 310

<210> SEQ ID NO 36
<211> LENGTH: 274
<212> TYPE: PRT
<213> ORGANISM: homo sapiens

<400> SEQUENCE: 36

Gly Ser His Ser Met Arg Tyr Phe Ser Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ser Ala Cys Pro Arg Met Glu Pro Arg
        35                  40                  45

Ala Pro Trp Val Glu Gln Glu Gly Pro Glu Tyr Trp Glu Glu Glu Thr
    50                  55                  60

Arg Asn Thr Lys Ala His Ala Gln Thr Asp Arg Met Asn Leu Gln Thr
65                  70                  75                  80

Leu Arg Gly Tyr Tyr Asn Gln Ser Glu Ala Ser Ser His Thr Leu Gln
                85                  90                  95

Trp Met Ile Gly Cys Asp Leu Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
    130                 135                 140

Arg Lys Cys Glu Ala Ala Asn Val Ala Glu Gln Arg Arg Ala Tyr Leu
145                 150                 155                 160

Glu Gly Thr Cys Val Glu Trp Leu His Arg Tyr Leu Glu Asn Gly Lys
                165                 170                 175

Glu Met Leu Gln Arg Ala Asp Pro Pro Lys Thr His Val Thr His His
            180                 185                 190

Pro Val Phe Asp Tyr Glu Ala Thr Leu Arg Cys Trp Ala Leu Gly Phe
        195                 200                 205

Tyr Pro Ala Glu Ile Ile Leu Thr Trp Gln Arg Asp Gly Glu Asp Gln
    210                 215                 220

Thr Gln Asp Val Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Glu Pro Leu Met Leu
            260                 265                 270

Arg Trp

<210> SEQ ID NO 37
<211> LENGTH: 99
<212> TYPE: PRT
```

<213> ORGANISM: homo sapiens

<400> SEQUENCE: 37

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 38
<211> LENGTH: 275
<212> TYPE: PRT
<213> ORGANISM: Artificial
<220> FEATURE:
<223> OTHER INFORMATION: modified human HLA-G (wherein the HLA-G
      specific amino acids have been replaced by HLA-A consensus amino
      acids (= degrafted HLA-G) ECD

<400> SEQUENCE: 38

Gly Ser His Ser Met Arg Tyr Phe Ser Ala Ala Val Ser Arg Pro Gly
1               5                   10                  15

Arg Gly Glu Pro Arg Phe Ile Ala Met Gly Tyr Val Asp Asp Thr Gln
            20                  25                  30

Phe Val Arg Phe Asp Ser Asp Ala Ala Ser Pro Arg Met Glu Pro Arg
        35                  40                  45

Ala Pro Trp Val Glu Gln Glu Gly Pro Glu Tyr Trp Asp Glu Glu Thr
    50                  55                  60

Arg Asn Thr Lys Ala His Ala Gln Thr Asp Arg Val Asn Leu Gly Thr
65                  70                  75                  80

Leu Arg Gly Cys Tyr Asn Gln Ser Glu Ala Gly Ser His Thr Leu Gln
                85                  90                  95

Trp Met Ile Gly Cys Asp Val Gly Ser Asp Gly Arg Leu Leu Arg Gly
            100                 105                 110

Tyr Glu Gln Tyr Ala Tyr Asp Gly Lys Asp Tyr Leu Ala Leu Asn Glu
        115                 120                 125

Asp Leu Arg Ser Trp Thr Ala Ala Asp Thr Ala Ala Gln Ile Ser Lys
    130                 135                 140

Arg Lys Cys Glu Ala Ala His Val Ala Glu Gln Arg Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Val Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Val Glu Leu Val Glu Thr Arg Pro Ala Gly Asp Gly Thr

```
225                 230                 235                 240

Phe Gln Lys Trp Ala Ala Val Val Pro Ser Gly Glu Gln Arg
                245                 250                 255

Tyr Thr Cys His Val Gln His Glu Gly Leu Pro Glu Pro Leu Thr Leu
                260                 265                 270

Arg Trp Lys
        275

<210> SEQ ID NO 39
<211> LENGTH: 341
<212> TYPE: PRT
<213> ORGANISM: homo sapiens

<400> SEQUENCE: 39

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
        50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
                100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Thr Thr Lys
        130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
                260                 265                 270

Arg Trp Glu Pro Ser Ser Gln Pro Thr Ile Pro Ile Val Gly Ile Ile
            275                 280                 285

Ala Gly Leu Val Leu Phe Gly Ala Val Ile Thr Gly Ala Val Val Ala
        290                 295                 300

Ala Val Met Trp Arg Arg Lys Ser Ser Asp Arg Lys Gly Gly Ser Tyr
305                 310                 315                 320
```

Ser Gln Ala Ala Ser Ser Asp Ser Ala Gln Gly Ser Asp Val Ser Leu
                325                 330                 335

Thr Ala Cys Lys Val
            340

<210> SEQ ID NO 40
<211> LENGTH: 275
<212> TYPE: PRT
<213> ORGANISM: homo sapiens

<400> SEQUENCE: 40

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu
        275

<210> SEQ ID NO 41
<211> LENGTH: 275
<212> TYPE: PRT
<213> ORGANISM: mus musculus

<400> SEQUENCE: 41

Gly Pro His Ser Leu Arg Tyr Phe Val Thr Ala Val Ser Arg Pro Gly
1               5                   10                  15

-continued

```
Leu Gly Glu Pro Arg Phe Ile Ala Val Gly Tyr Val Asp Thr Gln
            20                  25                  30

Phe Val Arg Phe Asp Ser Asp Ala Asp Asn Pro Arg Phe Glu Pro Arg
        35                  40                  45

Ala Pro Trp Met Glu Gln Glu Gly Pro Glu Tyr Trp Glu Gln Thr
50                  55                  60

Gln Arg Ala Lys Ser Asp Glu Gln Trp Phe Arg Val Ser Leu Arg Thr
65                  70                  75                  80

Ala Gln Arg Cys Tyr Asn Gln Ser Lys Gly Gly Ser His Thr Phe Gln
                85                  90                  95

Arg Met Phe Gly Cys Asp Val Gly Ser Asp Trp Arg Leu Leu Arg Gly
                100                 105                 110

Tyr Gln Gln Phe Ala Tyr Asp Gly Arg Asp Tyr Ile Ala Leu Asn Glu
            115                 120                 125

Asp Leu Lys Thr Trp Thr Ala Ala Asp Thr Ala Ala Leu Ile Thr Arg
    130                 135                 140

Arg Lys Trp Glu Gln Ala Gly Asp Ala Glu Tyr Tyr Arg Ala Tyr Leu
145                 150                 155                 160

Glu Gly Glu Cys Val Glu Trp Leu Arg Arg Tyr Leu Glu Leu Gly Asn
                165                 170                 175

Glu Thr Leu Leu Arg Thr Asp Ser Pro Lys Ala His Val Thr Tyr His
            180                 185                 190

Pro Arg Ser Gln Val Asp Val Thr Leu Arg Cys Trp Ala Leu Gly Phe
        195                 200                 205

Tyr Pro Ala Asp Ile Thr Leu Thr Trp Gln Leu Asn Gly Glu Asp Leu
    210                 215                 220

Thr Gln Asp Met Glu Leu Val Glu Thr Arg Pro Ala Gly Asp Gly Thr
225                 230                 235                 240

Phe Gln Lys Trp Ala Ala Val Val Pro Leu Gly Lys Glu Gln Asn
                245                 250                 255

Tyr Thr Cys His Val His His Lys Gly Leu Pro Glu Pro Leu Thr Leu
            260                 265                 270

Arg Trp Lys
        275

<210> SEQ ID NO 42
<211> LENGTH: 274
<212> TYPE: PRT
<213> ORGANISM: rat

<400> SEQUENCE: 42

Gly Ser His Ser Leu Arg Tyr Phe Tyr Thr Ala Val Ser Arg Pro Gly
1               5                   10                  15

Leu Gly Glu Pro Arg Phe Ile Ala Val Gly Tyr Val Asp Asp Thr Glu
            20                  25                  30

Phe Val Arg Phe Asp Ser Asp Ala Glu Asn Pro Arg Met Glu Pro Arg
        35                  40                  45

Ala Arg Trp Met Glu Arg Glu Gly Pro Glu Tyr Trp Glu Gln Gln Thr
    50                  55                  60

Arg Ile Ala Lys Glu Trp Glu Gln Ile Tyr Arg Val Asp Leu Arg Thr
65                  70                  75                  80

Leu Arg Gly Cys Tyr Asn Gln Ser Glu Gly Gly Ser His Thr Ile Gln
                85                  90                  95

Glu Met Tyr Gly Cys Asp Val Gly Ser Asp Gly Ser Leu Leu Arg Gly
            100                 105                 110
```

```
Tyr Arg Gln Asp Ala Tyr Asp Gly Arg Asp Tyr Ile Ala Leu Asn Glu
            115                 120                 125

Asp Leu Lys Thr Trp Thr Ala Ala Asp Phe Ala Ala Gln Ile Thr Arg
    130                 135                 140

Asn Lys Trp Glu Arg Ala Arg Tyr Ala Glu Arg Leu Arg Ala Tyr Leu
145                 150                 155                 160

Glu Gly Thr Cys Val Glu Trp Leu Ser Arg Tyr Leu Glu Leu Gly Lys
                165                 170                 175

Glu Thr Leu Leu Arg Ser Asp Pro Pro Glu Ala His Val Thr Leu His
            180                 185                 190

Pro Arg Pro Glu Gly Asp Val Thr Leu Arg Cys Trp Ala Leu Gly Phe
        195                 200                 205

Tyr Pro Ala Asp Ile Thr Leu Thr Trp Gln Leu Asn Gly Glu Asp Leu
    210                 215                 220

Thr Gln Asp Met Glu Leu Val Glu Thr Arg Pro Ala Gly Asp Gly Thr
225                 230                 235                 240

Phe Gln Lys Trp Ala Ser Val Val Val Pro Leu Gly Lys Glu Gln Asn
                245                 250                 255

Tyr Thr Cys Arg Val Glu His Glu Gly Leu Pro Lys Pro Leu Ser Gln
            260                 265                 270

Arg Trp

<210> SEQ ID NO 43
<211> LENGTH: 440
<212> TYPE: PRT
<213> ORGANISM: homo sapiens

<400> SEQUENCE: 43

Arg Ile Ile Pro Arg His Leu Gln Leu Gly Cys Gly Gly Ser Gly Gly
1               5                   10                  15

Gly Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
        115                 120                 125

Gly Gly Gly Gly Ser Gly Gly Gly Gly Ser Gly Gly Gly Gly Ser Gly
    130                 135                 140

Ser His Ser Met Arg Tyr Phe Ser Ala Ala Val Ser Arg Pro Gly Arg
145                 150                 155                 160

Gly Glu Pro Arg Phe Ile Ala Met Gly Tyr Val Asp Asp Thr Gln Phe
                165                 170                 175

Val Arg Phe Asp Ser Asp Ser Ala Cys Pro Arg Met Glu Pro Arg Ala
            180                 185                 190

Pro Trp Val Glu Gln Glu Gly Pro Glu Tyr Trp Glu Glu Glu Thr Arg
        195                 200                 205
```

Asn Thr Lys Ala His Ala Gln Thr Asp Arg Met Asn Leu Gln Thr Leu
            210                 215                 220

Arg Gly Cys Tyr Asn Gln Ser Glu Ala Ser Ser His Thr Leu Gln Trp
225                 230                 235                 240

Met Ile Gly Cys Asp Leu Gly Ser Asp Gly Arg Leu Leu Arg Gly Tyr
                245                 250                 255

Glu Gln Tyr Ala Tyr Asp Gly Lys Asp Tyr Leu Ala Leu Asn Glu Asp
            260                 265                 270

Leu Arg Ser Trp Thr Ala Ala Asp Thr Ala Ala Gln Ile Ser Lys Arg
        275                 280                 285

Lys Cys Glu Ala Ala Asn Val Ala Glu Gln Arg Arg Ala Tyr Leu Glu
    290                 295                 300

Gly Thr Cys Val Glu Trp Leu His Arg Tyr Leu Glu Asn Gly Lys Glu
305                 310                 315                 320

Met Leu Gln Arg Ala Asp Pro Pro Lys Thr His Val Thr His His Pro
                325                 330                 335

Val Phe Asp Tyr Glu Ala Thr Leu Arg Cys Trp Ala Leu Gly Phe Tyr
            340                 345                 350

Pro Ala Glu Ile Ile Leu Thr Trp Gln Arg Asp Gly Glu Asp Gln Thr
        355                 360                 365

Gln Asp Val Glu Leu Val Glu Thr Arg Pro Ala Gly Asp Gly Thr Phe
    370                 375                 380

Gln Lys Trp Ala Ala Val Val Val Pro Ser Gly Glu Glu Gln Arg Tyr
385                 390                 395                 400

Thr Cys His Val Gln His Glu Gly Leu Pro Glu Pro Leu Met Leu Arg
                405                 410                 415

Trp Gly Ser Gly Leu Asn Asp Ile Phe Glu Ala Gln Lys Ile Glu Trp
            420                 425                 430

His Glu His His His His His His
        435                 440

<210> SEQ ID NO 44
<211> LENGTH: 441
<212> TYPE: PRT
<213> ORGANISM: Artificial
<220> FEATURE:
<223> OTHER INFORMATION: exemplary modified human HLA-G beta2M MHC class
      I complex (wherein the HLA-G specific amino acids have been
      replaced by HLA-A consensus amino acids  (= degrafted HLA-G)

<400> SEQUENCE: 44

Arg Ile Ile Pro Arg His Leu Gln Leu Gly Cys Gly Gly Ser Gly Gly
1               5                   10                  15

Gly Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Ser
            115                 120                 125

Gly Gly Gly Gly Ser Gly Gly Gly Ser Gly Gly Gly Ser Gly
130                 135                 140

Ser His Ser Met Arg Tyr Phe Ser Ala Ala Val Ser Arg Pro Gly Arg
145                 150                 155                 160

Gly Glu Pro Arg Phe Ile Ala Met Gly Tyr Val Asp Asp Thr Gln Phe
                165                 170                 175

Val Arg Phe Asp Ser Asp Ala Ala Ser Pro Arg Met Glu Pro Arg Ala
            180                 185                 190

Pro Trp Val Glu Gln Glu Gly Pro Glu Tyr Trp Asp Glu Thr Arg
        195                 200                 205

Asn Thr Lys Ala His Ala Gln Thr Asp Arg Val Asn Leu Gly Thr Leu
    210                 215                 220

Arg Gly Cys Tyr Asn Gln Ser Glu Ala Gly Ser His Thr Leu Gln Trp
225                 230                 235                 240

Met Ile Gly Cys Asp Val Gly Ser Asp Gly Arg Leu Leu Arg Gly Tyr
                245                 250                 255

Glu Gln Tyr Ala Tyr Asp Gly Lys Asp Tyr Leu Ala Leu Asn Glu Asp
            260                 265                 270

Leu Arg Ser Trp Thr Ala Ala Asp Thr Ala Ala Gln Ile Ser Lys Arg
        275                 280                 285

Lys Cys Glu Ala Ala His Val Ala Glu Gln Arg Arg Ala Tyr Leu Glu
    290                 295                 300

Gly Thr Cys Val Glu Trp Leu Arg Arg Tyr Leu Glu Asn Gly Lys Glu
305                 310                 315                 320

Thr Leu Gln Arg Ala Asp Pro Pro Lys Thr His Val Thr His His Pro
                325                 330                 335

Val Ser Asp His Glu Ala Thr Leu Arg Cys Trp Ala Leu Gly Phe Tyr
            340                 345                 350

Pro Ala Glu Ile Thr Leu Thr Trp Gln Arg Asp Gly Glu Asp Gln Thr
        355                 360                 365

Gln Asp Val Glu Leu Val Glu Thr Arg Pro Ala Gly Asp Gly Thr Phe
    370                 375                 380

Gln Lys Trp Ala Ala Val Val Val Pro Ser Gly Glu Glu Gln Arg Tyr
385                 390                 395                 400

Thr Cys His Val Gln His Glu Gly Leu Pro Glu Pro Leu Thr Leu Arg
                405                 410                 415

Trp Lys Gly Gly Gly Leu Asn Asp Ile Phe Glu Ala Gln Lys Ile Glu
            420                 425                 430

Trp His Glu His His His His His
        435                 440

<210> SEQ ID NO 45
<211> LENGTH: 441
<212> TYPE: PRT
<213> ORGANISM: mus musculus

<400> SEQUENCE: 45

Thr Tyr Gln Arg Thr Arg Ala Leu Val Gly Cys Gly Gly Ser Gly Gly
1               5                   10                  15

Gly Gly Ser Gly Gly Gly Gly Ser Ile Gln Lys Thr Pro Gln Ile Gln
                20                  25                  30

Val Tyr Ser Arg His Pro Pro Glu Asn Gly Lys Pro Asn Ile Leu Asn
            35                  40                  45

Cys Tyr Val Thr Gln Phe His Pro His Ile Glu Ile Gln Met Leu
        50                  55                  60

Lys Asn Gly Lys Lys Ile Pro Lys Val Glu Met Ser Asp Met Ser Phe
 65                  70                  75                  80

Ser Lys Asp Trp Ser Phe Tyr Ile Leu Ala His Thr Glu Phe Thr Pro
                 85                  90                  95

Thr Glu Thr Asp Thr Tyr Ala Cys Arg Val Lys His Asp Ser Met Ala
            100                 105                 110

Glu Pro Lys Thr Val Tyr Trp Asp Arg Asp Met Gly Gly Gly Gly Ser
            115                 120                 125

Gly Gly Gly Gly Ser Gly Gly Gly Ser Gly Gly Gly Gly Ser Gly
130                 135                 140

Pro His Ser Leu Arg Tyr Phe Val Thr Ala Val Ser Arg Pro Gly Leu
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Asp Asn Pro Arg Phe Glu Pro Arg Ala
            180                 185                 190

Pro Trp Met Glu Gln Glu Gly Pro Glu Tyr Trp Glu Glu Gln Thr Gln
            195                 200                 205

Arg Ala Lys Ser Asp Glu Gln Trp Phe Arg Val Ser Leu Arg Thr Ala
210                 215                 220

Gln Arg Cys Tyr Asn Gln Ser Lys Gly Gly Ser His Thr Phe Gln Arg
225                 230                 235                 240

Met Phe Gly Cys Asp Val Gly Ser Asp Trp Arg Leu Leu Arg Gly Tyr
                245                 250                 255

Gln Gln Phe Ala Tyr Asp Gly Arg Asp Tyr Ile Ala Leu Asn Glu Asp
            260                 265                 270

Leu Lys Thr Trp Thr Ala Ala Asp Thr Ala Ala Leu Ile Thr Arg Arg
            275                 280                 285

Lys Trp Glu Gln Ala Gly Asp Ala Glu Tyr Tyr Arg Ala Tyr Leu Glu
290                 295                 300

Gly Glu Cys Val Glu Trp Leu Arg Arg Tyr Leu Glu Leu Gly Asn Glu
305                 310                 315                 320

Thr Leu Leu Arg Thr Asp Ser Pro Lys Ala His Val Thr Tyr His Pro
                325                 330                 335

Arg Ser Gln Val Asp Val Thr Leu Arg Cys Trp Ala Leu Gly Phe Tyr
            340                 345                 350

Pro Ala Asp Ile Thr Leu Thr Trp Gln Leu Asn Gly Glu Asp Leu Thr
            355                 360                 365

Gln Asp Met Glu Leu Val Glu Thr Arg Pro Ala Gly Asp Gly Thr Phe
370                 375                 380

Gln Lys Trp Ala Ala Val Val Val Pro Leu Gly Lys Glu Gln Asn Tyr
385                 390                 395                 400

Thr Cys His Val His His Lys Gly Leu Pro Glu Pro Leu Thr Leu Arg
                405                 410                 415

Trp Lys Gly Gly Gly Leu Asn Asp Ile Phe Glu Ala Gln Lys Ile Glu
            420                 425                 430

Trp His Glu His His His His His His
            435                 440

<210> SEQ ID NO 46
<211> LENGTH: 441

<212> TYPE: PRT
<213> ORGANISM: Artificial
<220> FEATURE:
<223> OTHER INFORMATION: exemplary human HLA-G/ mouse H2Kd beta2M MHC
      class I complex wherein the positions specific for human HLA-G are
      grafted onto the mouse H2Kd framework

<400> SEQUENCE: 46

Thr Tyr Gln Arg Thr Arg Ala Leu Val Gly Cys Gly Ser Gly Gly
1               5                   10                  15

Gly Gly Ser Gly Gly Gly Ser Ile Gln Lys Thr Pro Gln Ile Gln
            20                  25                  30

Val Tyr Ser Arg His Pro Pro Glu Asn Gly Lys Pro Asn Ile Leu Asn
        35                  40                  45

Cys Tyr Val Thr Gln Phe His Pro Pro His Ile Glu Ile Gln Met Leu
    50                  55                  60

Lys Asn Gly Lys Lys Ile Pro Lys Val Glu Met Ser Asp Met Ser Phe
65                  70                  75                  80

Ser Lys Asp Trp Ser Phe Tyr Ile Leu Ala His Thr Glu Phe Thr Pro
                85                  90                  95

Thr Glu Thr Asp Thr Tyr Ala Cys Arg Val Lys His Asp Ser Met Ala
                100                 105                 110

Glu Pro Lys Thr Val Tyr Trp Asp Arg Asp Met Gly Gly Gly Gly Ser
                115                 120                 125

Gly Gly Gly Gly Ser Gly Gly Gly Ser Gly Gly Gly Gly Ser Gly
            130                 135                 140

Pro His Ser Leu Arg Tyr Phe Val Thr Ala Val Ser Arg Pro Gly Leu
145                 150                 155                 160

Gly Glu Pro Arg Phe Ile Ala Val Gly Tyr Val Asp Asp Thr Gln Phe
                165                 170                 175

Val Arg Phe Asp Ser Asp Ser Ala Ser Pro Arg Phe Glu Pro Arg Ala
                180                 185                 190

Pro Trp Val Glu Gln Glu Gly Pro Glu Tyr Trp Glu Glu Gln Thr Gln
                195                 200                 205

Arg Ala Lys Ser Asp Glu Gln Trp Phe Arg Met Ser Leu Gln Thr Ala
                210                 215                 220

Arg Gly Cys Tyr Asn Gln Ser Glu Ala Ser Ser His Thr Phe Gln Arg
225                 230                 235                 240

Met Phe Gly Cys Asp Leu Gly Ser Asp Gly Arg Leu Leu Arg Gly Tyr
                245                 250                 255

Gln Gln Phe Ala Tyr Asp Gly Arg Asp Tyr Ile Ala Leu Asn Glu Asp
                260                 265                 270

Leu Arg Ser Trp Thr Ala Ala Asp Thr Ala Ala Leu Ile Thr Lys Arg
                275                 280                 285

Lys Trp Glu Ala Ala Asn Asp Ala Glu Tyr Tyr Arg Ala Tyr Leu Glu
                290                 295                 300

Gly Glu Cys Val Glu Trp Leu His Arg Tyr Leu Glu Asn Gly Lys Glu
305                 310                 315                 320

Met Leu Gln Arg Thr Asp Ser Pro Lys Ala His Val Thr His His Pro
                325                 330                 335

Val Phe Asp Tyr Glu Ala Thr Leu Arg Cys Trp Ala Leu Gly Phe Tyr
                340                 345                 350

Pro Ala Glu Ile Ile Leu Thr Trp Gln Leu Asn Gly Glu Asp Leu Thr
                355                 360                 365

Gln Asp Val Glu Leu Val Glu Thr Arg Pro Ala Gly Asp Gly Thr Phe

```
                370                 375                 380
Gln Lys Trp Ala Ala Val Val Pro Ser Gly Lys Glu Gln Asn Tyr
385                 390                 395                 400

Thr Cys His Val Gln His Glu Gly Leu Pro Glu Pro Leu Met Leu Arg
                405                 410                 415

Trp Lys Gly Gly Gly Leu Asn Asp Ile Phe Glu Ala Gln Lys Ile Glu
                420                 425                 430

Trp His Glu His His His His His His
            435                 440

<210> SEQ ID NO 47
<211> LENGTH: 440
<212> TYPE: PRT
<213> ORGANISM: rat

<400> SEQUENCE: 47

Ala Gln Phe Ser Ala Ser Ala Ser Arg Gly Cys Gly Gly Ser Gly Gly
1               5                   10                  15

Gly Gly Ser Gly Gly Gly Gly Ser Ile Gln Lys Thr Pro Gln Ile Gln
                20                  25                  30

Val Tyr Ser Arg His Pro Pro Glu Asn Gly Lys Pro Asn Phe Leu Asn
            35                  40                  45

Cys Tyr Val Ser Gln Phe His Pro Pro Gln Ile Glu Ile Glu Leu Leu
50                  55                  60

Lys Asn Gly Lys Lys Ile Pro Asn Ile Glu Met Ser Asp Leu Ser Phe
65                  70                  75                  80

Ser Lys Asp Trp Ser Phe Tyr Ile Leu Ala His Thr Glu Phe Thr Pro
                85                  90                  95

Thr Glu Thr Asp Val Tyr Ala Cys Arg Val Lys His Val Thr Leu Lys
            100                 105                 110

Glu Pro Lys Thr Val Thr Trp Asp Arg Asp Met Gly Gly Gly Gly Ser
        115                 120                 125

Gly Gly Gly Gly Ser Gly Gly Gly Ser Gly Gly Gly Gly Ser Gly
    130                 135                 140

Ser His Ser Leu Arg Tyr Phe Tyr Thr Ala Val Ser Arg Pro Gly Leu
145                 150                 155                 160

Gly Glu Pro Arg Phe Ile Ala Val Gly Tyr Val Asp Asp Thr Glu Phe
                165                 170                 175

Val Arg Phe Asp Ser Asp Ala Glu Asn Pro Arg Met Glu Pro Arg Ala
            180                 185                 190

Arg Trp Met Glu Arg Glu Gly Pro Glu Tyr Trp Glu Gln Gln Thr Arg
        195                 200                 205

Ile Ala Lys Glu Trp Glu Gln Ile Tyr Arg Val Asp Leu Arg Thr Leu
    210                 215                 220

Arg Gly Cys Tyr Asn Gln Ser Glu Gly Gly Ser His Thr Ile Gln Glu
225                 230                 235                 240

Met Tyr Gly Cys Asp Val Gly Ser Asp Gly Ser Leu Leu Arg Gly Tyr
                245                 250                 255

Arg Gln Asp Ala Tyr Asp Gly Arg Asp Tyr Ile Ala Leu Asn Glu Asp
            260                 265                 270

Leu Lys Thr Trp Thr Ala Ala Asp Phe Ala Ala Gln Ile Thr Arg Asn
        275                 280                 285

Lys Trp Glu Arg Ala Arg Tyr Ala Glu Arg Leu Arg Ala Tyr Leu Glu
    290                 295                 300
```

```
Gly Thr Cys Val Glu Trp Leu Ser Arg Tyr Leu Glu Leu Gly Lys Glu
305                 310                 315                 320

Thr Leu Leu Arg Ser Asp Pro Pro Glu Ala His Val Thr Leu His Pro
            325                 330                 335

Arg Pro Glu Gly Asp Val Thr Leu Arg Cys Trp Ala Leu Gly Phe Tyr
            340                 345                 350

Pro Ala Asp Ile Thr Leu Thr Trp Gln Leu Asn Gly Glu Asp Leu Thr
            355                 360                 365

Gln Asp Met Glu Leu Val Glu Thr Arg Pro Ala Gly Asp Gly Thr Phe
    370                 375                 380

Gln Lys Trp Ala Ser Val Val Pro Leu Gly Lys Glu Gln Asn Tyr
385                 390                 395                 400

Thr Cys Arg Val Glu His Glu Gly Leu Pro Lys Pro Leu Ser Gln Arg
                405                 410                 415

Trp Gly Ser Gly Leu Asn Asp Ile Phe Glu Ala Gln Lys Ile Glu Trp
            420                 425                 430

His Glu His His His His His
        435                 440

<210> SEQ ID NO 48
<211> LENGTH: 440
<212> TYPE: PRT
<213> ORGANISM: Artificial
<220> FEATURE:
<223> OTHER INFORMATION: exemplary human HLA-G/ rat RT1A beta2M MHC
      class I complex wherein the positions specific for human HLA-G are
      grafted onto the rat RT1A framework

<400> SEQUENCE: 48

Ala Gln Phe Ser Ala Ser Ala Ser Arg Gly Cys Gly Gly Ser Gly Gly
1               5                   10                  15

Gly Gly Ser Gly Gly Gly Gly Ser Ile Gln Lys Thr Pro Gln Ile Gln
            20                  25                  30

Val Tyr Ser Arg His Pro Pro Glu Asn Gly Lys Pro Asn Phe Leu Asn
            35                  40                  45

Cys Tyr Val Ser Gln Phe His Pro Pro Gln Ile Glu Ile Glu Leu Leu
50                  55                  60

Lys Asn Gly Lys Lys Ile Pro Asn Ile Glu Met Ser Asp Leu Ser Phe
65                  70                  75                  80

Ser Lys Asp Trp Ser Phe Tyr Ile Leu Ala His Thr Glu Phe Thr Pro
                85                  90                  95

Thr Glu Thr Asp Val Tyr Ala Cys Arg Val Lys His Val Thr Leu Lys
            100                 105                 110

Glu Pro Lys Thr Val Thr Trp Asp Arg Asp Met Gly Gly Gly Gly Ser
            115                 120                 125

Gly Gly Gly Gly Ser Gly Gly Gly Ser Gly Gly Gly Gly Ser Gly
    130                 135                 140

Ser His Ser Leu Arg Tyr Phe Tyr Thr Ala Val Ser Arg Pro Gly Leu
145                 150                 155                 160

Gly Glu Pro Arg Phe Ile Ala Val Gly Tyr Val Asp Asp Thr Glu Phe
                165                 170                 175

Val Arg Phe Asp Ser Asp Ser Ala Ser Pro Arg Met Glu Pro Arg Ala
            180                 185                 190

Pro Trp Val Glu Gln Glu Gly Pro Glu Tyr Trp Glu Gln Gln Thr Arg
            195                 200                 205

Ile Ala Lys Glu Trp Glu Gln Ile Tyr Arg Met Asp Leu Gln Thr Leu
```

```
                210                 215                 220
Arg Gly Cys Tyr Asn Gln Ser Glu Ala Ser Ser His Thr Ile Gln Glu
225                 230                 235                 240

Met Tyr Gly Cys Asp Leu Gly Ser Asp Gly Arg Leu Leu Arg Gly Tyr
                245                 250                 255

Arg Gln Asp Ala Tyr Asp Gly Arg Asp Tyr Ile Ala Leu Asn Glu Asp
                260                 265                 270

Leu Arg Ser Trp Thr Ala Ala Asp Phe Ala Ala Gln Ile Thr Lys Arg
                275                 280                 285

Lys Trp Glu Ala Ala Asn Tyr Ala Glu Arg Leu Arg Ala Tyr Leu Glu
                290                 295                 300

Gly Thr Cys Val Glu Trp Leu His Arg Tyr Leu Glu Asn Gly Lys Glu
305                 310                 315                 320

Met Leu Gln Arg Ala Asp Pro Pro Glu Ala His Val Thr His His Pro
                325                 330                 335

Val Phe Asp Tyr Glu Ala Thr Leu Arg Cys Trp Ala Leu Gly Phe Tyr
                340                 345                 350

Pro Ala Glu Ile Ile Leu Thr Trp Gln Leu Asn Gly Glu Asp Leu Thr
                355                 360                 365

Gln Asp Val Glu Leu Val Glu Thr Arg Pro Ala Gly Asp Gly Thr Phe
                370                 375                 380

Gln Lys Trp Ala Ser Val Val Pro Ser Gly Lys Glu Gln Asn Tyr
385                 390                 395                 400

Thr Cys Arg Val Gln His Glu Gly Leu Pro Lys Pro Leu Met Leu Arg
                405                 410                 415

Trp Gly Ser Gly Leu Asn Asp Ile Phe Glu Ala Gln Lys Ile Glu Trp
                420                 425                 430

His Glu His His His His His
                435                 440

<210> SEQ ID NO 49
<211> LENGTH: 33
<212> TYPE: PRT
<213> ORGANISM: Artificial
<220> FEATURE:
<223> OTHER INFORMATION: linker and his-Tag

<400> SEQUENCE: 49

Gly Gly Gly Gly Ser Gly Gly Gly Ser Gly Ser Gly Leu Asn Asp
1               5                   10                  15

Ile Phe Glu Ala Gln Lys Ile Glu Trp His Glu His His His His
                20                  25                  30

His

<210> SEQ ID NO 50
<211> LENGTH: 9
<212> TYPE: PRT
<213> ORGANISM: Artificial
<220> FEATURE:
<223> OTHER INFORMATION: peptide

<400> SEQUENCE: 50

Val Leu Asp Phe Ala Pro Pro Gly Ala
1               5

<210> SEQ ID NO 51
<211> LENGTH: 107
<212> TYPE: PRT
```

<213> ORGANISM: Homo Sapiens

<400> SEQUENCE: 51

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 52
<211> LENGTH: 105
<212> TYPE: PRT
<213> ORGANISM: Homo Sapiens

<400> SEQUENCE: 52

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 53
<211> LENGTH: 328
<212> TYPE: PRT
<213> ORGANISM: Homo Sapiens

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 54
<211> LENGTH: 328
<212> TYPE: PRT
<213> ORGANISM: homo sapiens

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Gly Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 55
<211> LENGTH: 325
<212> TYPE: PRT
<213> ORGANISM: Homo Sapiens

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

-continued

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu
                325
```